US012678478B2

(12) United States Patent
Deb

(10) Patent No.: US 12,678,478 B2
(45) Date of Patent: Jul. 14, 2026

(54) COMPOSITIONS AND METHODS FOR TREATING DYSREGULATED WOUND HEALING

(71) Applicant: The Regents of the University of California, Los Angeles, CA (US)

(72) Inventor: Arjun Deb, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 865 days.

(21) Appl. No.: 17/916,337

(22) PCT Filed: Mar. 31, 2021

(86) PCT No.: PCT/US2021/025056
§ 371 (c)(1),
(2) Date: Sep. 30, 2022

(87) PCT Pub. No.: WO2021/202643
PCT Pub. Date: Oct. 7, 2021

(65) Prior Publication Data
US 2023/0149503 A1 May 18, 2023

Related U.S. Application Data

(60) Provisional application No. 63/002,828, filed on Mar. 31, 2020.

(51) Int. Cl.
*A61K 38/12* (2006.01)
*A61P 17/02* (2006.01)
*A61P 19/04* (2006.01)

(52) U.S. Cl.
CPC .............. *A61K 38/12* (2013.01); *A61P 17/02* (2018.01); *A61P 19/04* (2018.01)

(58) Field of Classification Search
None
See application file for complete search history.

(56) References Cited

U.S. PATENT DOCUMENTS

| | | |
|---|---|---|
| 2013/0129621 A1 | 5/2013 | Mackel et al. |
| 2015/0147386 A1 | 5/2015 | Feng et al. |
| 2020/0002424 A1 | 1/2020 | Celik et al. |
| 2021/0386740 A1* | 12/2021 | Dietz .................. A61K 31/407 |

FOREIGN PATENT DOCUMENTS

| | | | |
|---|---|---|---|
| WO | WO-97/11718 A1 | 4/1997 | |
| WO | WO-0121196 A1 * | 3/2001 | .............. A61P 41/00 |
| WO | WO-2021/202643 A1 | 10/2021 | |

OTHER PUBLICATIONS

Malfait, F. Vascular aspects of the Ehlers-Danlos Syndromes. Matrix Biol. 71-72:380-385, 2018). (Year: 2018).*
Justice et al. Using the mouse to model human disease: increasing validity and reproducibility, Disease, Models & Mechanisms 9:101-103, 2016). (Year: 2016).*
Fenton et al. Rheostat positions: A new classification of protein positions relevant to pharmacogenomics Medicinal Chemistry Research 29:1133-1146; 2020). (Year: 2020).*
Bhattacharya et al. Impact of genetic variation on three dimensional structure and function of proteins PLoS ONE 12(3): e0171355; 2017). (Year: 2017).*
Tokuriki et al. Stability effects of mutations and protein evolvability, Current Opinion in Structural Biology, 19:596-604, 2009. (Year: 2009).*
Guo et al. Protein tolerance to random amino acid change. PNAS USA 101(25):9205-10; 2004. (Year: 2004).*
Rudikoff et al. Single amino acid substitution altering antigen-binding specificity Proc. Natl. Acad. Sci. USA, 79(6):1979-1983, Mar. 1982. (Year: 1982).*
Bagnato et al., "Dual avb3 and avb5 blockade attenuates fibrotic and vascular alterations in a murine model of systemic sclerosis," Clinical Science, 132(2): 231-242 (2018).
Hinderer et al., "Cardiac fibrosis-A short review of causes and therapeutic strategies," Adv Drug Delivery Reviews, 146: 77-82 (2019).
International Search Report and Written Opinion for International Application No. PCT/US2021/025056 mailed Jul. 20, 2021.
Ritelli et al., "Clinical and molecular characterization of 40 patients with classic Ehlers-Danlos syndrome identification of 18 COL5A1 and 2 COL5A2 novel mutations," Orphanet Journal of Rare Diseases, 8(1): 1-19 (2013).
Wenstrup et al., "COL5A1 haploinsufficiency is a common molecular mechanism underlying the classical form of EDS," Am J Hum Genet, 66(6): 1766-1776 (2000).
Written Opinion of the International Preliminary Examining Authority for International Application No. PCT/US2021/025056 dated Dec. 27, 2021.
Zhou et al., "An integrin antagonist (MK-0429) decreases proteinuria and renal fibrosis in the ZSF1 rat diabetic nephropathy model," Pharmacol Res Perspect, 5(5): e00354 (2017).
Zoppi et al., "Human fibroblasts with mutations in COL5A1 and COL3A1 genes do not organize collagens and fibronectin in the extracellular matrix, down-regulate $\alpha2\beta1$ integrin, and recruit $\alpha v\beta3$ instead of $\alpha5\beta11$ integrin," J Biol Chem, 279(18): 18157-18168 (2004).
Perrucci et al., "Integrin $\alpha v\beta5$ in vitro inhibition limits pro-fibrotic response in cardiac fibroblasts of spontaneously hypertensive rats", *Journal of Translational Medicine* 16: 1-13 (2018).

(Continued)

*Primary Examiner* — Bridget E Bunner
*Assistant Examiner* — Regina M DeBerry
(74) *Attorney, Agent, or Firm* — Foley Hoag LLP; David P. Halstead; Erin M. Foley

(57) ABSTRACT

The present disclosure relates to compositions and methods for treating a dysregulated wound healing, for improving wound healing, for inhibiting scar formation, for treating a subject with Ehlers Danlos syndrome (EDS), and for treating a subject diagnosed with a heart attack. The present disclosure further relates to compositions and methods for predicting future cardiac risk in a subject who has suffered a heart attack, and predicting risk of future cardiac disease in a subject suffering a heart attack.

17 Claims, 39 Drawing Sheets

(56) References Cited

OTHER PUBLICATIONS

Sarrazy et al., "Integrins αvß5 and αvß3 promote latent TGF-ß1 activation by human cardiac fibroblast contraction", *Cardiovascular research* 102.3: 407-417 (2014).

Supplementary European Search Report for EP Application No. 21779012.0 dated Mar. 28, 2024.

Yokota et al., "Type V collagen in scar tissue regulates the size of scar after heart injury", *Cell* 182.3: 545-562 (2020).

* cited by examiner

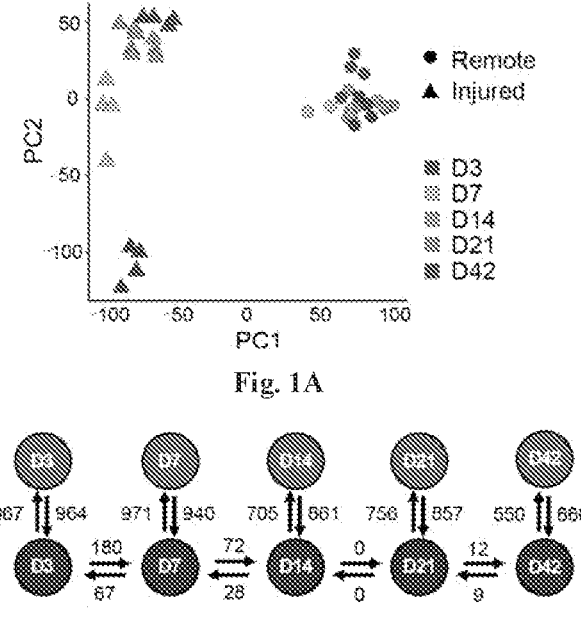
Fig. 1A
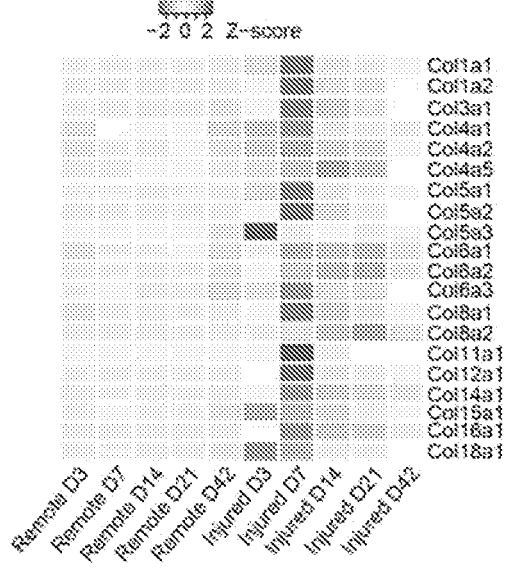
Fig. 1B
Fig. 1C

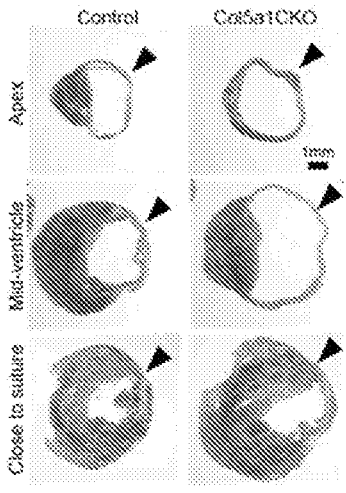
Fig. 3C
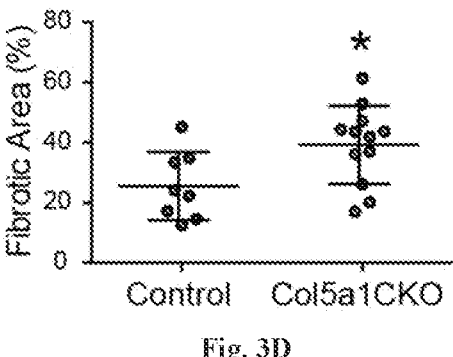
Fig. 3D
Severity of fibrosis (%)
Severe  Moderate  Mild
Control          Col5a1CKO
Fig. 3E A
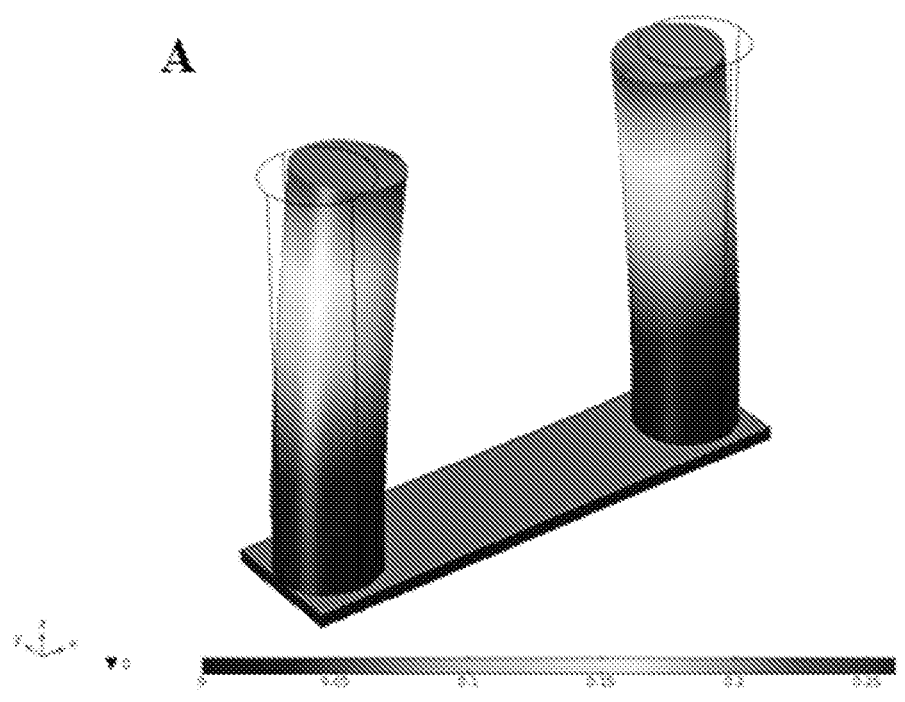
Displacement (mm)
Fig. 11A
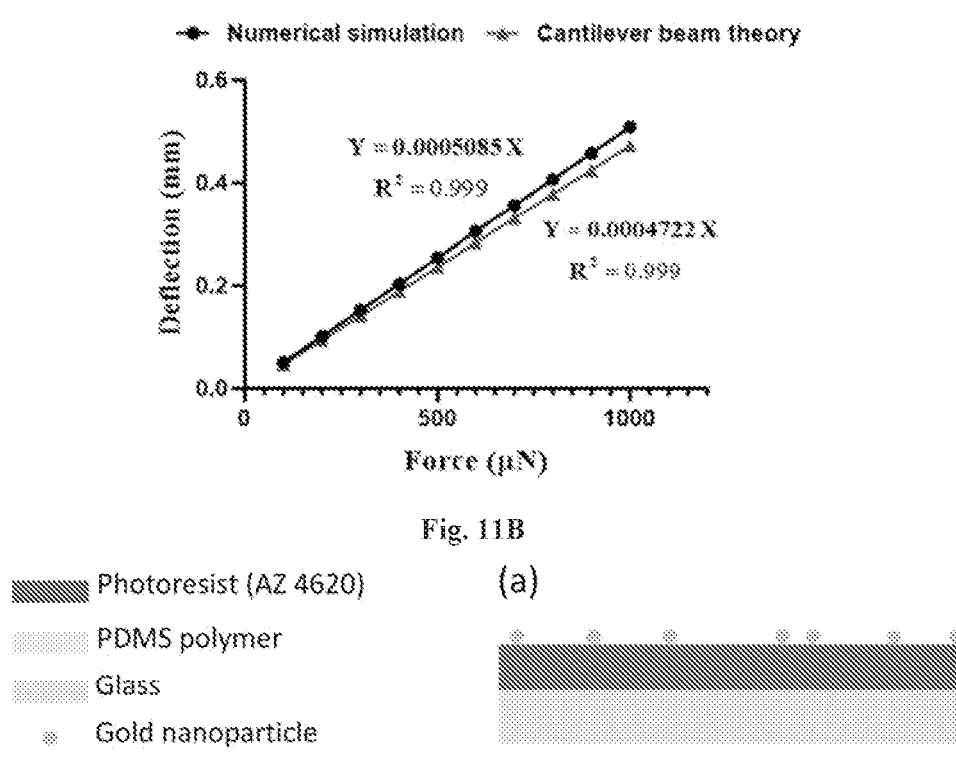
Fig. 11B
Fig. 12A Control fibroblasts + NRVMs

COMPOSITIONS AND METHODS FOR TREATING DYSREGULATED WOUND HEALING

RELATED APPLICATIONS

This application is a U.S. National Stage Application of PCT/US21/25056, filed Mar. 31, 2021, which claims the benefit of priority to U.S. Provisional Patent Application 63/002,828 filed Mar. 31, 2020. The contents of each of which are hereby incorporated herein by reference in their entirety.

STATEMENT REGARDING FEDERALLY SPONSORED RESEARCH

This invention was made with Government support under Grant Number HL137241, awarded by the National Institutes of Health and under Grant Number W81XWH-17-1-0464, awarded by the U.S. Department of Defense. The Government has certain rights in the invention.

BACKGROUND

Acute myocardial infarction affects more than 700,000 people in the United States annually and accounts for more than 40% of all cases of heart failure. Following acute ischemic cardiac injury, dead cardiac muscle is replaced by scar tissue. Clinical studies demonstrate that scar size or degree of fibrosis in patients with prior myocardial infarction is an independent predictor of mortality and outcomes, even when normalized with respect to cardiac function (i.e. individuals with identical cardiac contractile function but greater degree of fibrosis have higher mortality rates and worse outcomes). Individuals with comparable degrees of myocardial necrosis following ischemic injury may exhibit disparate wound healing responses and consequently have significant differences in scar size and clinical prognosis. Despite the immense pathophysiologic importance of scar burden following acute myocardial infarction, little is known about factors that regulate scar size after ischemic cardiac injury. New approaches for treating and/or managing this disease are needed.

SUMMARY

The present invention is based, at least in part, on the discovery that collagen V, a fibrillar collagen and a minor constituent of heart scars, regulates the size of heart scars after ischemic cardiac injury. Collagen V deficiency alters the ultra-structure and mechano-biological properties of scar tissue. These changes result in cardiac fibroblasts expressing specific integrins that drive fibroblast activation, increase myofibroblast formation, and upregulate expression of Extracellular matrix (ECM) genes thereby increasing scar size. Administration of cilengitide, an inhibitor of specific integrins, completely rescues the phenotype of increased post injury scarring, myofibroblast formation and cardiac dysfunction in collagen V deficient mice. These observations demonstrate that collagen V, a structural constituent of heart scar tissue regulates scar size in an integrin dependent manner.

In some aspects, disclosed herein are methods for treating a dysregulated wound healing in at subject. Such methods may include administering, to the subject an inhibitor of integrin Numerous embodiments are further provided that can be applied to any aspect of the present invention described herein. For example, in some embodiments, the inhibitor of integrin is an inhibitor of αvβ3 integrin, such as a compound selected from Table 1 (e g, cilengitide). In some embodiments, the inhibitor of integrin is an inhibitor of αvβ5 integrin, such as a compound selected from Table 2. In sone embodiments, the subject has Ehlers Danlos Syndrome, or acute myocardial infarction.

Such methods may include conjointly administering to the subject an inhibitor of αvβ3 integrin (such as a compound selected from Table 1, e.g., cilengitide) and an inhibitor of αvβ5 integrin (a compound selected from Table 2). In some such embodiments, the subject has Ehlers Danlos Syndrome, or acute myocardial infarction.

In some aspects, disclosed herein are methods for inhibiting scar formation in a subject. Such methods may include administering to the subject an inhibitor of integrin. Numerous embodiments are further provided that can be applied to any aspect of the present invention described herein. For example, in some embodiments, the inhibitor of integrin is an inhibitor of αvβ3 integrin, such as a compound selected from Table 1 (e.g. cilengitide). In some embodiments, the inhibitor of integrin is an inhibitor of αvβ5 integrin, such as a compound selected from Table 2. In some embodiments, the subject has Ehlers Danlos Syndrome, or acute myocardial infarction.

Such methods may include conjointly administering to the subject an inhibitor of αvβ3 integrin (such as a compound selected from Table 1, e.g., cilengitide) and an inhibitor of αvβ5 integrin (a compound selected from Table 2). In some such embodiments, the subject has Ehlers Danlos Syndrome, or acute myocardial infarction.

In some aspects, disclosed herein are methods for improving wound healing in a subject. Such methods include administering to the subject an inhibitor of integrin. Numerous embodiments are further provided, that can be applied to any aspect of the present invention described herein. For example, in sone embodiments, the inhibitor of integrin is an inhibitor of αvβ3 integrin, such as a compound selected from Table 1 (e.g., cilengitide). In some embodiments, the inhibitor of integrin is an inhibitor of αvβ5 integrin, such as a compound selected from Table 2. In some embodiments, the subject has Ehlers Danlos Syndrome, or acute myocardial infarction.

Such methods may include conjointly administering to the subject an inhibitor of αvβ3 integrin (such as a compound selected from Table 1, e.g., cilengitide) and an inhibitor of αvβ5 integrin (a compound selected firm Table 2). In some such embodiments, the subject has Ehlers Danlos Syndrome, or acute myocardial infarction.

In some aspects, disclosed herein are methods of treating a subject with Ehlers Danlos syndrome (EDS). Such methods include administering to the subject an inhibitor of integrin. Numerous embodiments are further provided that can be applied to any aspect of the present invention described herein. For example, in some embodiments, the inhibitor of integrin is an inhibitor of αvβ3 integrin, such as a compound selected from Table 1 (e.g., cilengitide), in other embodiments, the inhibitor of integrin is an inhibitor of αvβ5 integrin, such as a compound selected from Table 2.

In various embodiments described herein, the Ehlers Danlos syndrome is classic Ehlers Danlos syndrome (cEDS). In sone embodiments, the subject suffers from exaggerated and aberrant wound healing with increased scarring: following injury trauma or surgery, the subject has a mutation in Col5a1 (such as haploinsufficiency), or the subject exhibits up-regulation of αvβ3 integrin receptor. In some embodiments, the inhibitor of integrin is administered 1 to 30 days prior to a surgery or childbirth, is administered 7 days prior to the surgery or childbirth, or is administered daily. In some embodiments, the inhibitor of integrin is administered after the surgery or childbirth until healing of wound has occurred, is administered 1 to 30 days after the surgery or childbirth, is administered 1 to 7 days after the surgery or childbirth, or is administered daily. In some embodiments, the inhibitor of integrin is administered after an acute trauma until healing of wound has occurred, is administered 1 to 30 days after the acute trauma, is administered 1 to 14 days after the acute trauma, is administered 1 to 7 days after the acute trauma, or the inhibitor of integrin is administered daily.

In some aspects, disclosed herein are methods of predicting future cardiac risk in a subject who has suffered a heart attack. Such methods may include: (1) measuring a Col5a1 expression level in a sample from the subject; and (2) comparing the Col5a1 expression level in the sample to a predetermined Col5a1 reference value, wherein the predetermined Col5a1 reference value corresponds to Col5a1 expression level in healthy subjects; wherein a decreased measured expression level of Col5a1 relative to the reference value is indicative of a poor clinical outcome. Numerous embodiments are further provided that can be applied to any aspect of the present invention described herein. For example, in sone embodiments, the sample is obtained from peripheral blood. In some embodiments, the Col5a1 expression level is determined via a PCR-based analysis.

In some aspects, disclosed herein are methods of predicting risk of future cardiac disease in a subject suffering a heart attack. Such methods may include identifying an aberrant mutation in Col5a1 in a sample from the subject, wherein an aberrant mutation in Col5a1 is indicative of a poor clinical outcome. Numerous embodiments are further provided that can be applied to any aspect of the present invention described herein. For example, in some embodiments, the sample is obtained from peripheral blood. In some embodiments, the Col5a1 mutation is determined via a PCR based analysis. The mutation may be haploinsufficiency.

In some aspects, disclosed herein are methods of treating a subject diagnosed with a heart attack. Such methods may include the steps of: (1) quantifying Co5a1 levels in a sample from the subject; (2) comparing the Col5a1 levels in the sample to a predetermined Col5a1 threshold, wherein the predetermined Col5a1 threshold corresponds to Col5a1 levels in a healthy subject; wherein the heart attack is determined to be treatable with an inhibitor of integrin when the Col5a1 levels in the sample are lower than the predetermined Col5a1 threshold; and (3) administering an inhibitor of integrin to the subject diagnosed with the heart attack determined to be treatable with an inhibitor to integrin. Numerous embodiments are further provided that can be applied to any aspect of the present invention described herein. For example, in some embodiments, the sample is obtained from peripheral blood. In some embodiments, the Colfa1 expression levels are determined via a PCR based analysis. In some embodiments, the inhibitor of integrin is an inhibitor of αvβ3 integrin, such as a compound selected from Table 1 (e.g., cilengitide). In some embodiments, the inhibitor of integrin is an inhibitor of βvβ5 integrin, such as a compound selected from Table 2. In some embodiments, the inhibitor of integrin is administered daily, is administered after the heart attack until recovery, is administered 1 to 30 days after the heart attack, or is administered 1 to 7 days after the heart attack.

In some aspects, disclosed herein are methods of assessing a prognosis in a patient after ischemia, acute kidney injury, liver injury, skeletal muscle injury, or stroke. Such methods may include: (1) measuring a Cl5a1 expression level in a sample from the subject; and (2) comparing the Col5a1 expression level in the sample to a predetermined Col5a1 reference value, wherein the predetermined Col5a1 reference value corresponds to Col5a1 expression levels in healthy subjects; wherein a decreased measured expression level of Col5a1 relative to the reference value is indicative of a poor clinical outcome. Numerous embodiments are further provided that can be applied to any aspect of the present invention described herein. For example, in some embodiments, the sample is obtained from peripheral blood. In some embodiments, the Col5a1 expression level is determined via a PCR-based analysis.

In some aspects, disclosed herein are methods of assessing a prognosis in a patient after ischemia, acute kidney injury, liver injury, skeletal muscle injury, or stroke. Such methods may include identifying an aberrant mutation in Col5a1 in a sample from the subject, wherein an aberrant mutation in Col5a1 is indicative of a poor clinical outcome. Numerous embodiments are further provided that can be applied to any aspect of the present invention described herein. For example, in some embodiments, the sample is obtained from peripheral blood. In some embodiments, the Col5a1 mutation is determined via a PCR based analysis. The mutation may be haploinsufficiency.

DESCRIPTION OF THE FIGURES

FIGS. 1A-1D show Temporal changes in gene expression profile of scar tissue following acute ischemic cardiac injury, FIG. 1A shows principal component analysis (PCA) based on expression profiles of all genes. Samples from injured and uninjured regions (remote to area of injury) are coded by shapes, and timepoints (days after injury) are coded by shades, as indicated (n=4 animals/group). FIG. 1B shows summary of differential gene expression analysis. Arrows and numbers indicate direction and numbers of differentially expressed genes (DEGs) detected in each pairwise comparison. For example, 180 DEGs were upregulated between samples from injured regions at Day 3 (D3) and Day 7 (D7). DEGs were identified at FDR 1% and minimum fold-change value of 4. FIG. 1C shows heatmap with expression patterns of collagen genes. For each gene, relative expression levels across conditions are shown by shades in Z-scores, as in scale. Expression levels for each condition were averaged across 4 biological replicates. FIG. 1D shows qPCR to determine expression of collagen genes encoding for obligatory units of the respective collagen (n=5 animals/group/ time point, *$p<0.5$, compared to expression of respective collagen in uninjured region at that time point, data shown as mean±S.D.).

FIG. 2A shows scar tissue and remote region (uninjured) of myocardium at day 7 following injury were subjected to mass spectrometry and proteomic analysis and expression of individual collagen chains determined. Proteomic heat map demonstrating changes in expression of individual collagen chains between injured and uninjured regions (n=3 samples). FIG. 2B shows normalized expression levels (RPKM) for selected collagen genes. Average expression levels for each condition and changes across timepoints are shown in black symbols and dashed lines. Expression levels for individual replicates are shown in gray symbols (n=4). FIG. 2C shows RNA-FISH to demonstrate expression of Col5a1, Col1a1 and Col3a1 in the heart at 7 days following ischemic injury (solid arrowhead, representative images, n %4 animals, unfilled arrowhead indicates uninjured region). FIG. 2D shows higher magnification demonstrating co-localization of Col5a1 with Col1a1 and Col3a1 within the same cell (arrows, representative images, n=4 animals). FIG. 2E shows expression of Col5a1 in cardiac fibroblasts genetically labeled by the TCF21 or Col1a2 label but FIG. 2F not in cardiomyocytes (Troponin I stained) in the injury region (arrows, representative images, n=3 animals). FIG. 2G shows single cell RNA-seq of non-myocytes isolated from the injured heart at 7 days following injury demonstrating typical cell phenotypes in clusters and distribution of Col1a1, Col3a1 and Col5a1 across these cell clusters (n=3).

FIGS. 3A-3L show that animals with Col5a1 deletion in cardiac fibroblasts exhibit a paradoxical increase in scar tissue after heart injury. FIG. 3A shows M mode echocardiogram demonstrating left ventricular walls and internal dimension (line with arrows) prior to (basal) and 6 weeks following injury in Col5a1CKO and control littermates (representative images, n=12 animals/control and 27/CKO at Day 0 and a=8 control and 12/CKO at 6 weeks post MI). FIG. 3B shows ejection fraction and Fractional shortening in Col5a1CKO and control littermates at different time points following injury (mean±S.D., *p<0.05 between the two groups, n=12 Control and 27 CKO at basal, n=10 Control and 22 CKO at 3D post MI, n=9 Control and 15 CKO at 1 wk post MI, n=9 Control and 13 CKO at 2 wks post MI, n=: Control and 12 CKO at 4 and 6 wks post M1). Left ventricular dimensions in end diastole (LVIDd) and end systole (LVIDs) at different time points following injury (Same number of animals as for determining EF/FS). FIG. 3C shows masson trichrome staining of hearts of Col5a1CKO and control littermates sectioned at the base (just distal to suture line) at mid ventricle and apex 6 weeks following injury (representative images shown, n=8 animals/Control and 12/CKO) FIG. 3D shows quantification of surface area of scar normalized to the surface area of the ventricle (meant±S.D., *1p<0.05, n=S animals/Control and 12/CKO). FIG. 3E shows fraction of animals in the Col5a1CKO and control groups that demonstrate mild/moderate or severe scarring at 6 weeks following injury. (mild scarring <20% of surface area, moderate between 20 and 40% of ventricular surface area and severe >40% of surface area). FIG. 3F shows measurement of insoluble collagen in Col5a1CKO and control animals in scar tissue at 4 weeks following heart injury (mean±S.D., *p<0.05, n=4). FIG. 3G shows toluidine blue staining of scar tissue from control littermate or Col5a1CKO animal at 4 weeks following injury demonstrates wavy compact arrangement of collagen fibers in control but loss of such compact pattern in Col5a1CKO hearts (arrowhead; representative images, n=3 samples/group). FIG. 3H shows transmission electron microscopy (TEM) of scar area shows collagen fibers arranged in parallel in control group but fibrillar disarray in the Col5a1CKO scar tissue (arrowhead. FB=fibroblast). FIG. 3I shows higher magnification with TEM demonstrating fibrillar disarray with fibrils running in orthogonal axes to each other in the Col5a1CKO scar tissue (arrowhead). FIG. 3J shows cross sectional TEM view demonstrating fibril diameter size in control and Col5a1CKO scar tissue (arrowheads, n=3 samples/group for all TEM), FIG. 3K shows average collagen fibril diameter in scars of control and Col5a1CKO hearts calculated by Image J (mean±S.D., *p<0.05, n=3 samples/group). FIG. 3L, shows histogram of collagen fibrils of various diameters demonstrates a clear shift to the right for the fibrils in Col5a1CKO scars (n=G samples/group).

FIG. 4A shows that TCF21MCM:Col5a1CKO mice were generated by crossing the TCF21iMerCreMer mice with the Col5a1 floxed mice. Expression of Col5a1 in the injury region by RNA-FISH in TCF21MCM:Col5a1CKO animals compared to control littermates (arrows, representative images), FIG. 4B shows quantitative decrease in Col5a1 expression in TCF21MCM:Col5a1CKO mice compared to control littermates (mean±SD. p<0.05, n=–6 animals/Control and 4/CKO). FIG. 4C shows M mode echocardiogram demonstrating left ventricular walls and internal dimension (line with arrows) prior to (basal) and 6 weeks following injury in TCF21MCM:Col5a1CKO and control littermates (representative images, n=12 Control and 18 CKO at basal. n=9 Control and 10 CKO at 6 wks post MI). FIG. 4D shows ejection fraction and Fractional shortening in TCF21MCM:Col5a1CKO and control littermates at different time points following injury (mean±S.D., *p<0.05, n==12 animals/Control and 18/CKO at basal, n-9/Control and 14/CKO at 3D post MI. n=9/Control and 12/CKO at 1 wk postMI, n=9/Control and 10/CCKO at 2-6wks post MI). Left ventricular dimensions in end diastole (LVIDd) and end systole (LVIDs) at different time points following injury. FIG. 4E shows masson trichrome staining of hearts of TCF21MCM:Col5a1CKO and control littermates sectioned at the base (just distal to suture line) at mid ventricle and apex 6 weeks following injury (representative images shown, n=9 animals/Control and 10/CKO). FIG. 4F shows quantification of surface area of scar normalized to the surface area of the left ventricle (mean±S.D., *p<0.05, n=9 animals/Control and 10/CKO). FIG. 4C shows fraction of animals in the TCF21MCM:Col5a1CKO and control groups that demonstrate mild/moderate or severe scarring at 6 weeks following injury. (mild scarring <20% of surface area, moderate between 20 and 40% of ventricular surface area and severe >40% of surface area). FIG. 4H shows heart weight/body weight ratio in TCF21MCM:Col5a1CKO and control animals at 6 weeks following injury. (mean±S.D., *p<c0.05, n=9 Control and 8 CKO). FIG. 4I shows immunostaining of mid ventricular heart sections of TCF21MCM: Col5a1CKO and control littermates with Troponin I and Wheat germ agglutinin (WGA) at 6 weeks following injury to determine surface area (cross sectional area, arrowhead) of cardiomyocytes (representative images, n=7 animals/Control and 9/CKO). FIG. 4J shows quantitation of surface area of individual cardiomyocytes between TCF21 MCM:Col5a1CRKO and Control groups at 6 weeks following injury (mean±S.D., *p<0.05, n=–7 animals/Control and 9/CKO).

FIG. 5A shows HMDP comprising 96 strains of mice were subjected to continuous isoproterenol or vehicle infusion for 3 weeks with serial temporal assessment of cardiac functional traits and left ventricular gene expression. FIG. 5B shows genetic variation of ECM genes including collagens following isoproterenol or control (PBS) infusion across all strains in the HMDP, FIG. 5C and FIG. 5D show gene X trait analysis demonstrating strength of association between individual ECM genes and cardiac traits determining chamber size (LVID), hypertrophy (LV mass) and diastolic function (E/A ratio) under (FIG. C) control or (FIG. D) isoproterenol injected animals (54 correlations were found to be significant (p<0.05) under control conditions in contrast to 86 significant correlations following isoproterenol infusion). Scale showing bicorrelation coefficient and corresponding p value for all heatmaps in the figure. FIG. 5E shows Genetic variation in Col5a1 expression across the HMDP, following control or Isoproterenol treatment. FIG. 5F shows that strength of association between Col5a1 expression and expression of ECM genes, significant correlations (p<0.05) are shows as asterisks below. FIG. 5G shows that illustration of hypothesis of how adjustment for Col5a1 could significantly change the strength of association between ECM genes and cardiac traits. FIG. 5H shows conditional analysis demonstrating the strength of correlation (-log p value) between ECM genes and different cardiac traits either unadjusted or following adjustment for Col5a1 expression (*p<0.005, p<0.01, compared to isoproterenol unadjusted).

FIG. 6A shows tSNE plot demonstrating different clusters of non-myocyte cell populations of the heart at 7 days following injury according to canonical gene expression signatures. FIG. 6B shows distribution of non-myocyte cells from injured Ctrl and Col5a1CKO hearts across these clusters. FIGS. 6C-6E shows violin plot demonstrating expression of (FIG. C) Col5a1, (FIG. D) Acta2 (SMA), (FIG. E) CNN2 (Calponin) in fibroblast clusters. FIG. 6F shows sub-clustering of fibroblast population and distribution of control and CKO fibroblasts across fibroblast subclusters. FIG. 6G shows expression of Acta2 in subclusters of fibroblasts demonstrating Cluster 0 to be enriched in cells expressing Acta 2. FIG. 6H shows cell numbers in Cluster 0 (myofibroblasts) versus Cluster 1 and 2 (non-myofibroblasts) in Control and Col5a1CKO animals. FIG. 6I shows immunostaining for αsmooth muscle actin (αSMA) and vimentin in the injury region of control littermates and Col5a1CKO hearts at 7 days following ischemic injury (arrows, representative images, n=4 aminals/Control and 5/CKO). FIG. 6J shows quantitation of the number of αSMA expressing cells in the injury region as a fraction of the number of vimentin expressing cells (mean±S.D., *p<0.05, n=4 animals/Control and 5/CKO), FIG. 6K shows immunostaining for αsmooth muscle actin (αSMA) and vimentin in the injury region of TCF21MCM:Col5a1CKO hearts at 7 days following ischemic injury (arrows, representative images, n=4 animals/Control and 5/CKO). FIG. 6L shows Quantitation of the number of αSMA expressing cells in the injury region as a fraction of the number of vimentin expressing cells (mean±S.D., *p<0.05, n=4 animals/Control and 5/CKO). FIG. 6M shows dot plot representing expression of ECM genes that are upregulated in fibroblasts of Col5a1CKO hearts at 7 days following injury compared to controls.

FIGS. 7A-7D show determination of mutant or control cardiac fibroblasts to generate contractile forces. FIG. 7A shows that cardiac fibroblasts were isolated from control or Col5a1CKO mice at 7 days after injury and incorporated into hydrogel scaffolds and suspended between PDMS posts FIG. 7B shows contraction of fibroblasts determined from displacement of PDMS posts. FIG. 7C shows displacement of PDMS posts by control or Col5a1CKO fibroblast tissue scaffold (mean±S.D., *p<0.05, n=3 independent experiments). FIG. 7D shows contraction forces generated by either Control or Col5a1CKO cardiac fibroblasts (mean±S.D., *p<0.05, n=3 independent experiments) FIG. 7E shows that Col5a1fl/fl cardiac fibroblasts from hearts of Col5a1fl/fl mice were infected with a lentiviral Cre or GFP control virus to create fibroblasts deficient in Col5a1. A similar tissue scaffold was created as in (FIG. 7A) and scaffold suspended between PDMS posts. FIG. 7F shows displacement of the PDMS posts and FIG. 7G contractile forces generated by control or Col5a1CKO fibroblasts generated by ex vivo Cre transduction (mean±S.D., *p<0.05, n=3 independent experiments) FIGS. 7H-7I shows representative QPM images demonstrating heat map of mass/density in (FIG. 7H) control and (FIG. 7I) Col5a1CKO fibroblasts and (FIG. 7J) decorrelation rate of control and Col5a1CKO fibroblasts and (FIG. 7K) cell stiffness (inverse of decorrelation rate) of control and Col5a1CKO cardiac fibroblasts (means±S.D., *p<0.05, n=3 independent experiments with 11 cell clusters examined/control and 18 cell clusters/Col5a1CKO). FIGS. 7L-7N shows traction force microscopy (TFM) to determine how control or Col5a1CKO cardiac fibroblasts affect myocyte contraction forces, FIG. 7L shows schematic of set up of TFM where myocytes and cardiac fibroblasts are seeded onto a matrigel layer containing gold labeled nanoparticles. FIG. 7M shows heat maps demonstrating displacement of clusters of contracting myocytes in the presence of control or Col5a1CKO cardiac fibroblasts and FIG. 7N shows determination of stress forces generated by cardiomyocytes in the presence of control or Col5a1CKO cardiac fibroblasts (mean±S.D., *p<0.05, n=3 independent experiments).

FIG. 8A shows that Col5a1CKO cardiac fibroblasts (generated by lentiviral Cre transduction) or control cardiac fibroblasts (Col5a1CKO fibroblasts infected with a GFP virus) were subjected to qPCR for expression of ECM and myofibroblast genes (mean±S.D., *p<105, n=6 independent experiments). FIG. 8I shows M mode echocardiograms demonstrating better contractile function (representative images, line indicates end systolic diameter) in cilengitide treated Col5a1CKO animals. FIG. 8O shows immunostaining for cardiac troponin and WGA to determine myocyte surface area as a surrogate for hypertrophy in the border zone region of Col5a1CKO animals injected with vehicle or cilengitide (arrows, representative images, same animals as above) (mean±S.D., *p<0.05, n=same number of animals as above).

FIG. 9A shows schematic of master mold. FIG. 9B shows schematic of wells and microposts. FIG. 9C shows top view of wells and microposts. The dimensions are in mm. FIG. 9D shows PMM A master mold FIG. 9E shows PDMS wells and two microposts (All scale bares are 3 mm).

FIGS. 11A-11B shows numerical analysis of mechanics of the PDMS microposts using FEA. FIG. 11A shows displacement of microposts after applying 500 μN force to the free end of cantilever. FIG. 11B shows relationship between deflection of micropost and applied force in numerical simulation and cantilever beam theory.

FIGS. 12A-12C shows fabrication of bio-sensor devices. FIG. 12A shows that photoresist was spin coated and baked on glass. Then gold nanoparticles suspended in citrate buffer were deposited and dried overnight. FIG. 12H shows that uncured PDMS polymer was poured over the gold nanoparticles and capped with a glass coverslip, and left to cure overnight. FIG. 12C shows that photoresist was dissolved by immersion in acetone overnight to release the final device.

FIG. 13A shows randomly generated stress distribution. FIG. 13B shows corresponding displacement fields solved by COMSOL software.

FIG. 14A shows experimentally extracted displacements of the gold nanoparticles for the control group. FIG. 14B shows displacements of gold nanoparticles for the mutant group. FIG. 14C shows interpolated displacements for the control group after Fourier filtering. FIG. 14D shows interpolated displacements for the mutant group after Fourier filtering. FIG.

14E shows stresses predicted by the machine learning model for the control group. FIG. 14F shows stresses for the mutant group. FIG. 14G shows simulated displacements from COMSOL software using predicted stresses from control group, FIG. 14H shows simulated displacements from COMSOL software using predicted stresses from mutant group.

DETAILED DESCRIPTION OF THE INVENTION

Figure 1D:
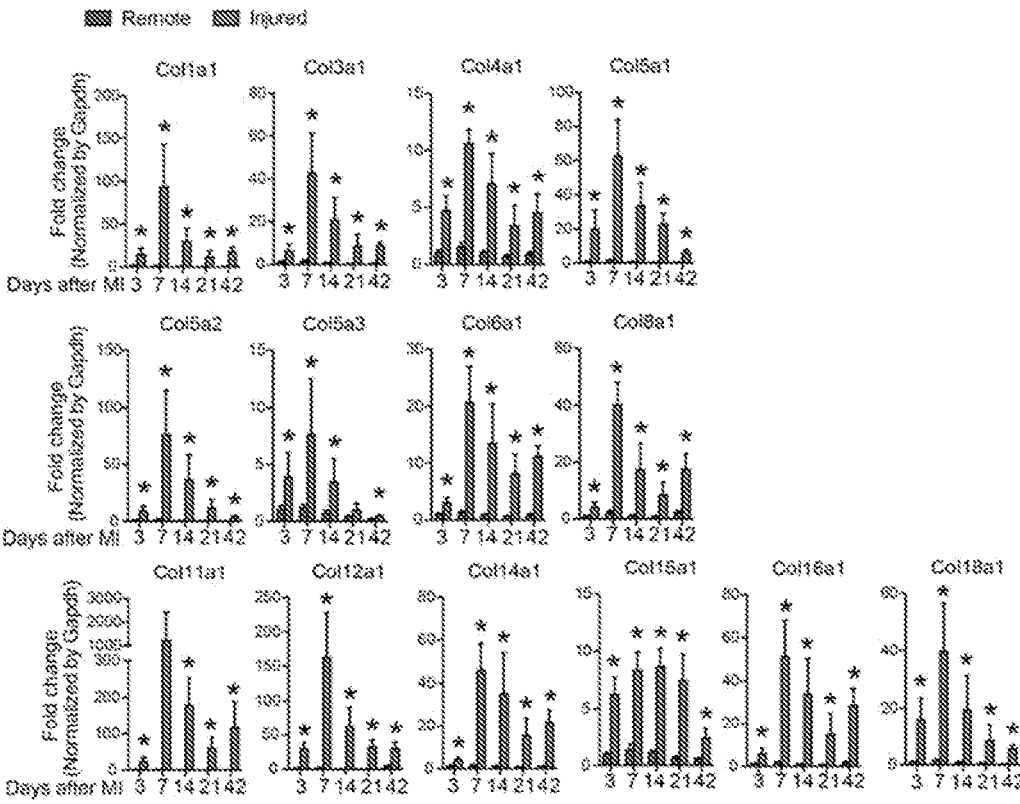

The mammalian heart has limited ability to regenerate after acute ischemic cardiac injury and lost cardiac muscle is replaced by scar tissue. Multiple clinical studies demonstrate that the size of scar tissue or degree of fibrosis following myocardial infarction is an independent predictor of cardiovascular outcomes, yet little is known about factors that regulate the size of scar after ischemic cardiac injury. The present invention is based, at least in part, on the discovery that collagen V, a fibrillar collagen and a minor constituent of heart scars, regulates the size of heart scars after ischemic cardiac injury. Depletion of collagen V in heart scars in two independent animal models led to a significant and paradoxical increase in post infarction scar tissue size with worsening of heart function. A systems genetics approach analyzing genes versus traits across 100 in-bred strains of mice independently demonstrated that collagen V is a critical driver of post injury heart function. Collagen V deficiency alters the ultra-structure and mechano-biological properties of scar tissue. These changes result in cardiac fibroblasts expressing specific integrins that drive fibroblast activation, increase myofibroblast formation, and upregulate expression of Extracellular matrix (ECM) genes thereby increasing scar size. Administration of cilengitide, an inhibitor of specific integrins, completely rescues the phenotype of increased post injury scarring, myofibroblast formation and cardiac dysfunction in collagen V deficient mice. These observations demonstrate that collagen V, a structural constituent of heart scar tissue regulates scar size in an integrin dependent manner.

To identify factors determining scar size after myocardial infarction, mice were subjected to ischemic cardiac injury and transcriptional profiling of heart scars harvested at different time points ranging from 3 days to 6 weeks after injury was performed. Collagens were one of the most highly differentially upregulated genes in the injured heart early after ischemic cardiac injury. Collagens I and III are the most abundant collagens present in the uninjured heart comprising approximately 90-95% of all collagens in the heart and belong to the family of fibrillar collagens that confer mechanical strength to tissues. However, more than 26 types of collagens have been described in mammals and although the triple helical structure is common to all collagens, they differ in their mechanical, biological properties, tissue specific expression and function. Using transcriptomic profiling and proteomic approaches, it is demonstrated that a large number of different collagens including several collagens, that are minimally expressed in the uninjured heart, are robustly expressed in scar tissue after heart injury. But, the physiological necessity for the heterogeneity of collagen expression in the injured heart is unclear.

Collagen V regulates scar size after ischemic cardiac injury. Collagen V like collagen I and III belong to the family of fibril forming collagens, but unlike collagen I and III, collagen V is minimally present in the uninjured heart and even following injury, gene expression of Col5a1 is significantly lower than that of Cola1 or Col3a1. Collagen V usually exists in tissues as a heterotrimer and the Col5a1 gene encodes for the obligatory α1(V) chain of collagen V. Global deletion of the Col5a1 gene results in the absence of any functional collagen V in tissues and leads to early embryonic lethality from abnormal mesenchyme development and cardiac insufficiency Animals heterozygous for Col5a1 deficiency do not exhibit cardiac defects but have increased fibrosis in their ventricles and heart valves, suggestive of a role of collagen V in regulating cardiac extracellular matrix during embryonic development.

Two different conditional knockout mice lacking the Col5a1 gene (Col5a1CKO) were generated by using two independent fibroblast Cre drivers and a significant and paradoxical increase in scar size was observed following ischemic injury that was associated with significant worsening of cardiac function. A population genetics approach analyzing gene X trait relationships across approximately 100 in-bred strains of mice following isoproterenol induced cardiac injury also independently demonstrated that the Col5a1 gene is a strong determinant of post injury phenotype vis-a-vis other ECM genes. Following acute ischemic cardiac injury, deficiency of collagen V in scars leads to greater differentiation of fibroblasts to myofibroblasts and significantly higher expression of ECM genes, underlying the increased fibrosis observed in these animals. Collagen V deficient scars demonstrated fibrillar disarray on transmission electron microscopy and altered mechanobiological properties of mutant cardiac fibroblasts and matrix constituting scar tissue. Integrins are mechanosensitive cell surface receptors that respond to mechanical changes in the extracellular environment and affect cellular processes including survival, proliferation and differentiation. Such alterations in scar ultra-structure and mechanical properties are associated with differential expression of αvβ3 and αvβ5 integrins on mutant cardiac fibroblasts creating a permissive environment for augmented myofibroblast formation. Administration of cilengitide, a specific inhibitor of αvβ3 and αvβ5 integrins completely rescued the phenotype of increased post injury scarring, myofibroblast formation and cardiac dysfunction in collagen V deficient animals compared to wild type littermates. These findings provide insight into the physiological role of collagen V in regulating the size of heart scars by modulating integrin signaling. Individuals with classical Ehlers Danlos syndrome (cEDS) harbor mutations in collagen V genes (Col5a1/Col5a2), exhibit phenotypes of dysregulated wound healing with broad scars that lack tensile strength and have altered αvβ3 integrin expression on skin myofibroblasts. These observations on the inhibition of specific integrins to ameliorate dysregulated wound healing in collagen V deficient states may also harbor therapeutic implications for treating aberrant wound healing in cEDS.

The normal response of tissue to injury involves the initiation of a highly coordinated wound repair-programme aimed at restoring normal tissue function. Some of the earliest responses involve the activation of the coagulation cascade, inflammatory cell recruitment and the formation of a provisional matrix to prevent blood loss, infection and promote subsequent wound healing responses Dysregulation of this orchestrated wound repair-response (dysregulated wound healing) can result in pathological scar formation and excessive deposition of collagen and other ECM proteins.

A scar is an area of fibrous tissue that replaces normal skin after an injury. Scars may result from the biological process of wound repair in the skin, as well as in other organs and tissues of the body. Thus, scarring is a natural part of the healing process. With the exception of very minor lesions, every wound (e.g., after accident, disease, or surgery) results in some degree of scaring.

Scar tissue is composed of the same protein (collagen) as the tissue that it replaces, but the fiber composition of the protein is different; instead of a random basketweave formation of the collagen fibers found in normal tissue, in fibrosis the collagen cross-links and forms a pronounced alignment in a single direction. This collagen scar tissue alignment is usually of inferior functional quality to the normal collagen randomised alignment. For example, scars in the skin are less resistant to ultraviolet radiation, and sweat glands and hair follicles do not grow back within, scar tissues A myocardial infarction, commonly known as a heart attack, causes scar formation in the heart muscle, which leads to loss of muscular power and possibly heart failure. The degree of scar burden is an independent driver of prognosis after acute myocardial infarction but little is known about how the wound healing response regulates the size of heart scars. The unappreciated role of collagen V, a fibrillar collagen and a minor structural component of heart scars in regulating the size of heart scars through matrix dependent cues and integrin signaling, was explored. In the absence of collagen V, the cardiac fibroblasts become more compliant and exhibit severe decrease in contractile forces that are necessary for wound contraction, potentially creating a more permissive environment for infarct expansion. The upregulation of mechanosensitive αvβ3 and αvβ5 integrins by collagen V deficient cardiac fibroblasts post injury, likely represents a compensatory response to the disorganized scar architecture and altered biomechanical properties of scar tissue. Although the ligands driving integrin mediated signaling and myofibroblast formation are not obvious, αvβ3 is a promiscuous receptor binding to a large number of ECM proteins and soluble ligands including, osteopontin, vitronectin and fibronectin, several such genes being upregulated in Type V collagen deficient hearts (FIG. 6M); thus many of such ligands could amplify down-stream integrin signaling and myofibroblast differentiation. Notwithstanding the nature of the ligand, the rescue of the phenotype of increased scarring and myofibroblast differentiation in Col5a1CKO animals by the drug cilengitide, that specifically inhibits αvβ3 and αvβ5 integrins, clearly demonstrates the importance of these specific integrins in driving the phenotype. Collagen V in skeletal muscle plays a role in maintaining satellite stem cell quiescence. In this context, collagen V may be mediating a comparable physiologic role in the injured heart by regulating excessive myofibroblast formation.

Increased scar tissue worsens cardiac function and there is a strong correlation between expression of ECM genes and functional cardiac traits such as cardiac contractile function and chamber size. The population genetics data using the HMDP comprising 100 in-bred strains of mice demonstrate that Col5a1 is a key determinant of the strength of the correlation between average ECM gene expression and cardiac traits. This is likely because of the central role that collagen V plays in organization or assembly of collagen I and collagen m fibrils in the matrix. In tissues such as the cornea where collagen V is present in abundance, it is thought to maintain fibrillar arrangement of the matrix that enables functional optical transparency of the cornea. In the absence of collagen V, the entire matrix of the heart scar (that primarily comprises collagen I and III) is disorganized leading to widespread effects on cell and organ function.

These findings could also have implications for Ehlers Danlos syndrome (EDS), a term used to describe a heterogeneous group of connective tissue disorders characterized by abnormalities in skin extensibility, joint hypermobility and tissue fragility Individuals with classical EDS (cEDS) most commonly have mutations in genes encoding for type V collagen (Col5a1,Col5a2) with the most common mutation being haploinsufficient for Col5a1. Although there is scant clinical data on the prognosis of myocardial infarction (MI) and heart scarring in these patients (owing to the relatively rare nature of the disease), patients with cEDS have abnormal mechanical properties of the ECM, exhibit dysregulated wound healing with increased scar size but scars are typically atrophic and have decreased tensile properties, phenotypes consistent with observations in the heart. Moreover, fibroblasts isolated from skin of patients with cEDS demonstrate increased expression of $\alpha v\beta 3$ integrins that is thought to reflect a response to abnormal ECM. These observations confirm the findings of an $\alpha v\beta 3$ mediated activation of myofibroblast differentiation in Co5a1CKO hearts and raise the possibility that inhibitors of specific integrins such as cilengitide may have a role in mitigating dysregulated wound healing in cEDS.

In particular, an inhibitor of $\alpha v\beta 3$ integrin (e.g., cilengitide) shows promise for treating the rare disease classic Ehlers Danlos syndrome (cEDS). Individuals with classic Ehlers Danlos syndrome suffer from exaggerated and aberrant wound healing with increased scarring following injury trauma or surgery. These patients typically have mutations in Col5a1, haploinsufficiency being the most common. They also exhibit up-regulation of the $\alpha v\beta 3$ integrin receptor. The results described herein demonstrate that in preclinical models, cilengitide rescues the phenotype of exaggerated scarring in Col5a1 functional deficiency. The following are representative indications for cilengitide in Ehlers Danlos:

(i) Treatment with cilengitide, e.g., for at least 4 days or even for at least 1 week, prior to scheduled nonemergent surgery and preferably continued for up to 7 days post-surgery until healing of wound has occurred, (ii) Treatment with cilengitide following acute trauma in individuals with cEDS until wound healing has occurred, e.g., for about 7-14 days, (iii) Treatment with cilengitide during labor or childbirth and preferably continued, e.g., for up to 7 days, following childbirth until wound healing has occurred.

In summary, the extracellular matrix plays a critical role in preventing an exaggerated fibrotic repair response of the heart after ischemic injury Fibrillar disarray of the ECM in the absence of collagen V provides matrix dependent cues that drive differential integrin expression, myofibroblast formation and increased expression of ECM genes, and can be viewed as a compensatory physiological response to weakened tensile properties of the scar. The scar size increases but the scar remains disorganized. Our observations illustrate a model of wound healing, where the structural constituents of scar tissue function to limit the size of scar itself.

Non-limiting examples of inhibitors of $\alpha v\beta 3$ integrin are shown in Table 1 below. Non-limiting examples of inhibitors of $\alpha v\beta 35$ integrin are shown in Table 2 below.

TABLE 1

| Non-limiting examples of inhibitors of $\alpha v\beta 3$ integrin. | | |
|---|---|---|
| Target Protein | Compound name (if any) | Other names |
| $\alpha v\beta 3$ integrin | MK-0429 | (3S)-3-(6-methoxypyridin-3-yl)-3-[2-oxo-3-[3-(5,6,7,8-tetrahydro-1,8-naphthyridin-2-yl)propyl]imidazolidin-1-yl]propanoic acid |
| $\alpha v\beta 3$ integrin | SF0166 (SciFluor Life Sciences) | |
| $\alpha v\beta 3$ integrin | SB-267268 | 2-[(4S)-3-Oxo-8-[3-(pyridin-2-ylamino)propoxy]-2-(2,2,2-trifluoroethyl)-4,5-dihydro-1H-2-benzazepin-4-yl]acetic acid |
| $\alpha v\beta 3$ integrin | Bevacizumab (antibody) | |
| $\alpha v\beta 3$ integrin | Intetumumab (antibody) | |
| $\alpha v\beta 3$ integrin | Abciximab (antibody) | |
| $\alpha v\beta 3$ integrin | 17E6 antibody (ab1682) | |
| $\alpha v\beta 3$ integrin | LM-609 (ab190147) | |
| $\alpha v\beta 3$ integrin | Etaracizumab (antibody) | |
| $\alpha v\beta 3$ integrin | Abituzumab (antibody) | |
| $\alpha v\beta 3$ integrin | Vitaxin (antibody) | |
| $\alpha v\beta 3$ integrin | Efatucizumab (antibody) | |
| $\alpha v\beta 3$ integrin | VPI-2690B (antibody) | |
| $\alpha v\beta 3$ integrin | Cilengitide | cyclic Arg-Gly-Asp peptide |
| $\alpha v\beta 3$ integrin | ATN-161 | Ac-PHSCN-NH2 |
| $\alpha v\beta 3$ integrin | SC-68448 | 3-[[2-[[3-(diaminomethylideneamino)benzoyl]amino]acetyl]amino]-3-(3,5-dichlorophenyl)propanoic acid |
| $\alpha v\beta 3$ integrin | SCH221153 | |
| $\alpha v\beta 3$ integrin | s247 | 3-(3-Bromo-5-chloro-2-hydroxyphenyl)-3-[[2-[[5-[(5-hydroxy-1,4,5,6-tetrahydropyrimidin-2-yl)amino]pyridine-3-carbonyl]amino]acetyl]amino]propanoic acid |
| $\alpha v\beta 3$ integrin | P11 | His-Ser-Asp-Val-His-Lys-NH2 |

TABLE 2

Non-limiting examples of inhibitors of αvβ5 integrin.

| Target Protein | Compound name (if any) | Systematic name |
|---|---|---|
| αvβ5 integrin | SB-267268 | 2-[(4S)-3-Oxo-8-[3-(pyridin-2-ylamino)propoxy]-2-(2,2,2-trifluoroethyl)-4,5-dihydro-1H-2-benzazepin-4-yl]acetic acid |
| αvβ5 integrin | Intetumumab (antibody) | |
| αvβ5 integrin | 17E6 antibody (ab1682) | |
| αvβ5 integrin | Abituzumab (antibody) | |
| αvβ5 integrin | Cilengitide | cyclic Arg-Gly-Asp peptide |
| αvβ5 integrin | SCH221153 | |

Definitions

For convenience, certain terms employed in the specification, examples, and appended claims are collected here.

As used herein, the singular forms "a", "an," and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising." The transitional terms "consist" and any grammatical variations thereof, are intended to be limited to the elements stated in the claims and exclude any elements not stated in the claims. The phrases "consisting essentially of" and any grammatical variant thereof indicate that the claim encompasses embodiments containing the specified elements and includes additional elements that do not materially affect the basic and novel characteristic(s) of the claim.

The term "about" or "approximately" means within an acceptable error range for the particular value as determined by one of ordinary skill in the art, which will depend in part on how the value is measured or determined, i.e., the limitations of the measurement system, and the conventional variability accepted in the art for the concerned parameter.

As used herein, the term "administering" means providing a therapeutic agent or composition to a subject, and includes, but is not limited to, administering by a medical professional and self-administering. The means of providing a therapeutic agent are well known to those skilled in the art and include, but are not limited to, oral administration, transdermal administration, administration by inhalation, nasal administration, topical administration, intravaginal administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically, that is, administered to treat an existing disease or condition.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated," for example, if one or more symptoms associated with a particular disease, disorder, or condition are mitigated or eliminated.

The term "preventing" is art-recognized, and when used in relation to a condition is well understood in the art, and includes administration of a composition which reduces the frequency of, or delays the onset of, symptoms of a medical condition in a subject relative to a subject which does not receive the composition. Thus, prevention of scar formation includes, for example, reducing the incidence, number, and/or size of scars in a population of patients receiving a prophylactic treatment relative to an untreated control population, and/or delaying the appearance of scars in a-treated population versus an untreated control population, e.g., by a statistically and/or clinically significant amount.

In certain embodiments, a therapeutic agent may be used alone or conjointly administered with another therapeutic agent. As used herein, the phrase "conjoint administration" refers to any form of administration of two or more different therapeutic agents such that the second agent is administered while the previously administered therapeutic agent is still effective in the body (e.g., the two agents are simultaneously effective in the subject, which may include synergistic effects of the two agents). For example, the different therapeutic agents can be administered either in the same formulation or in separate formulations, either concomitantly or sequentially. In certain embodiments, the different therapeutic agents can be administered within about one hour, about 12 hours, about 24 hours, about 36 hours, about 48 hours, about 72 hours, or about a week of one another. Thus, a subject who receives such treatment can benefit from a combined effect of different therapeutic agents.

In certain embodiments, conjoint administration of the combinations of compounds of the invention with one or more additional therapeutic agent(s) (e.g., one or more additional chemotherapeutic agent(s)) provides improved efficacy relative to each individual administration of the combinations of compounds of the invention or the one or more additional therapeutic agent(s). In certain such embodiments, the conjoint administration provides an additive effect, wherein an additive effect refers to the sum of each of the effects of individual administration of the combinations of compounds of the invention and the one or more additional therapeutic agent(s).

The term "a small molecule" is a compound having a molecular weight of less than 2000 Daltons, preferably less than 1000 Daltons. Typically, a small molecule therapeutic is an organic compound that may help regulate a biological process.

"Subject" refers to an animal, such as a mammal, for example a human. The methods described herein can be useful in both humans and non-human animals. In some embodiments, the subject is a mammal (such as an animal model of disease), and in some embodiments, the subject is human.

The term "activator" refers to a compound having the ability to activate a biological function of a target biomolecule, for example, an mRNA or a protein, whether by increasing the activity or expression of the target biomolecule. Accordingly, the term "activator" is defined in the context of the biological role of the target biomolecule. The term "agonist" refers to a compound that binds to a receptor and activates the receptor to produce a biological response.

The term "inhibitor" refers to a compound having the ability to inhibit a biological function of a target biomolecule, for example, an mRNA or a protein, whether by decreasing the activity or expression of the target biomolecule. The term "antagonist" refers to a compound that binds to a receptor, and blocks or dampens the receptor's biological response. The term "inhibitor" may also refer to an "antagonist."

Pharmaceutical Compostions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, the combination of compounds described herein (e.g., an inhibitor of αvβ3 integrin and an inhibitor of αvβ5 integrin) and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In certain embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration.

The composition can also be present as a non-absorbable composition to block serotonin production at its source rather than by pharmacologically blocking its systemic effects. The use of a non-absorbable composition will likely have minimal adverse effect.

A pharmaceutically acceptable carrier can contain physiologically acceptable agents that act, for example, to stabilize, increase solubility or to increase the absorption of a compound present in the combinations of compounds described herein. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a combination of compounds of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include. (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually), anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The combinations of compounds described herein can also be formulated for inhalation. In certain embodiments, the combination of compounds described herein can be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound in the combinations of compounds described herein, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a tale, calcium stearate, magnesium stearate, solid polyethylene glycols, sodium lauryl sulfate, and mixtures thereof; (10) complexing agents, such as, modified and unmodified cyclodextrins; and (i) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in United States patent application publications 20050080056, 20050059744, 20050031697 and 2005004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue. For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied to obtain an amount of the active ingredient that is effective to achieve the desired therapeutic response for a particular patient, composition, and mode of administration, without being toxic to the patient.

The selected dosage level will depend upon a variety of factors including the activity of the particular combination of compounds employed, or the ester, salt or amide thereof, the route of administration, the time of administration, the rate of excretion of the particular compounds being employed, the duration of the treatment, other drugs, compounds and/or materials used in combination with the particular compounds employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed, 1814-1882, herein incorporated by reference).

In general, a suitable daily dose of active compounds used in the compositions and methods of the invention will be that amount of the compounds that is the lowest dose effective to produce a therapeutic effect. Such an effective dose will generally depend upon the factors described above.

If desired, the effective daily dose of the active compounds may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (ED A), sorbitol, tartaric acid, phosphoric acid, and the like.

Methods of Treatment

Provided herein are methods of inhibiting integrin (e.g., αvβ3 integrin o αvβ5 integrin) in a cell comprising contacting the cell with an inhibitor of integrin (eg, αvβ3 integrin inhibitor or αvβ5 integrin inhibitor), optionally conjointly with another integrin inhibitor. In certain embodiments, contacting the cell occurs in a subject in need thereof, thereby treating a dysregulated wound healing, reducing scar formation, and/or improving wound healing. In some embodiments, the subject has Ehlers Danlos Syndrome and/or acute myocardial infarction.

Methods of Diagnosis:

Provided herein are methods of measuring Col5a1 levels as a diagnostic test to determine prognosis after heart attack (myocardial infarction). Col5a1 deficiency decreases cardiac function after acute myocardial infarction in a dose dependent manner (i.e. the lower the Col5a1 expression, the worse are cardiovascular outcomes). A preclinical model of heart failure in 100 strains of mice where each strain expresses different levels of cardiac injury confirms these observations. In this model, the level of Col5a1 expression strongly correlates with cardiac outcomes. Therefore, determining Col5a1 levels or expression in humans after acute heart attacks may be used to determine the prognosis after a heart attack. For example, Col5a1 may be measured in macrophages isolated from peripheral blood and a PCR-based analysis may be performed to determine Col5a1 expression levels. This test to determine Col5a1 expression serves as a new diagnostic marker to prognosticate future or subsequent heart attacks. This test to determine Col5a1 expression also serves as prognosis tool after ischemia, acute kidney, or liver injury or stroke.

EXAMPLES

The invention now being generally described, it will be more readily understood by reference to the following examples, which are included merely for purposes of illustration of certain aspects and embodiments of the present invention, and are not intended to limit the invention.

Example 1: Materials and Methods

Antibodies and Probes

The following primary antibodies, reagents, or probes were used for immunostaining: rabbit anti-Vimentin (1:100, Abcam, ab45939); mouse anti-smooth muscle actin (1:100, Dako, M01851); anti-cardiac Troponin I (1:100, Abcam, ab47003); mouse anti-integrin αVβ3 (1:50, Abcam, ab7166); mouse integrin αVβ5 (1:20, R&D, MAB2528); Alexa Fluor 594 conjugated WGA (5 μg/ml, Invitrogen, W11262). For dual RNA-FISH/immunostaining: rabbit anti-RFP (1:50, Rockland, 600-401-379). For flow cytometry: rabbit anti-integrin αVβ3 (CD51/CD61) (1:100, ThermoFisher, MA5-32195); rabbit anti-integrin αVβ5 (1:30, Bioss, bs-1356R); PE-conjugated rat anti-integrin αV (1:20, Invitrogen, 12-0512-82), PE-conjugated rat anti-integrin β1 (1:20, Invitrogen, 12-0181-82); PE-conjugated american hamster anti-integrin β2 (1:20, Invitrogen, 12-0291-82); PE-conjugated rat anti-integrin α5 (1:100, BioLegend, 103805); PE-conjugated rat IgG isotype control (same dilution for target antibody, BioLegend, 400508), For RNA-FISH: mouse Col1a1-C1 probe (1:50, ACD, 319371); mouse Col3a1-C2 probe (1:50, ACD, 455771-C2); mouse Col5a1-C3 probe (1:50, ACD, 52129143).

Murine models of acute ischemic cardiac injury

All animal studies were approved by the Animal Research Committee, University of California, Los Angeles, Myocardial infarction was performed by ligating the left anterior descending (LAD) coronary artery following open thoracotomy. Briefly, Mice were anesthetized with ketamine (80 mg/kg)/xylazine (20 mg/kg) by intraperitoneal injection. Respiration was provided by mechanical ventilation with 95% 02 (tidal volume 0.5 ml, 130 breaths/min). The LAD coronary artery was ligated intramurally 2 mm from its origin with a 9-0 proline suture.

For experiments related to use of cilengitide, 20 mg/kg of Cilengitide diluted in PBS was administered by intraperitoneal injection every day until harvest and PBS was used as vehicle as a control.

For echocardiography, animals were continuously anesthetized with 1.5% isoflurane and 95% O2, Vevo2100 imaging system and a 30-mHz scan head (Toronto, Canada) were used to acquire short/long axis B-mode and M-mode images. Long axis B-mode view was used for analyzing peak longitudinal strain rate. All measurements and calculations were conducted using Vevo2100 software.

Bulk RNA-Seq, Single-Cell RNA-Seq and qPCR

For bulk RNA-seq, the injured and uninjured regions of the heart were harvested at different time points following injury, total RNA extracted using RNeasy Mini kit (Qiagen) and used to generate RNA-Seq libraries followed by sequencing using Illumina 4000 platform (single-end, 65 bp). Reads were aligned to the mouse reference genome (mm10) using STAR aligner, and used to quantify normalized expression values (RPKM) for annotated genes (Ensembl v.86). RPKM values were used for principal component analysis (PCA) and gene expression visualizations. Differential expression analysis was performed using edgeR quasi-likelihood pipeline. Differential expressed genes (DEGs) were identified at FDR 1% and minimum fold-change value of 4.

For sc- RN A-seg, wk post MI hearts were harvested and digested by liberase as described later. After digestion, cells were incubated with 10 µM Calcein AM (Abcam, ab141420) and flow sorted to identify live cells followed by library preparation. Library was generated by Chromium™ Single Cell 3' Library Construction (10× Genomics) and sequenced by Illumina NextSeq 500 Sequencing System. After sequencing, fastq files were generated using Cellranger mkfastq (version 3.0.2). The raw reads were mapped to human reference genome (refdata-cellranger-mm 10-30.0) using cellranger count. Digital expression matrix was extracted from the filtered feature be matrix folder outputted b the cell ranger count pipeline. Multiple samples were aggregated by cellranger aggr. To identify different cell types and find signature genes for each cell type, the R package Seurat (version 3.0.2) was used to analyze the digital expression matrix. Cells with less than 500 unique molecular identifiers (UMIs) or less than 100 genes, or greater than 50% mitochondrial expression were removed, resulting in a final dataset of 17,826 cells and 21,447 genes for further analysis. The Seurat function NormalizeData was used to normalize the raw counts. Variable genes were identified using the FindVariableFeatures function. The ScaleData function was used to scale and center expression values in the dataset, the n tuber of unique molecular identifiers (UMI) was regressed against each gene. Principal component analysis (PCA) t-distributed stochastic neighbor embedding (tSNE), and uniform manifold approximation and projection (UMAP) were used to reduce the dimensions of the data, and the first 2 dimensions were used in the plots. The FindClusters function was sued cluster the cells. Marker genes were found using the FindAllMarkers function for each cluster. Cell types were annotated based on the marker genes and their match to canonical markers.

For qPCR, and RNA-seq, the injured and uninjured regions of the heart were harvested at different time points following injury, RNA extracted using RNeasy Mini kit (Qiagen). cDNAs were generated using iScript cDNA Synthesis Kit (BioRad) and qPCR performed.

Col5a1 Correlation with Extracellular Matrix Pathway Accounts for Clinical Trait Association in the HMDP The data used for analysis, including left ventricle expression arrays and clinical traits can be found using the GEO accession: GSE48760 and within the following studies. Midweight bicorrelation coefficients and corresponding p-values were generated from HMDP data using the R package WGGNA. To calculate adjusted regressions using the same approaches and compare directly, residuals from each ECM gene correlated with Col5a1 were extracted from the regression using the base lm( ) function in R. These residuals were then correlated against indicated traits also using WGCNA to enable direct comparisons. Distributions of p-values were compared using a students t-test (two-way), Proteomic Analysis of Scar Tissue Injured and uninjured regions of the mouse heart at Day 7 following injury were dissected and homogenized in lysis buffer (200 uL, 12 mM sodium lauroyl sarcosine, 0.5% sodium deoxycholate, 50 mM triethylammonium bicarbonate (TEAB)), Sigma Protease Inhibitor Cocktail (0.89 mg/mL final concentration)), then subjected to bath sonication (10 min, Bioruptor Pico, Diagenode Inc, (Denville, NJ)) and heated (95° C., 5 min). An aliquot of the resulting solution (9 uL) was taken for measurement of total protein concentration (bicinchoninic acid assay; Micro BCA Protein Assay Kit, Thermo Fisher Scientific, Waltham, MA, using ISA as a standard). The remaining samples were diluted to 0.5 mg protein/mL with lysis buffer, and an aliquot of each (100 uL) was treated with tris(2-carboxyethyl) phosphine (10 uL, 55 mM in 50 mM TEAB, 30 min, 37° C.) followed by treatment with chloroacetamide (10 uL, 120 mM in 50 mM TEAB, 30 min, 25° C. in the dark). They were then diluted 5-fold with aqueous 50 mM TEAB, and incubated overnight with Sequencing Grade Modified Trypsin (1 ug in 10 µL of 50 mM TEAB; Promega, Madison, WI) following which an equal volume of ethyl acetate/trifluoroacetic acid (TFA, 100/1, v/v) was added. After vigorous mixing (5 min) and centrifugation (13,000×g, 5 min), the supernatants were discarded and the lower phases were dried in a centrifugal vacuum concentrator. The samples were then desalted using a modified version of Rappsilber's protocol in which the dried samples were reconstituted in acetonitrile/water/TFA (solvent A, 100 uL, 2/98/0.1, v/v/v) and then loaded onto a small portion of a C18-silica disk (3M, Maplewood, MN) placed in a 200 uL pipette tip. Prior to sample loading the C18 disk was prepared by sequential treatment with methanol (20 uL), acetonitrile/water/TFA (solvent B, 20 uL, 80/20/0.1, v/v/v) and finally with solvent A (20 uL). After loading the sample, the disc was washed with solvent A (20 uL, eluent discarded) and eluted with solvent B (40 uL). The collected eluent was dried in a centrifugal vacuum concentrator. The samples were then chemically modified using a TMT10plex Isobaric Label Reagent Set (Thermo Fisher Scientific) as per the manufacturer's protocol. The TMT-labeled peptides were dried and reconstituted in solvent A (50 uL), and an aliquot (2 uL) was taken for measurement of total peptide concentration (Pierce Quantitative Colorimetric Peptide, Thermo Fisher Scientific). The samples were then pooled according to protein content (10 ug of peptide from each sample: 100 ug total), and desalted using the modified Rappsilber's protocol described above. The dried multiplexed pooled sample was reconstituted in water/acetonitrile with 10 mM ammonium bicarbonate (solvent C, 5 uL, 98/2, v/v, pH10) prior to fractionation (2.7 uL injection) via high pH reversed-phase chromatography using a 1260 Infinity LC System (Agilent Technologies, Santa Clara, CA) and a ZORBAX 300 Extend-C18 column (Agilent Technologies, 0.3×150 mm, 3.5 µm) equilibrated in solvent C and eluted (6 uL/min) with an increasing concentration of solvent D (acetonitrile/water with 10 mM ammonium bicarbonate, 80/20, v/v, pH10: min/% D; 0/0, 5/14, 65/60, 75/0, 95/0). The fractions were eluted into a 96-well plate with 20 uL of 5% formic acid (FA) in each well over the course of 68 minutes. The 96 fractions were then condensed into 12 fractions prior to another desalting again using the modified Rappsilber's protocol described above. The eluants were then dried and reconstituted in water/acetonitrile/FA (solvent E, 10 uL, 98/2/0.1, v/v/v), and aliquots (5 uL) were injected onto a reverse phase nanobore HPLC column (AcuTech Scientific, C18, 1.8 um particle size, 360 um×20 cm, 150 um ID), equilibrated in solvent E and eluted (500 nL/min) with an increasing concentration of solvent F (acetonitrile/water/FA, 98/2/0.1, v/v/v: min/% F; 0/0, 5/3, 18/7, 74/12, 144/24, 153/27, 162/40, 164/80, 174/80, 176/0, 180/0) using an Eksigent NanoLC-2D system (Sciex (Framing ham, MA). The effluent from the column was directed to a nanospray ionization source connected to a hybrid quadrupole-Orbitrap mass spectrometer (Q Exactive Plus, Thermo Fisher Scientific) acquiring mass spectra in a data-dependent mode alternating between a full scan (m/z 350-1700, automated gain control (AGC) target $3×10^6$, 50 ins maximum injection time, FWHM resolution 70,000 at m/z 200) and up to 10 MS/MS scans (quadrupole isolation of charge states≥2, isolation width 1 2 Th) with previously optimized fragmentation conditions (normalized collision energy of 32, dynamic exclusion of 30 s, AGC target $1×10^5$, 100 ins maximum injection time, FWHM resolution 35,000 at m/z 200). The raw data was analyzed in Proteome Discoverer 2.2, which provided measurements of relative abundance of the identified peptides Histological Studies Hearts were harvested under anesthesia and perfused with PBS followed by fixation in 4% formaldehyde in PBS at 4'C for 24 h, and subsequently subjected to dehydration in sucrose solution. Then the hearts were embedded in Tissue-Tek O.C.T compound (SAKURA, Finetek, USA) and sectioned with 10 μm-thickness.

For immunostaining, tissue sections were incubated with pre-chilled acetone at −20° C. for 10 min, blocked in 10% species-specific normal serum in 1% BSA/PBS for 1 h, and primary antibodies diluted in 1% BSA/PBS at 4° C. overnight. Secondary antibodies were diluted in PBS and incubated with the sections for 1 h. Samples were counterstained with DAPI (1 μg/mL, invitrogen, D3571) and mounted with SlowFade Gold Antifade reagent (Invitragen, S36936). Images were taken using Nikon Eclipse Ti2 confocal microscopy (Nikon, USA) and analyzed in NIS Element AR software (Nikon). For detection of αsmooth muscle actin, integrin αVβ3, and αVα5, M.O.M immunodetection kit (Vector) was used. Briefly, tissue sections were incubated with pre-chilled acetone at −20'C for 10 min, incubated with Avidin/Biotin blocking buffer (Vector) for 15 min, M.O.M blocking buffer for 1 h, and primary antibodies diluted in M.O.M diluent at 4° C. overnight. Biotinylated 2nd antibody against mouse (Vector) was diluted in M.O.M diluent (1:250) and incubated with the sections for 10 min. Samples were incubated with diluted fluorescein avidin DCS (1:60) for 5 min. Samples were counterstained with DAPI (1 μg/mL, Invitrogen, D3571) and mounted with SlowFade Gold Antifade reagent (Invitrogen, S36936).

For Masson Trichrome staining, sections were stained using Masson Trichrome Stain kit (Thermo Scientific, 87019). Images were taken in heart sections from apex, mid-ventricle, and close to suture and fibrotic area analyzed from apex to mid-ventricle. Scar tissue area was calculated as the fraction of left ventricular surface area occupied by the scar tissue. Severity of fibrosis was classified as sample showed >40% fibrotic area as "severe", 20-40% as "moderate" or <20% as "mild" for 6 wks post MI hearts and >50% fibrotic area as "severe", 30-50'% as "moderate", or <30% as "mild" for 2 wks post MI hearts.

RNA-Fluorescence In Situ Hybridization.

RNA-FISH was performed using RNAscope Multiplex Fluorescent reagent kit v2 (ACD Inc, USA) as per manufacturer instructions. Tissue sections were incubated with hydrogen peroxide for 15 minutes followed by incubation with RNAscope Target Retrieval Reagent at 99° C. for 5 minutes. Then the section was incubated with Protease III reagent at 40° C. for 30 minutes in HybEZ II oven (ACDInc). After pre-treatment steps, RNAscope probes were hybridized at 40° C. for 2 h, AMP1 for 30 mint, AMP2 for 30 mini, AMP3 for 15 min, channel-specific HRP reagent for 1.5 min, diluted TSA Plus fluorophores (PerkinElmer, USA) in RNAscope TSA dilution buffer (1:1000 dilution) for 30 min, HRP-blocker reagent for 15 min. Stained section was counterstained with DAPI solution and mounted in SlowFade Gold Antifade reagent (Invitrogen, S36936).

For dual RNA-FISH and immunostaining, tissue sections were pre-treated, and signals developed as described above. Following RNA-FISH, the sections were blocked with 10% normal goat serum/1% BSA in PBS, incubated with anti-RFP (1:50, Rockland, 600-401-379) or anti-cTnI (1:50, Abcam, ab47003) at 4° overnight, HRP-conjugated secondary antibodies against rabbit (1:200, Invitrogen, #31470) for 30 mii, diluted TSA Plus TMR (1:300, PerkinElmer, FYP1169) in RNAscope TSA buffer for 15 min, and counterstained with DAPI.

Generation of Animals with Genetically Labeled Cardiac Fibroblasts and Fibroblast Specific Deletion of Col5a1.

Colla2CreERT and TCE21MerCreMer animals were crossed with the lineage reporter Rosa26tdtomato animals to generate progeny animals. Tamoxifen was administered for 10 days prior to ischemic cardiac injury followed by RNA-FISH to determine whether genetically labeled fibroblasts co-expressed the RNA signal. For generation of Col5a1CKO mice, Colla2CreERT or TCF21MerCreMter mice were crossed with the Col5a1 floxed mice and progeny mice were administered tamoxifen (1 mg IP daily) for 5 days prior to ischemic injury and continued for 7 days following injury. For the experiment on Col5a1 deletion timing, TCF21 MerCreMer mice crossed with the Col5a1 floxed mice were administered tamoxifen from 4 days to 14 days post injury.

Insoluble Collagen Assay

Insoluble collagen assay was conducted using Sircol Insoluble Collagen Assay Kit (Biocolor, S2000). The injured regions of the heart were harvested at 4 weeks following injury and weight their wet weight Tissues were homogenized in 0.1 mg/ml pepsin/0.5M acetic acid and incubated overnight at 40'C. Lysates were centrifuged at 12K r.p.m for 10 min and supernatants were transferred to new tubes. Tissue residues were incubated with Fragmentation Reagent at 65° C. for 2 h with vortex every 30 min during incubation, centrifuged at 12K r.p.m for 10 min, and supernatants were transferred into new tubes. Supernatants were mixed with 1 ml of Sircol Dye Reagent and incubated for 30 min with gentle shaking. Precipitates were collected by centrifuge at 12K r.p.m for 10 min and washed with 750 μl of ice-cold Acid-Salt Wash Reagent. Washed precipitates were dissolved in 500 μl of Alkali Reagent, transferred 200 μl of each sample and collagen standards into a 96-well plate, and measured absorbance at 0.55 nm using Synergy H1 microplate reader (BioTeK), Transmission Electron Microscopy Samples were fixed in 2% glutaraldehyde in PBS at 4° C. for 3 hour. Fixed samples were embedded in low-viscosity resin (Agar, UK) as following: samples were osmicated using 1% OsO4; stained with 3% uranyl-acetate; dehydrated in 30-50-70-95-100% ethanol and embedded in low-viscosity resin (Agar, UK). Plastic-embedded samples were sectioned using UCT ultramicrotome (Leica, Austria) and diamond knife (Diatome, Austria). Sections 50-55 nm thick were mounted on home-made EM grid(s) with plastic-carbon support film, stained with saturated uranyl-acetate and Sato's lead-citrate. Sections were imaged using JEM1200EX transmission electron microscope (JEOL, Japan) at 80 kV equipped with BioScanr600W digital camera (Gatan, USA). Images were prepared for publication using a Photoshop (Adobe, USA).

Tomography of Collagen Fibers

Sections 200 nm thick were mounted on 150 mesh hexagonal copper grids (Ted Pella, USA). Thereafter, grids with attached sections were stained with saturated uranyl acetate, lead citrate, 10 nm gold from both sides. Layer of carbon was evaporated on top of the section. Grids were loaded into high-resolution tomography holder Model 20:20 (Fischione, ISA) and imaged with TF20 TEM (FEI, Netherlands) at 200 kV. To collect tomogram, FET Batch Tomography software was used. The tomograms were processed using IMOD software. Alignment of the stack was performed using fiducial markers (10 nm gold) on both sides of the tomogram. The final 3d model calculation was performed by SIRT (IMOD). Obtained 3d models were visualized in Chimera. They were filtered with Gaussian filter and segmented in Segger, part of Chimera package. Final models were imaged in Chimera also.

Plasmid Construction and Lentivirus Preparation pLenti-Largen T antigen (Cat #18922), Lenti-pHIV-eGFP (Cat#21373), PSPAX2 (Cat#12260), PMD.G2 (Cat#12259), pLV-eGFP-Cre (Cat#86805) were purchased from Addgene. Total 13 ug pasmids (object gene, PSPAX2, PMD.G2) was co-transfected into 75 cm² flask with 293T cells in 10 ml DMEM Medium, 6-7 ml fresh DMENM medium were changed after plasmids co-transfected 8-10 h. The medium was collected and centrifuged at 4° C. in 500× g for 10 min after transfected 72 h. The medium with virus was aliquoted and stored at −80° C.

Isolation of Primary Culture Adult Cardiac Fibroblast 5-7 hearts were harvested from wild-type C57B1/6 mice or Col5a1 floxed mice. Valves and atriums were removed from the hearts, and the hearts rinsed in ice-cold HBSS. The hearts were chopped into 1 mm square pieces, suspended in 0.1 μg/ml liberase TH (Sigma, 5401151001) in Tyrodes buffer (136 mM NaCl, 5.4 mM KCl, 0.33 mM $NaH_2PO_4$, 1 mM $MgC_2$, 10 mM HEPES, 0.18% Glucose), and incubated with shaking incubator at 37° C. for 30 min at 80 rpm. Digested hearts were filtered with a 40 μm cell strainer (Fisher, 22363547), centrifuged at 200× g for 5 min, resuspended cells with 10 ml of 20% FBS in F12K medium, and seeded the cells into 100 mm² dish. After 2 h, medium was changed to human basic FGF (10 ng/ml, Millipore, GF003) containing 20% FBS in F12K medium Isolated cardiac fibroblast was used for experiments in $2^{nd}$ or $3^{rd}$ passage.

Generation of Col5a1 Deficient Immortalized Cardiac Fibroblast

Cardiac fibroblasts were isolated from Col5a1 fl/fl mouse as described above. These cells were infected with Lentivirus-Large T antigen in presence of polybrene (8 μg/ml) for 16 h, treated with puromycin (2 μg/ml) for selection of infected cells. Immortalized cells were cultured with 10% FBS containing high glucose DMEM. Cells so immortalized were then infected with Lentivirus-Cre recombinase or lentivirus-GFP to generate Col5a1 deficient cardiac fibroblast or control cardiac fibroblast, respectively. These cells were cultured for 6-7 days and used for each experiment to determine effects on gene expression. To determine an effect of Cilengitide on these cells, Col5a1fl/fl cardiac fibroblasts were pretreated with Cilengitide (1 μM) in 10% FBS containing high glucose DMEM for 1 h before infection with lentivirus-Cre recombinase or lentivirus-GFP. These cells were treated with Cilengitide/vehicle for 7 days and medium was changed every 2 days.

Flow Cytometry

For cultured cardiac fibroblasts, cells were harvested and fixed in 4% formaldehyde/PBS for 10 min on ice, incubated for primary antibodies diluted in 1%BSA/PBS for 1 h on ice. For unconjugated antibodies, cells were incubated with diluted Alex Fluor 594 secondary antibody (1:200, Invitrogen). Data was analyzed using Flowjo software.

Measurement of Force Generated by Col V Deficient Cardiac Fibroblasts.

Device Fabrication

Figure 9A:
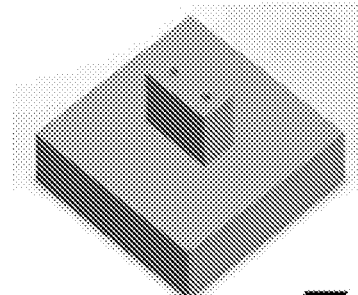
FIGS. 9A-9E show fabrication process of PDMS platform wells and two microposts to make microtissues.
Figure 9B:
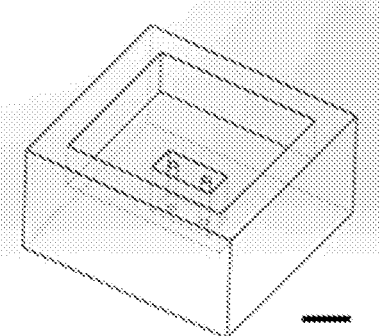
Figure 9C:
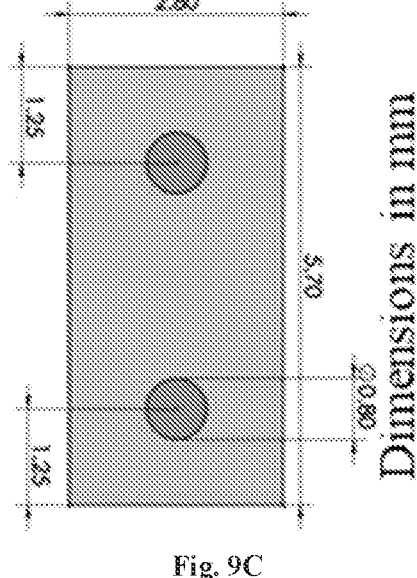
Figure 9D:
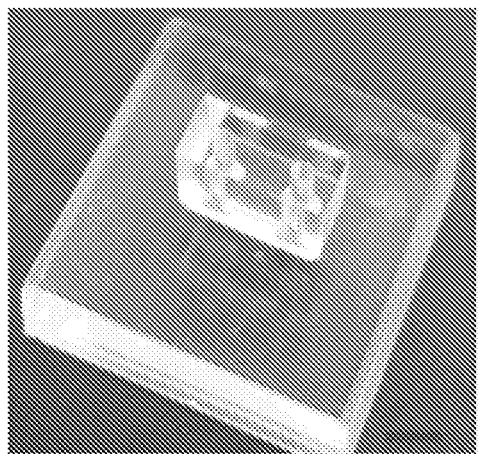
Figure 9E:
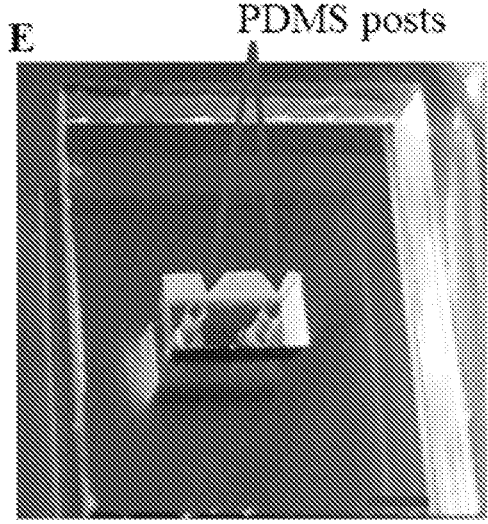

The device to make microtissues was designed using AutoCAD software (Autodesk Inc., USA). FIG. 9A shows the three-dimensional (3D) design of master mold. FIG. 9B shows the 3D schematic of the replicated design with wells and two microposts. The top view of the replicated design is shown in FIG. 9C. By using a laser cutter with a fine-tuned laser power and speed, poly(methyl methacrylate) (PMMA) master molds were fabricated as shown in FIG. 9D. After sticking the mold to a Petri dish with glue, a mixture of polydimethylsiloxane (PDMS) prepolymer and its curing agent with the mass ratio of 20:1 was prepared and poured on the Mold. After removing bubbles and curing at 80° C. for 2 hours, the PDMS was peeled off from the mold as shown in FIG. 9E.

Fabrication of Microtissues

In order to make microtissues, after sterilizing the PDMS platform, a collagen hydrogel at density of 3 mg/ml was prepared. Cardiac fibroblasts were mixed with the gel at density of 5 Million cells/ml. The small well around microposts was filled with the cell-laden gel and then incubated for 1 hour to encourage the gel formation. After the incubation, sufficient cell culture media was added to the samples.

Measurement of Contraction Force of Microtissues

Figure 10:
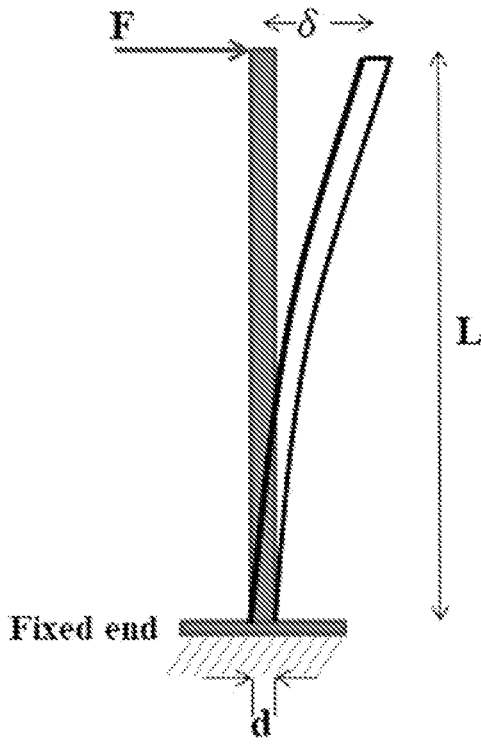
FIG. 10 shows schematic for cantilever beam deflection.

The pictures of tissues were taken on days 1, 2, and 3 of culture by using ToupView microscope integrated with SeBaView software. The images were then analyzed with ImageJ software to measure the deflection of microposts due to the tissue contraction. The cantilever beam theory was used to quantify tissue force. This theory correlates the tissue force to small deflection of microposts as shown in FIG. 10. The stiffness of microposts can be calculated by equation (1) and the contraction force can be calculated by equation (2) by measuring the deflection of the free end of each nmicropost as follows:

$$k = \frac{3\pi E d^4}{64L^3} \tag{1}$$

$$F = k\delta \tag{2}$$

where k is the stiffness of each micropost that is a function of length (L), diameter (d), and Young's modulus of PDMS post (E) The Young's modulus of PDMS was considered to be 1.1 MPa. In the equation (2), F is the contraction force, 8 is the deflection of free end of the micropost.

Numerical Simulation

To confirm the measurements of PDMS deflection and contraction force, finite element analysis (FEA) implemented in COMSOL Multiphysics 5.3 software was used. The PEM model consisted of two cylindrical PDMS microposts with the post height of 3.1 mm and diameter of 0.8 mm inside a well. The microposts were fixed to the well and deemed as a cantilever beam. The PDMS assembly was modeled as linear elastic material with a uniform Young's modulus of 1.1, MPa, After setting appropriate boundary conditions and by applying a single force to the free end of the microposts, the displacement distribution of the microposts were determined as illustrated in FIG. 11A. Moreover, the simulation showed a linear relationship between the applied force and micropost deflection, which is in agreement with the cantilever beam theory (FIG. 11B).

Measurement of Cell Stiffness of Col V Deficient Cardiac Fibroblasts.

Quantitative phase microscopy (QPM) was used to determine cell stiffness as follows Cardiac fibroblasts were isolated from Col5a1 floxed mice, immortalized and then treated with a Cre expressing or GFP lentivirus to generate Col5a1CKO or control fibroblasts. Cells were imaged every 5 min for 20 h at 20× with a SID-4 Bio (Phasics) camera to acquire QPM data via quadriwave lateral shearing interferometry. This was on an Axio-vision Observer Z1 (Zeiss) equipped 0.4 numerical aperture objective lens with illumination was provided by a 660 nm center wavelength collimated LED (Thorlabs). The Col5a1CKO fibroblasts and the control fibroblasts were imaged with enough spacing between cells to allow for automated particle tracking and cell or cell cluster segmentation. Automated detection of cell division events were done by pattern matching of quantitative phase images. Using experimentally determined cell average specific refractive index, quantitative phase shifts is related to the dry biomass of cells. All image processing was performed using custom MATLAB (MathWorks) scripts.

OPM Stiffness Via Temporal Autocorrelation

We quantified the rate of biomass redistribution by examining the similarity of the QPM data over time through an unbiased estimate of autocorrelation of the phase shift signal. The temporal autocorrelation was normalized with respect to the number of data points used in each autocorrelation window, referenced to the end of the time shift window ($t_0$), and defined as:

$$C_{ff}(x, y, t_0, t) = \frac{w}{\left(w - \frac{t}{Dt}\right)} \cdot \frac{\sum_{i=0}^{w-i/Dt} f(x, y, t_0 - iDt) \cdot f(x, y, t_0 - iDt - t)}{\sum_{i=0}^{w} [f(x, y, t_0 - iDt)]^2} \quad (1)$$

Where x and y are the spatial positions after removing rigid translational motion of the cell cluster, $t_0$ is the time, $\phi$ is phase shift, w is the number of images used to calculate the signal, and $\tau$ is time lag. The autocorrelation was then averaged over the cell or cluster area as:

$$\overline{Cff(t_0, t)} = \frac{1}{A} \sum_{all\, x,y\, in\, A} C_{ff}(x, y, t_0, t) \quad (1)$$

where A is the area of the cell or cluster in pixels. The slope of a linear least-squares fit to the averaged autocorrelation from $\tau=0$ to $\tau=1$ h (12 frames) was defined as the decorrelation rate and used to quantify the biomass redistribution rate within cell clusters. Any decorrelation rate measurements that included images with mitotic cells were excluded. The decorrelation rate was then matched on a standard curve of known decorrelation rate vs. AFM stiffness to approximate a QPM stiffness value Force Measurement of Neonatal Rat Ventricle Myocyte and Fibroblast Co-Culture.

Fabrication of Bio-Sensor Devices

Figure 12B:
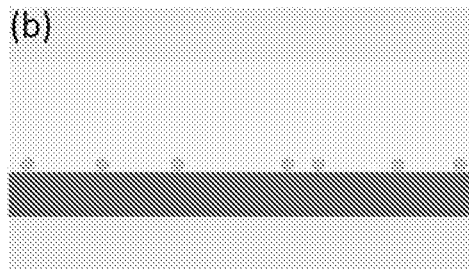
Figure 12C:
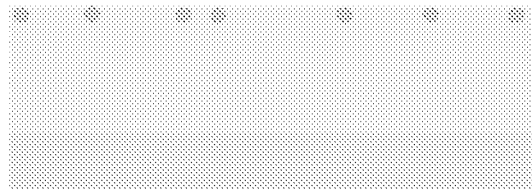

The bio-sensor devices were fabricated by first spin coating a layer of photoresist (AZ 4620, 2500 rpm, 60s) onto a glass slide, and baking it at 90 Celsius for 3 minutes. Then, gold nanoparticles suspended in citrate buffer (Sigma-Alrich 742090) were deposited onto the photoresist and left to dry in a vacuum desiccator (Thermo Scientific™ 53100250) overnight, as illustrated in FIG. 12A. A mixture of polydimethylsiloxane (PDMS) comprising 1 part of Sylgard 184 (Dow Corning) with 6 parts of Sylgard 527 (Dow Corning) was then poured onto the surface of dried gold nanoparticles. The Sylgard mixture was put under vacuum to remove the air bubbles before a coverslip glass was put on top of it, as shown in FIG. 12B The devices were then left to cure in the oven at 60 Celsius for 12 hours. Thereafter, the devices were released by immersing them into acetone overnight to dissolve the photoresist. This reveals the final structure shown in FIG. 12C.

Cell Seeding and Microscopy

Matrigel (at concentration of 83 µg/mL) was then coated for 12 hours on the surface of the PDMS devices. On day 1, neonatal rat ventricular cardiomyocytes (NRVMs) were seeded at 75% confluence on the devices for the mutant group, and at 90% confluence on the devices for the control group. The confluence in the 2 groups was made different in order to account for the fact that each mutant fibroblast occupies 3 times more area than each control fibroblast. On day 2, control and mutant fibroblasts were separately seeded onto their respective devices. On day 3, the cells were stained with Calcein AM (invitrogen™), before they were imaged under dark field and fluorescence microscopy (Zeiss AxioScope A1, EC Epiplan-Neofluar, 20×, N.A.=0.5). The gold nanoparticles were also imaged under dark field microscopy. The gold nanoparticles moved when the cells were beating, due to the mechanical coupling between the cells and the substrate.

Machine Learning Model

Figure 13A:
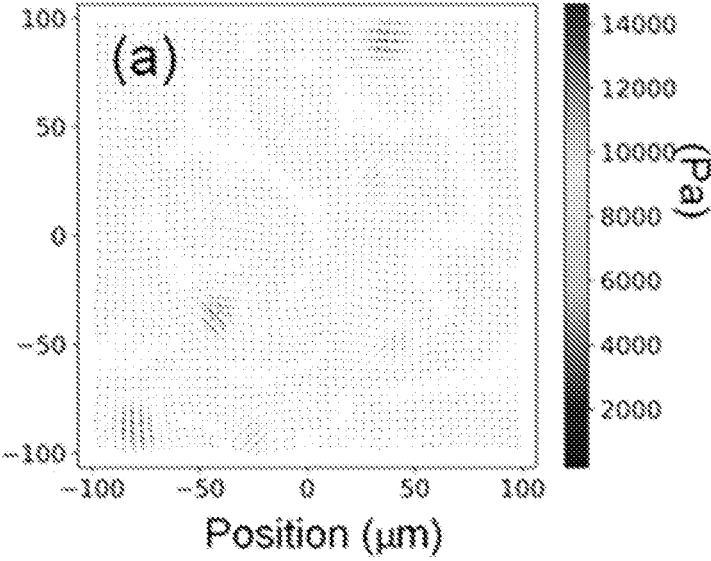
FIGS. 13A-13B shows an example of stress distribution and displacement.
Figure 13B:
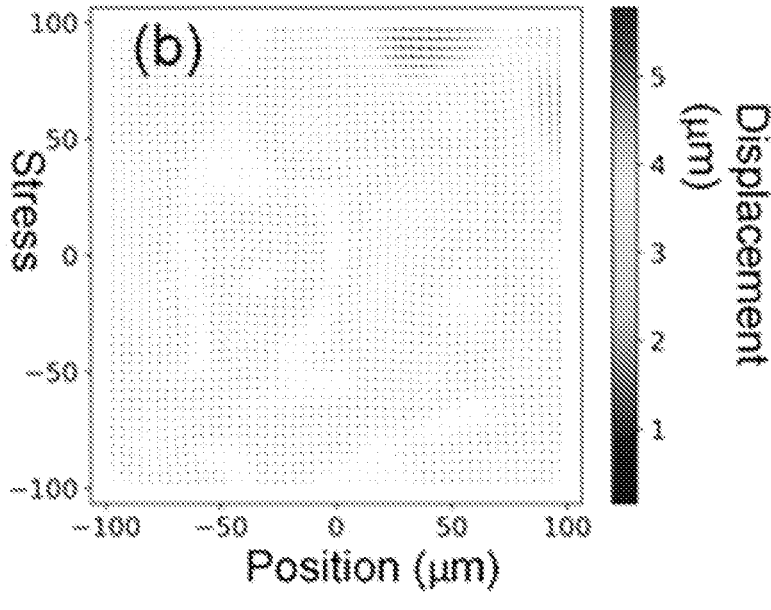

Before we could process the images obtained from microscopy, the numerical model needed to be built. The numerical model was built by first generating 1000 different random continuous stress distributions in COMSOL (finite element software) by using 2-dimensional random functions. An example of the stress distribution is shown in FIG. 13A. The stress distributions were applied as boundary loads onto the top surface of the device in COMSOL. Stationary studies were done in COMSOL to solve for the equilibrium displacement of the PDMS surface. One example of the displacement of the PDMS surface is shown in FIG. 13B. Thereafter, the 1000 different cases of stresses and displacements were used to train the linear regression machine learning model (scikit-learn).

Processing of Experimental Images

Figure 14A:
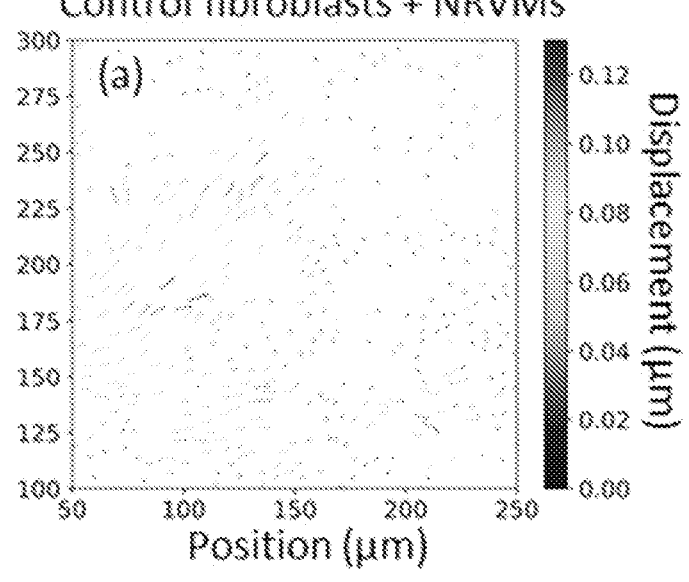
FIGS. 14A-14H shows experimental images.
Figure 14B:
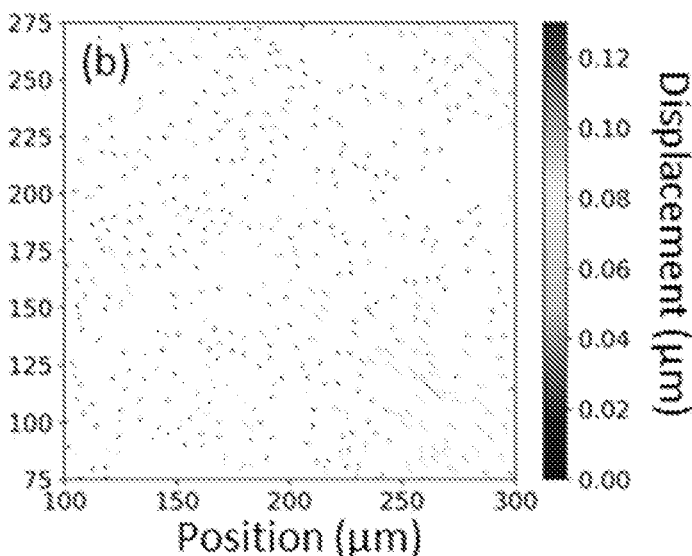
Figure 14C:
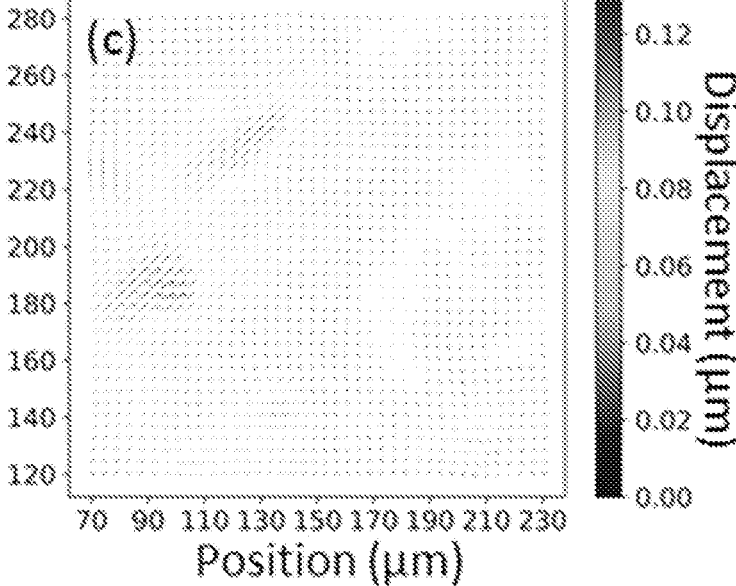
Figure 14D:
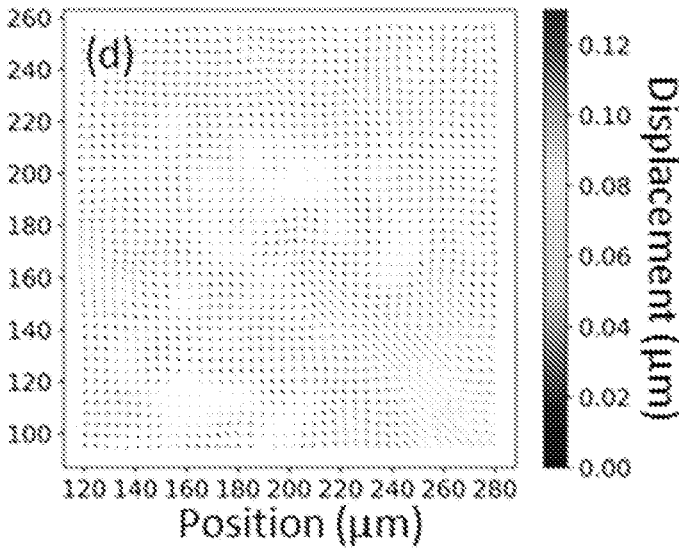
Figure 14E:
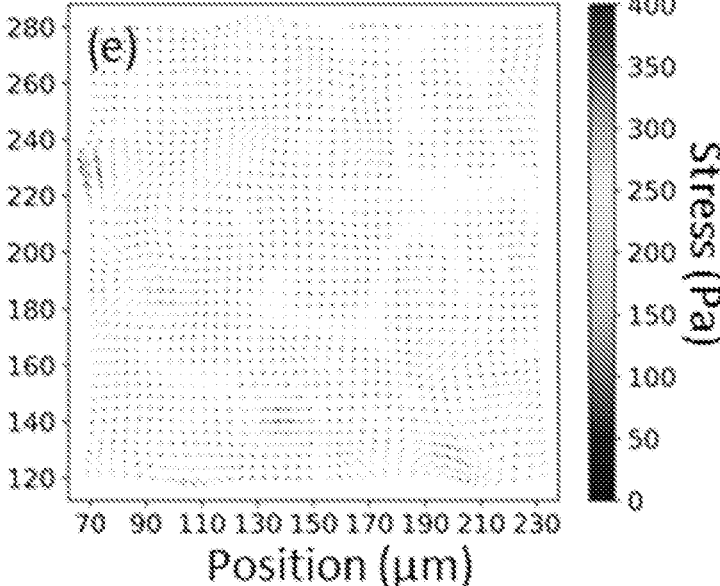
Figure 14F:
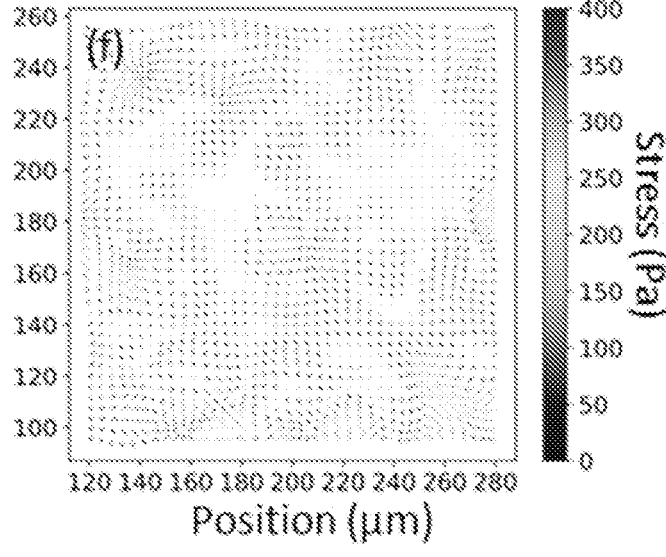
Figure 14G:
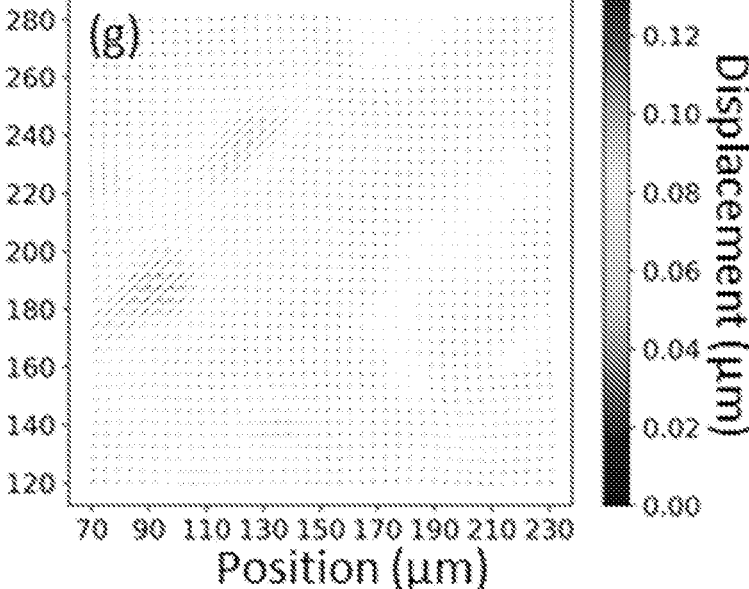
Figure 14H:
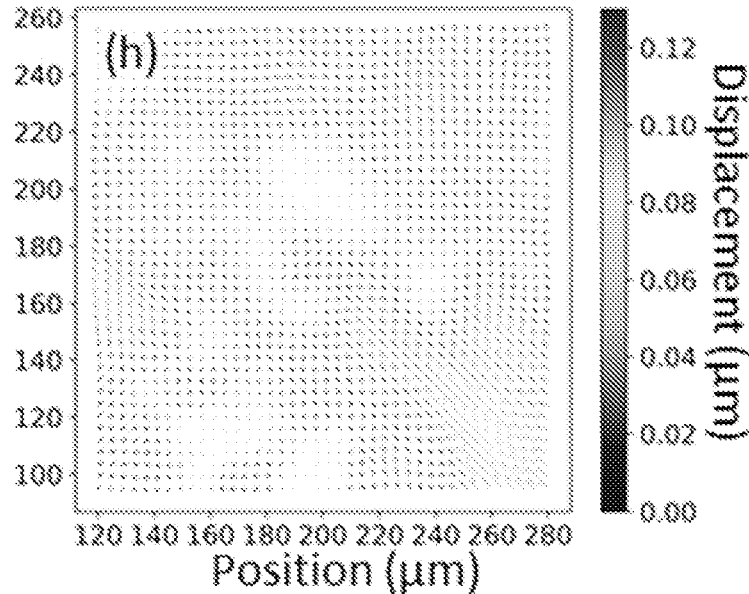

An area spanning 200 µm by 200 µm was selected from the video taken by a 20× magnification objective lens under a dark field microscope (Zeiss AxioScope A1, EC Epiplan-Neofluar, 20×, N.A.=0.5). Two image frames were used to calculate the displacement of the gold nanoparticles. The reference frame was chosen as the frame in which the cells were not beating. The peak frame was chosen as the frame in which the cells and gold nanoparticles had the largest displacement. The positions of the gold nanoparticles were determined using the Gaussian fitting method as described. The displacement was taken to be the difference in the positions of the gold nanoparticles between the peak frame and the reference frame. FIGS. 14A-14B show the displacement of each of the gold nanoparticles. The displacements in FIGS. 14A-14B were then interpolated and a two-dimensional Fourier transform filter was applied to process the interpolated data to eliminate the components of high spatial frequencies. The resulting interpolated displacements after Fourier filtering are shown in FIGS. 14C-14D. The displacements from FIGS. 14C-14D were then input into the machine learning model. The machine learning model then output the stress distributions as shown in FIGS. 14E-14F. The predicted stress distributions were then inputted back into the COMSOL software to confirm that the simulated displacements (FIG. 14G) match with the interpolated displacements (FIG. 14C) with an overall error of 2% for the control group. The overall error of the displacements was 10% for the mutant group (FIGS. 14D and 14H). The errors were calculated by the expression:

$$\sigma = \frac{\sum_{x,y}(u_{simulated}(x,y) - u_{actual}(x,y))^2 + \sum_{x,y}(v_{simulated}(x,y) - v_{actual}(x,y))^2}{\sum_{x,y}(u_{actual}(x,y))^2 + \sum_{x,y}(v_{actual}(x,y))^2}$$

where $u_{simulated}(x,y)$ and $v_{simulated}(x,y)$ are the x and y vector components of the simulated displacement from COMSOL in FIG. 14G, and $u_{actual}(x,y)$ and $v_{actual}(x,y)$ are the x and y vector components of the displacement in FIG. 14C. Note that the displacements are functions over space $(x,y)$. It can be seen that the magnitude of the stresses are larger for the control group FIG. 14E as compared to the mutant group FIG. 14F.

Parallel Microfiltration

To measure the deformability of wild-type and Col5a1 null fibroblasts, we used parallel microfiltration (PMF) as described in our previous studies (PMID: 26626154, 27875276, 30509116), to assess the ability of cells in a suspended state to filter through 10 μm pores of a membrane in response to applied pressure. The volume of retained, cell suspension indicates the number of pores that are occluded: the volume of cell suspension retained in the top well reflects the occlusion of pores, which is largely determined by cell deformability: lower retention indicates a sample with more deformable cells. Polycarbonate membranes with 10 μm pore size (TCTP14250, Millipore) were used for all filtration experiments. Prior to the PMF assay, trypsinized cells were rested 20 m at room temperature and counted using an automated cell counter (TC20, Bio-Rad) and resuspended in medium to a density of $5\text{-}10^5$ cells/mL. Cell suspensions (400 μL) were loaded into each well of a 96-well plate sample loading plate (4 wells per sample). We measured cell viability by staining cells with Trypan Blue (T8154, Sigma) and verified that cell suspensions prior to filtration consisted of single cells; therefore, the filtration behavior is largely determined by the occlusion of viable single cells rather than apoptotic cells or larger aggregates of cells. Since cell size can also impact occlusion, we measured cell size distributions and confirmed there were no significant size differences between wild-type and knock-out cells in a suspended state. To drive cell suspensions to filter through the 10 μm pores, we applied an air pressure of 2.0 kPa for 30 s. To quantify retention volume, we transferred the cell suspension retained in the top well after filtration to a 96-well plate and measured the absorbance of phenol red at 562 nm using a plate reader (SpectraMax M2, Molecular Devices). Using a standard curve, we calculated the retained volume. Retention was determined by comparing the volume of cell suspension that remains in the top well after filtration compared to the initial volume loaded (Volume$_{final}$/Volume$_{initial}$).

Atomic Force Microscopy

For atomic force microscopy (AFM) experiments, PBS-perfused hearts were dissected and mounted in OCT (Tissue-Tek, Sakura Finetek, Torrance, CA, USA) and flash frozen in liquid nitrogen-cooled isopentane. Cardiac tissue cryosections (30 μm) were mounted onto microscope slides with an adhesive coating (#SUMGP14 Matsunami Glass Ind. Ltd., Kishiwada, Osaka, Japan). Cardiac sections were incubated in rabbit anti-mouse collagen type I antibody (CL50151AP-1; 1:250; Cedarlane Labs) in PBS at 4° C. overnight and were detected by indirect immunofluorescence using Alexa Fluor 488 goat anti-rabbit secondary antibody (AB1501562; 1:500; Abcam) AFM measurements were performed on each section in PBS using a JPK Nanowizard 4A BioAFM with a 200×200×200 μm Hybrid-Stage (Bruker/JPK BioAFM, Billerica. MA, USA) coupled to a Leica M205 stereoscope (Leica Microsystems, Wetzlar, Germany). Scar regions were identified by collagen I dense immunofluorescence signal which was used as a guide for overlaying the AFM cantilever for force spectroscopy. Non-scar regions were selected in areas where collagen I signal was confined to the interstitial matrix surrounding cardiomyocytes and at least 1000 μm away from a scar region. Both scar regions and non-scar regions were probed with AppNano SHOCONGG-TL cantilevers with a 10 μm silicon dioxide sphere (nominal freq (kHz=21(8-38), k(N/m)=0.14 (0.01-0.6); AppNano, Mountain View. CA, USA). The sensitivity and spring constant of each probe were calibrated before each experiment using the contact-free calibration method. All measurements were taken in force spectroscopy mode and force-vs-indentation curves were generated from an average of 200 points/sample. Approach and retraction speeds for all force measurements were 2 μm/sec with a setpoint force of 2.5 nN and a retraction distance of 10 μm. Data analysis was performed using JPKSPM Data Processing software. To evaluate tissue stiffness, Young's modulus was calculated for each curve, using the Hertz-Sneddon model. Young's modulus data were plotted and statistics calculated in GraphPad Prism 8 software using the Kolmogorov-Smirnov nonparametric test.

Example 2: Heart Scars Attain Transcriptional Maturity Early after Ischemic Cardiac Injury Adult C57B1/6 mice were subjected to ischemic cardiac injury by permanent ligation of the left anterior descending coronary artery that supplies hulk of the blood flow to the left ventricular myocardium. Hearts were harvested at 3, 7, 14, 21 and 42 days after ischemic injury and the fibrotic scar tissue in the injured region and region remote to the area of injury (uninjured region) were dissected from the same heart for RNA sequencing (RNA-seq) to quantify temporal changes in gene expression. Principal component analysis (PCA) was used to explore global changes in transcriptional signatures of scar tissue and remote (uninjured) myocardium. All samples from remote regions at all time-points clustered together and had similar expression profiles (FIG. 1A). Principal component 1 (PC1) separated transcriptional signatures of injured and uninjured regions of the heart across all time points examined (FIG. 1A) These observations suggest that as scar formation is initiated in the injured region and matures over the next 6 weeks, gene expression differences continue to persist between the injured and uninjured regions. How the transcriptional signatures of the fibrotic scar tissue change over time was then examined. Principal component 2 (PC2) separated the samples of scar tissue in a temporal manner following injury (FIG. 1A). In particular, significant differences were observed between scar tissue harvested at 3 and 7 days following injury as well as between that harvested at 7 days and subsequent time points. However, the transcriptional signatures of the injured region of the hearts at 14, 21 and 42 days after injury clustered together demonstrating that most transcriptional changes occur within 2 weeks of injury (FIG. 1A). Next, differential gene expression analysis was performed between scar tissue and uninjured regions at each time-point, and between samples of scar tissue harvested at successive time-points (FIG. 1B) In agreement with PCA, the largest number of differentially expressed genes occurred between injured and uninjured samples at each analyzed time-point (from 1210 to 1931) (FIG. 1B). Comparisons between time-points of injured regions only detected 247 differentially expressed genes (DEGs) between Day 3 and Day 7 after injury, and 100 DEGs between Day 7 and Day 14 after injury. Almost no differences were detected between scar tissue harvested at later time-points (FIG. 1B). These data demonstrate that major transcriptional changes within scar tissue occur early after injury and further evolution of scar tissue beyond 2 weeks is not associated with significant transcriptional changes.

Scar tissue predominantly consists of extracellular matrix proteins such as collagens, and collagens were one of the most differentially upregulated genes in the injured region early after cardiac injury. Expression pattern of genes encoding obligatory subunits of all types of collagen were examined (FIG. 1C). In addition to type I and III collagens, genes encoding for various subunits of Collagen V, VI, VILI, XI, XII, XIV, XV, XVIII were observed to be significantly induced after heart injury (FIG. 1C), irrespective of the type of collagen, the expression of most collagens increased by 3 days, peaked at 7 days and declined by 42 days after ischemic cardiac injury (FIG. 1C). To confirm the temporal nature of gene expression of all collagens observed by RNA-seq, the injured and uninjured regions of the heart were dissected at different time points starting from 3 days to 6 weeks and performed qPCR for the principal genes encoding all mammalian collagens (FIG. 1D). Consistent with the patterns observed on RNA-seq, expression of most collagen encoding genes including Col1a1, Col3a1 and Col5a1 peaked at 7 days following injury. Col1a1 and Col3a1 demonstrated the most robust gene expression changes after acute injury consistent with Collagen I and III being the principal fibrillar collagens in the heart (FIG. 1D). Collagen encoding genes that are known to be abundantly expressed in extra-cardiac tissues such as Col2a1, Col7a1 and Col9a2 demonstrated dynamic expression changes on qPCR but absolute levels of expression of such genes were low. Taken together, these data demonstrate that a diverse set of collagen genes including several that are minimally expressed in the uninjured heart are robustly induced early after acute ischemic cardiac injury.

Figure 2A:
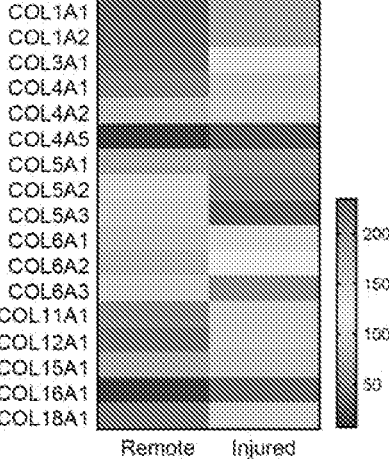
FIGS. 2A-2G show expression of Col5a1 in relation to Col1a1 and Col3a 1.
Figure 2B:
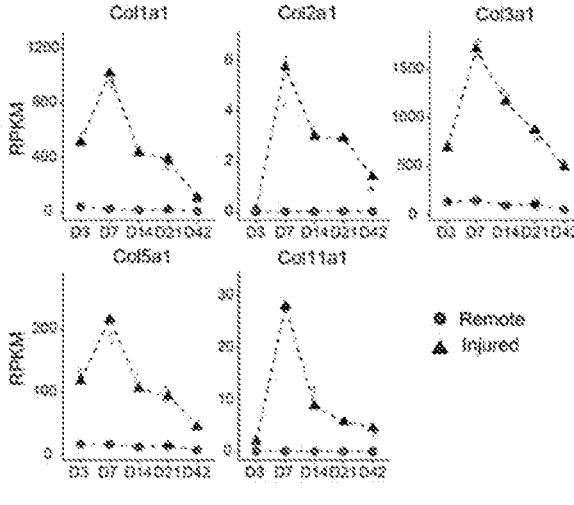

Example 3: Col5a1 Expression Overlaps Col1a1 and Co3a1 Expression in the Infarcted Region with a Single Cardiac Fibroblast Expressing all Three Collagens The nascent scar tissue was next dissected at 7 days following injury and proteomic analysis of the collagens differentially expressed between the scar tissue and uninjured regions of the same heart was first performed (FIG. 2A). We observed increased levels of the fibrillar collagen peptide chains COL1A1, COL3A1 and COL5A1 and other collagen peptide chains corresponding to and consistent with the gene expression data (FIG. 2A). The relative abundance of fibrillar collagens was analyzed showing that the Col1a1 and Co3a1 genes were the most abundantly expressed fibrillar collagen genes in scar tissue at 7 days following injury (FIG. 2B). Out of other fibrillar collagens (II, V, XI), minimal expression of Col2a1 and Col11a1 were observed. Col5a1 remained the only other fibrillar collagen gene to be robustly induced early in scar tissue and even though the abundance of Col5a1 transcripts was significantly lower than that of Col1a1 or Col3a1 (FIG. 2B), the relative abundance of Col5a1 transcripts was significantly greater by almost an order of magnitude compared to other genes encoding for subunits of known fibrillar collagens (FIG. 2B).

Figure 2C:
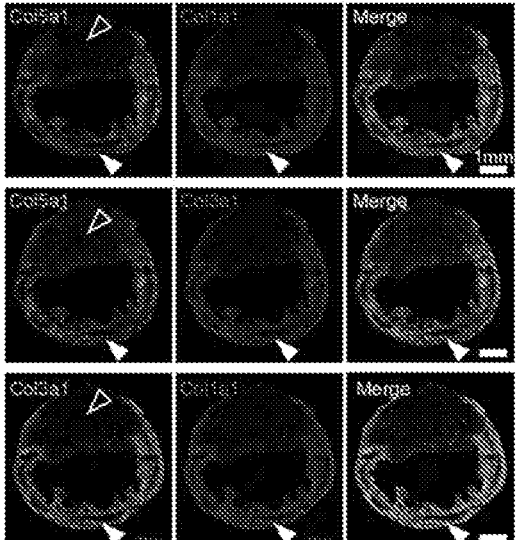
Figure 2D:
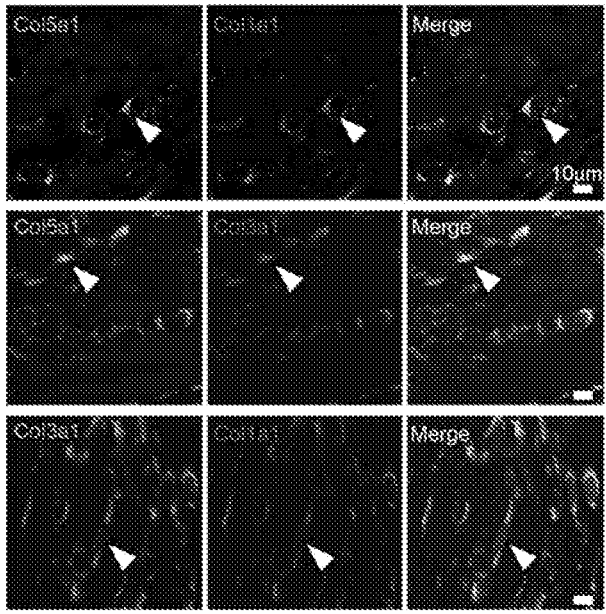
Figure 2E:
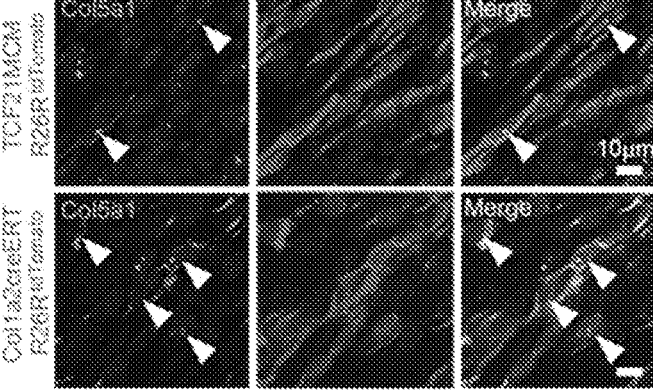
Figure 2F:
Figure 2G:
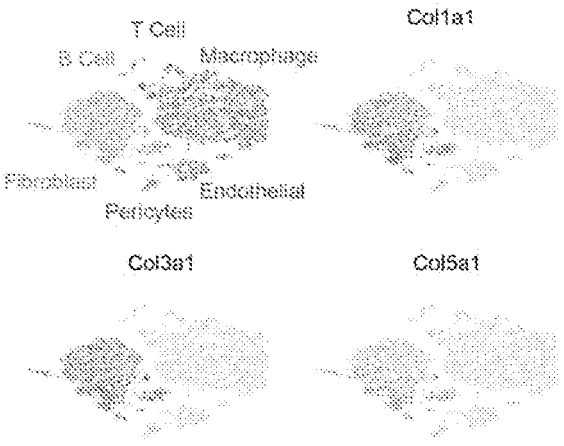

The spatial expression of the fibrillar collagens Col I, III and V was next examined. The bijective of this experiment was to determine whether the same cell expressed all the three fibrillar collagens (I, III V) or whether the collagens were expressed by different cells in scar tissue. As commercially available antibodies to detect a specific type of collagen can exhibit cross reactivity against different collagens and to facilitate accurate imaging for colocalization of fluorophores, RNA-fluorescence in situ hybridization (RNA-FISH) was performed to determine the spatial expression of Col5a1 versus Col1a1 or Col3a1 in the injured heart. RNA-FISH demonstrated robust and overlapping expression of Col5a1 with either Col3a1 or Col1a1 mRNA in, the injured region of the heart (FIG. 2C) and the same cell to express both Col5a1 and Col3a1/Col1a1 were observed (FIG. 2D). To confirm these observations, RNA-FISH in mice with genetically labeled cardiac fibroblasts was performed. For this purpose, mice expressing fibroblast Cre drivers (Col1a2CreERT or TCF21MerCreMer) were crossed with the lineage reporter Rosa26tdTom ato mice. Progeny mice (12-16 week adults) were administered tamoxifen daily for 10 days to induce Cre mediated recombination and labeling of cardiac fibroblasts as described in Ubil, E, et al. Nature 2014.514(7524): p. 585-90 and in Pillai, I.C., et al Cell Stem Cell 2017.20(2): p. 218-232 e5. Animals were then subjected to ischemic cardiac injury and RNA-FISH on hearts harvested at 7 days demonstrated tdTomato labeled cardiac fibroblasts to express Col5a1(FIG. 2E). As cardiomyocytes are known to express collagens, immunostaining for cardiac troponin 1 was performed, but did not observe cardiomyocytes to express Col5a1 (FIG. 2F). To provide corroborative evidence, single cell RNA-seq of the non-myocyte cell fraction of the injured region of the heart at 7 days following ischemic injury was performed and significant overlap between Col5a1 expression and Col3a1 and Col1a1 expression was observed (FIG. 2G). Taken together these observations demonstrate that collagen I, III and V have overlapping expression in the area of injury and that a single cardiac fibroblast has the ability to produce both collagen V and collagen I/III.

Figure 3A:
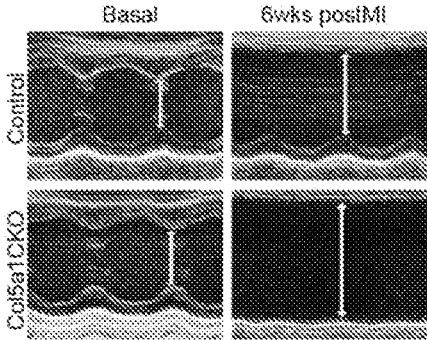
Figure 3B:
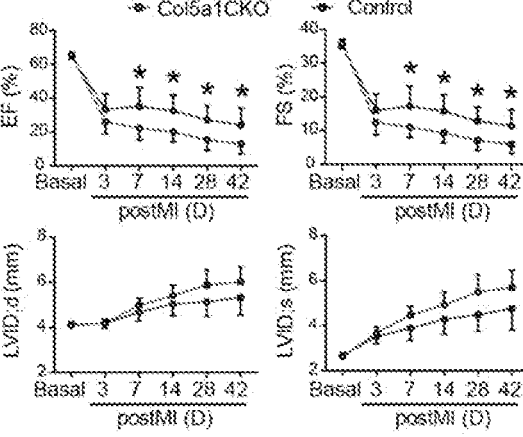

Example 4: Mice Deficient in Type V Collagen Exhibit a Paradoxical Increase in Fibrosis and Scar Size after Heart Injury Homozygous deletion of Col5a1 gene results in absence of functional collagen V protein in tissues and causes early embryonic lethality. To determine the functional role of collagen V in the injured heart, the Col1a2CreERT mice (Col1a2 being abundantly expressed in cardiac fibroblasts) was crossed with mice that have both Col5a1 alleles floxed. Tamoxifen was administered to mice for 5 days prior to ischemic injury and tamoxifen continued to be administered for the first seven days after injury to maximize labeling of activated fibroblasts and deletion of Col5a1 (Col5a1CCKO or conditional knock out). Control animals included littermates which lacked the Cre transgene but had both Col5a1 alleles floxed and were injected with tamoxifen in an identical manner. For the purposes of analysis, the performing investigator was masked to the genotype. RNA-FISH on the Col5a1CKO animals demonstrated 66.6±17.8% reduction of Col5a1 expression compared to wild type littermates (mean±S.D. *p<0.05, n=4 animals/control and 5/CKO group). Col5a1 expression was normalized to Col1a1 expression in both groups. The animals were followed with serial cardiac functional measurements b echocardiography as well as histological analysis. Significant depression of ejection fraction (EF) and fractional shortening (FS) (both measures of cardiac contractile performance) were observed by 7 days in the Col5a1CKO group following ischemic cardiac injury, the dysfunction persisting throughout the next 6 weeks of follow up (EF and FS of 13.0±9.4% and 6.0±4.4% respectively in Col5a1CKO group versus 24.3±11.9% and 11.4±5.8% respectively in control group at 6 weeks post injury), (mean±S.D. *p<0.05, n=8 animals/control and 12/CKO) (FIG. 3A,B). Depression in EF was also associated with a strong trend towards chamber dilatation determined by measurement of left ventricular internal dimensions (LVID) in systole or diastole (p=0.06 for LVID (d) at 6 weeks post MI) (FIG. 3B). Masson trichrome staining of hearts sectioned at the mid ventricle, apex and close to suture used for ligating the artery, demonstrated significantly greater surface area of scar tissue in the Col5a1CKO animals compared to wild type littermates (FIG. 3C. The surface area of fibrosis or scar identified by Masson trichrome stain in the Col5a1CKO animals was almost 1.5 times that observed in the control littermates measured at 6 weeks post injury (scar surface area, expressed as a fraction of the total let ventricular surface area of 39±12.9% in Col5a1CKO versus 25.5±11.4% in control, mean±S.D.: *p<0.05, n=8 animals/control and 12/CKO)(FIG. 3D).

Figure 3F:
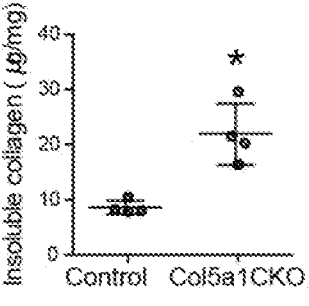
Figure 3G:
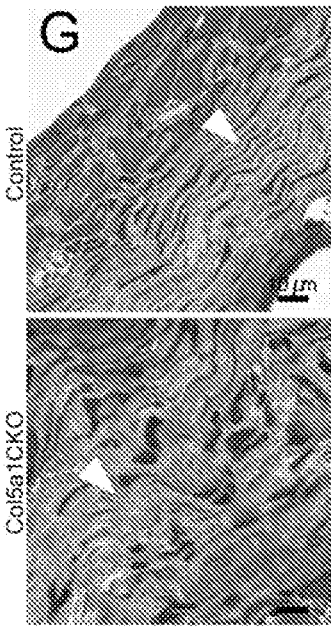
Figure 3H:
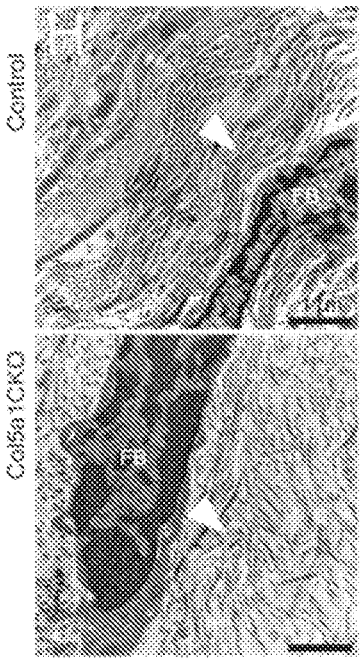
Figure 3I:
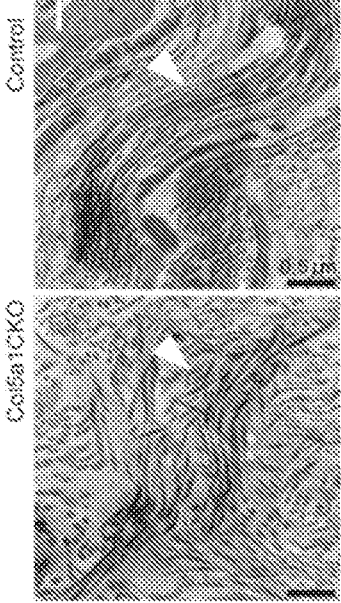
Figure 3J:
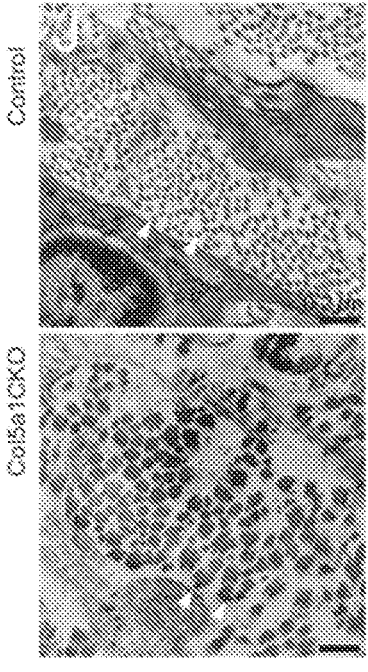
Figure 3K:
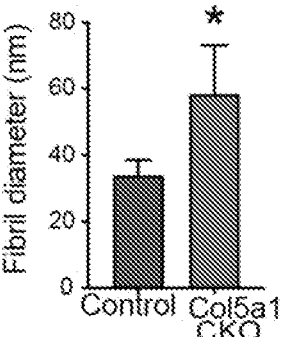
Figure 3L:
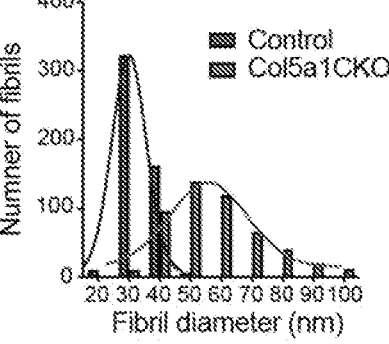

To further analyze the wound healing response in Col5a1CKO animals, the fraction of animals in the Col5a1CKO and control groups which exhibited mild, moderate or severe fibrosis after ischemic injury was determined. Mild, moderate and severe fibrosis were defined as scar surface area less than 20%, between 20% and 40% and greater than 40% of the left ventricular surface area respectively measured at 6 weeks following injury. Greater than 58% of the Col5a1CKO animals had severe fibrosis compared to approximately 12% of animals in control littermates (FIG. 3E). As scars mature, collagen fibrils undergo cross linking within scar tissue. Cross linked collagen is less soluble and to confirm the histological analysis, the amount of insoluble collagen (surrogate for cross linked collagen) measured at 6 weeks post injury was increased by 254±64% (mean±S.D., *p<0.05, n=4 animals/group) in the Col5a1CKO group (FIG. 3F). Collagen V is thought to initiate organization of Collagen I and III fibrils in the extracellular matrix and intercalates itself between the staggered arrangement of collagen 1 and collagen III fibrils maintaining organization of the ECM. The ultrastructure of scar tissue was thus examined in Col5a1KO animals. Toluidine blue staining was first performed and the typical wavy nature of collagen fibrils compactly arranged in parallel in the injured hearts of the control animals was observed, but the hearts from the Col5a1CKO animals lacked the compact wavy pattern with a loose arrangement of collagen fibers (FIG. 3G) To examine the micro-architecture of scar tissue in greater detail, transmission electron microscopy was performed and lack of parallel organization of collagen fibers in the Col5a1CKO animals compared to control littermates was observed (FIG. 3L), There was clear evidence of fibrillar disarray in the Col5a1CKO hearts; instead of the smooth parallel arrangement of collagen fibrils in the control hearts, crisscrossing of collagen fibrils with fibrils running at orthogonal axes to each other in their Col5a1CKO scar tissue was observed (FIG. 3I). The diameters of collagen fibrils were next measured and a significant increase in the average diameter of a collagen fibril in the Cola1 CKO mice was observed (FIGS. 3J and 3K). A histogram of the numbers of collagen fibrils versus their diameter demonstrated a rightward shift of the curve compared to that in control animals (FIG. 3L). Taken together these observations demonstrate that deletion of type V collagen leads not only in increased scar size but also results in grossly abnormal scar architecture.

As increased scar size in the post infarcted heart is associated with adverse remodeling phenotypes such as hypertrophy of cardiomyocytes in the border zone, hearts were harvested at 6 weeks following injury and significantly greater heart weight/body weight ratios of Col5a1CKO hearts compared to control littermates were observed (7.2±1.5 mg/g versus 6.2±1.2 mg/g, nean±S.D., *p<0.05, n=8 animals/control and 12/CKO) suggesting of cardiac hypertrophy around the scar tissue that is substantial enough to affect heart weight/body weight ratios. To confirm these observations, immunostaining for cardiac troponin I was performed in the Col5a1CKO mice at 6 weeks following injury and robust hypertrophy of cardiomyocytes abutting the margins of the scar (borderzone) compared to that in control littermates was observed.

Figure 4A:
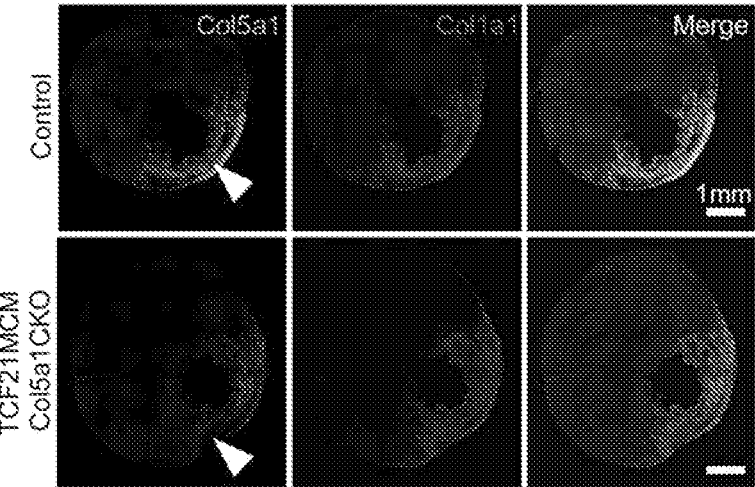
FIGS. 4A-4J show that Col5a1CKO mice generated by using the TCF21MerCreMer driver also exhibit increased scarring following ischemic heart injury.
Figure 4B:
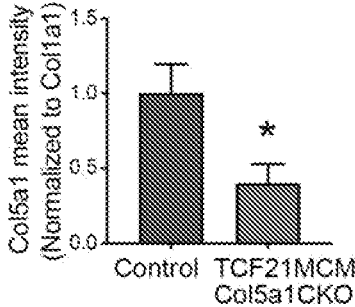
Figure 4C:
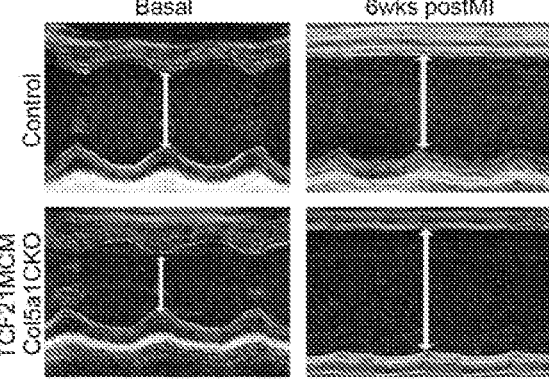
Figure 4D:
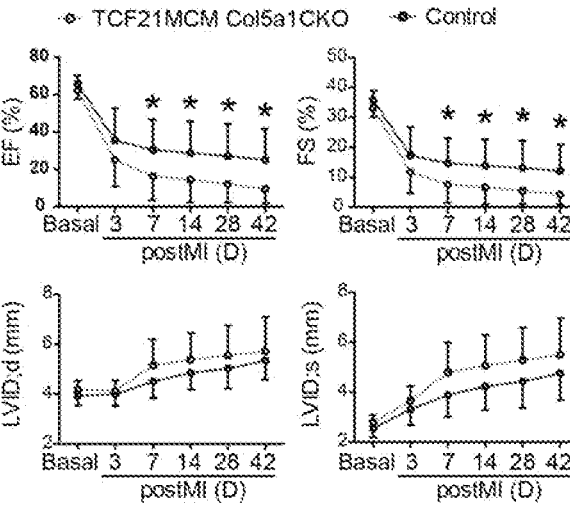
Figure 4E:
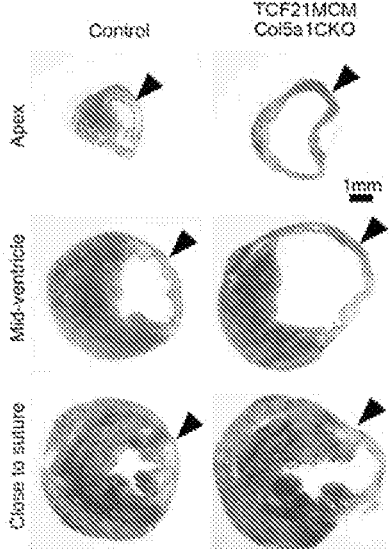
Figure 4F:
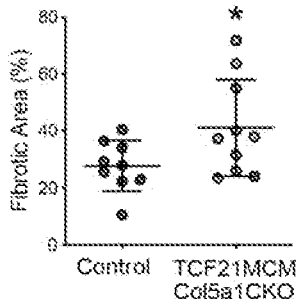
Figure 4G:
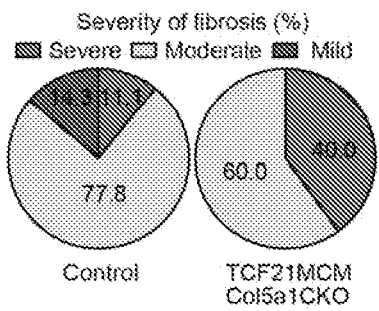
Figure 4H:
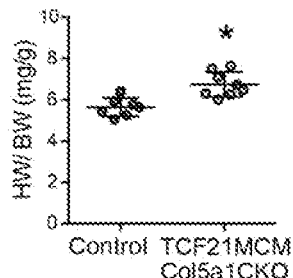
Figure 4I:
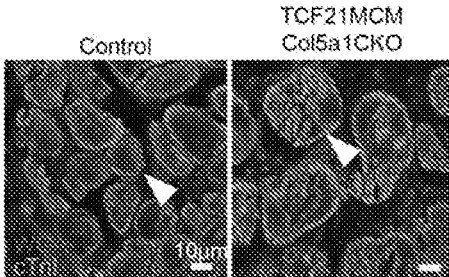
Figure 4J:
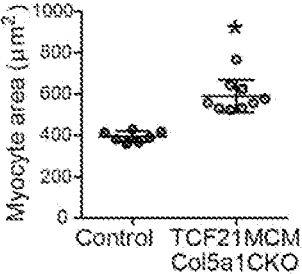

Example 5: Validation of Phenotype of Collagen V Deficiency in Injured Heart Using an Alternative Cre Driver To validate our observations noted with the Col1a2Cre driver, another conditional knockout of the Col5a1 gene was generated using the Tcf21MerCreMer driver (TCf21MCM), Tcf21 being a specific marker of cardiac fibroblasts in the adult heart. The Tcf21MCM mice were crossed with the Col5a1 floxed mice and tamoxifen administered 5 days prior to injury and for 7 days following injury to create Tcf21MCM:Col5a1CKO mice. Controls included littermate animals that had both Col5a1 alleles floxed but lacked the Cre transgene and were injected with tamoxifen in an identical manner. First, the hearts were harvested at 7 days following injury and observed decline in Col5a1 expression in the injury region by almost 60.1±10.1% (mean±S.D., *p<0.05, n=6 animals/Control and 4/CK) group) (FIG. 4A,B). Following ischemic injury, animals were followed with serial echocardiography and similar to the Col5a1CKO mice generated by the Col1a2Cre driver, Tcf21MCM: Col5aCKO mice exhibited significant decline in cardiac contractile function by 7 days, the significant deficiency in contractile function persisting throughout the next 6 weeks of follow up (EF of 25.1±16.8% in Control versus 9.4±7.6% in Tcf21MCM:Col5a1CKO at 6 weeks after injury, mean±S.D., *p<0.05, n=9 animals/control and 10/CKO) (FIGS. 4C and 4D) and this was also associated with a trend towards greater chamber size (LVID) (FIG. 4D). Masson trichrome staining to identify the scar area demonstrated significant increase in scar tissue at the mid ventricle, apex as well as base just distal to the point of ligation (FIG. 4E). The scar size expressed as a fraction of the total left ventricular surface area was 41.2±16.9% in Tcf21MCM: Col5a1CKO versus 27.8%±8.9% in control littermates (mean±S.D., *p<0.05, n=9 animals/control and 10/CKO) (FIG. 4F). We again determined the fraction of animals that demonstrated mild moderate and severe fibrosis and observed that the number of animals that exhibited severe fibrosis (>40% surface area) was 40% in the Tof21MCM: Col5a1CKO animals compared to approximately 11% in the control littermates (FIG. 4G). The Tcf21MCM:Col5a1CKO animals exhibited significantly greater heart weight/body weight ratios at 6 weeks after injury (6.8±0.6 mg/g versus 5.6±0.5 mg/g, mean±S.D., p<0.05, n=9 control and 8/CKO) (FIG. 4H) and histology confirmed significantly greater myocyte hypertrophy in the border zone of hearts of Tcf21MCM:Col5a1CKO animals (49.8±7.1% greater cross-sectional area in Tc2I1MCM:Col5a1CKO animals compared to that in wild type littermates, *p<0.05, mean±S.D., n=7 animals/control and 9/CKO) (FIGS. 4I and 4J). These observations using an independent Cre driver mirror the observations with deletion of the Col5a1 gene by the Col1a2Cre driver and provide compelling evidence that deletion of type V collagen leads to an exacerbated fibrotic repair response with significantly greater scar tissue formation after acute ischemic cardiac injury.

Figure 5A:
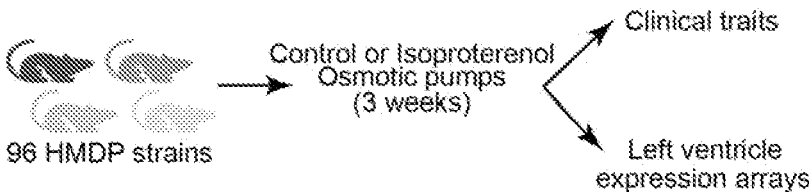
FIGS. 5A-5H show importance of Col5a1 in regulating cardiac function post injury vis-a-vis other ECM genes.
Figure 5B:
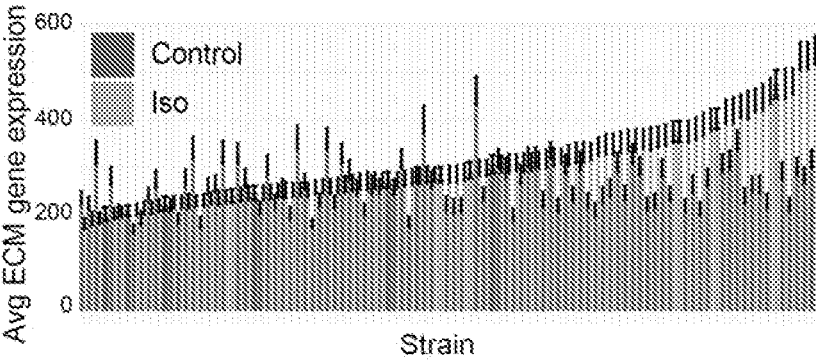
Figure 5C:
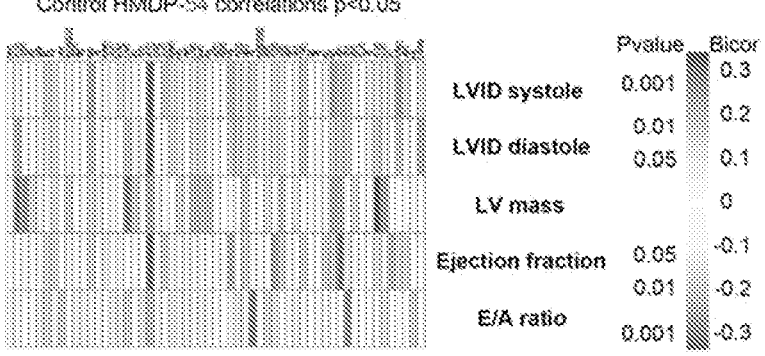
Figure 5D:
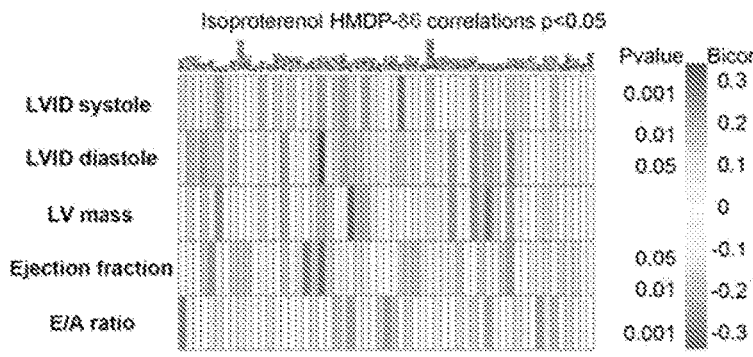
Figure 5E:
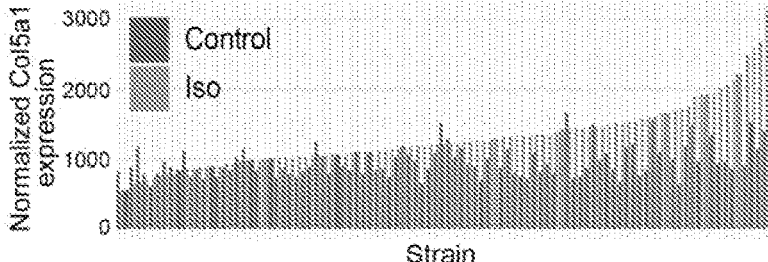
Figure 5F:
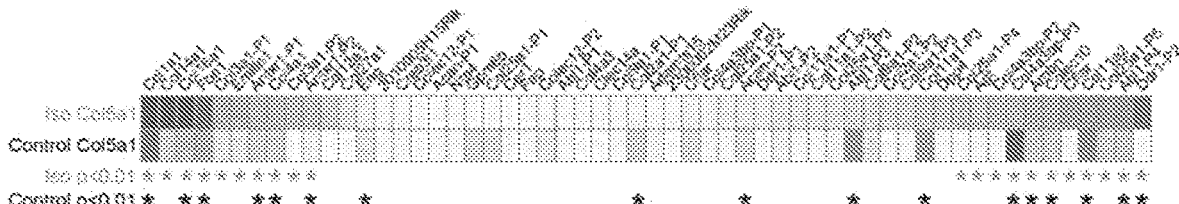
Figure 5G:
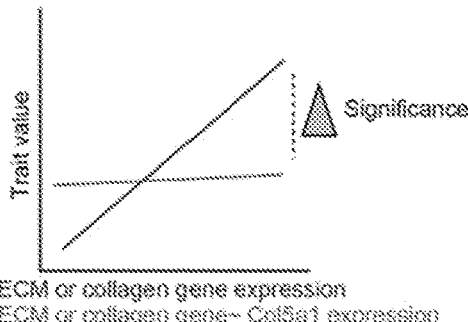
Figure 5H:
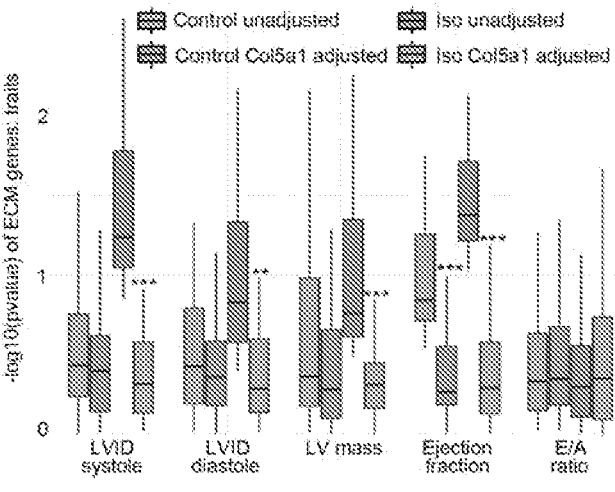

Example 6: Col5a1 is a Critical Determinant of Post Injury Heart Function Vis-á-Vis Other ECM Genes Increased post injury scaring is associated with decreased cardiac function and outcomes. However, a large number of collagens and other extracellular matrix proteins are upregulated in the region of scarring (in addition to collagen V) and an argument can be made of the functional importance of collagen V vis-a-vis other ECM proteins. We adopted a population genetics approach to determine the relative functional importance of Collagen V in driving post injury cardiac function-vis-a-vis other extracellular matrix genes. The hybrid mouse diversity panel (HMDP) comprises approximately 100 in-bred and recombinant strains of mice and each individual strain can be subjected to an identical environmental perturbation to determine the responses of strains to the defined environmental perturbation. Isoproterenol infusion induces a more chronic form of cardiac injury characterized by cardiomyocyte hypertrophy and interstitial fibrosis and the individual mouse strains in the HMDP were subjected to continuous isoproterenol infusion for 3 weeks as described in Wang, J. J., et al. PLoS Genet. 2016, 12(7): p. e1006038. Serial echocardiography was performed weekly in each strain of mouse to monitor key metrics of cardiac function such as cardiac contractile ability, chamber size and fibrosis. Changes in gene expression in the heart following isoproterenol infusion were determined in each strain of mouse and thus a mapping and correlation structure can be then utilized to identify key loci or genes that regulate a defined cardiac trait outlined in FIG. 5A. We first analyzed a set of extracellular matrix genes including collagens obtained from GO databases (Extracellular Matrix—GO:0031012 or Collagen Network—GO: 0098645) that are abundantly expressed in the heart and showed genetic variation in the average expression of these genes across the HMDP particularly following isoproterenol infusion (FIG. 5B). Next, we assessed the relationship between ECM genes and traits where we observed a strong association between expression of such extracellular matrix genes and cardiac functional traits such as chamber size, cardiac mass and ejection fraction both under control and following isoproterenol infusion (FIGS. 5C and 5D). It is worth noting that there were ~70% more significant correlations observed under isoproterenol (86 total p<0.05) compared to control (54 total p<0.05) conditions (FIGS. 5C and 5D). These observations are consistent with human clinical studies that demonstrate a strong correlation between fibrosis and cardiac function. Col5a1 also demonstrated genetic variation across the HMDP (FIG. 5E) and we analyzed the strength of association between Col5a1 gene expression and the above mentioned set of extracellular matrix genes and observed a significant correlation between Col5a1 and ECM genes (FIG. 5F). Given that (i) ECM genes strongly correlate with clinical traits and (ii) Col5a1 gene expression strongly correlates with expression of ECM genes, we focused on conditional analyses to determine the functional importance of Coi5a1 in potentially mnediating ECM:trait correlations. Significance thresholds calculated for the regressions of ECM genes and traits were compared between unadjusted values and those adjusted for Col5a1 expression. We hypothesized that if Col5a1 significantly contributed towards the strength of correlation between ECM genes and traits, then adjustment for Col5a1 expression should reduce the overall significance of correlation between ECM genes and traits, the hypothesis illustrated in FIG. 5G. To determine how Col5a1 adjustment affects the strength of association between ECM genes and defined cardiac traits, we looked at individual traits of left ventricular dimensions, LV mass, ejection fraction and EA ratios under control and following isoproterenol infusion. The distributions of the −log 10 of the p values for all ECM genes and traits, either unadjusted or following adjustment for Col5a1 expression were compared. The adjustments for Col5a1 led to a significant reduction in the overall strength of the association between ECM genes and cardiac traits of chamber size, LV mass (hypertrophy) and ejection fraction while measures of diastolic compliance (as assessed by E/A ratios) were not affected following Col5a1 adjustment (FIG. 5H). Taken together these data demonstrate that the pattern of Col5a1 variation contributes significantly towards the strength of association between extracellular matrix genes and cardiac functional traits. Using alternative cardiac injury models and complementary genetics approaches, these data support the principal observations of the physiological importance of Collagen V in regulating heart repair.

Figure 6A:
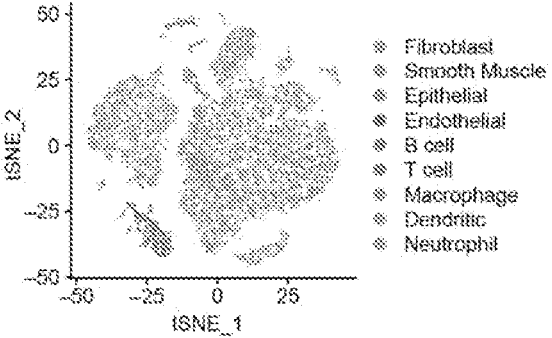
FIGS. 6A-6M show single cell RNA-seq of non-myocytes of control and Col5a1CKO hearts harvested at 7 days following injury.
Figure 6B:
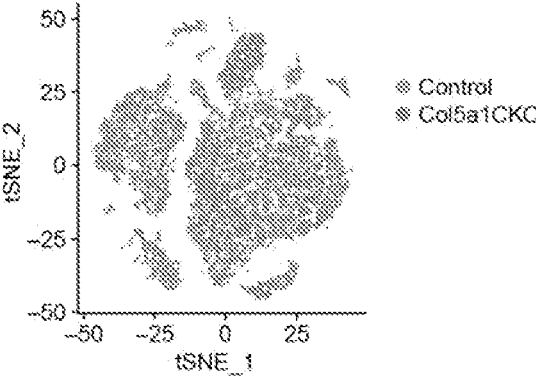
Figure 6C:
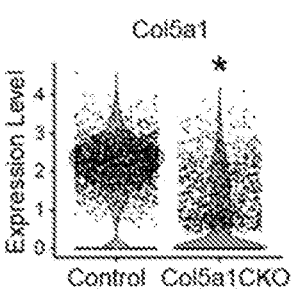
Figure 6D:
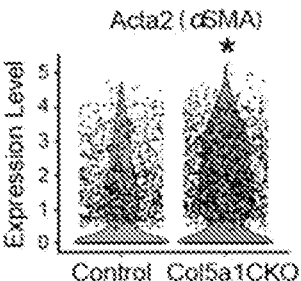
Figure 6E:
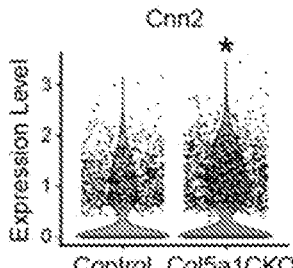
Figure 6F:
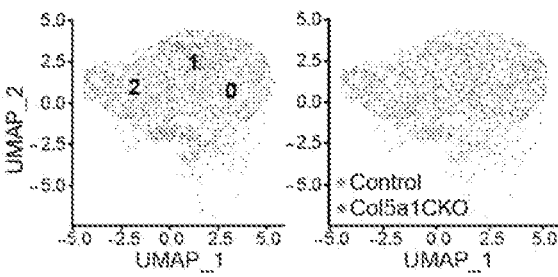
Figure 6G:
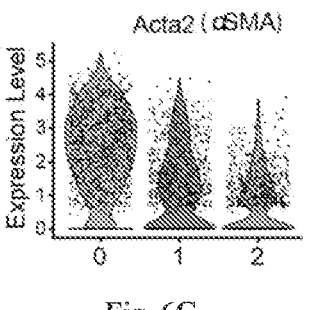
Figure 6H:
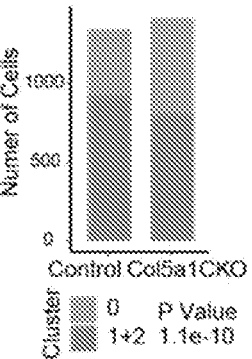
Figure 6I:
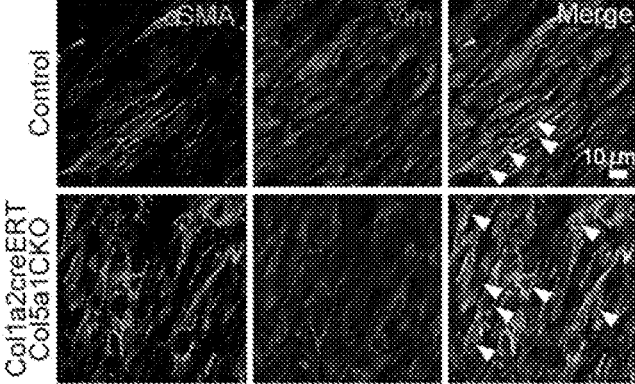
Figure 6J:
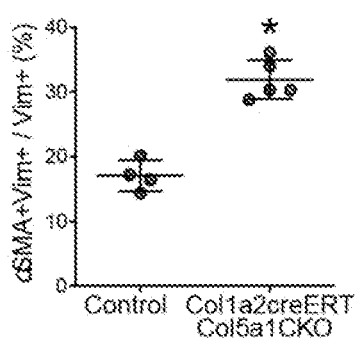
Figure 6K:
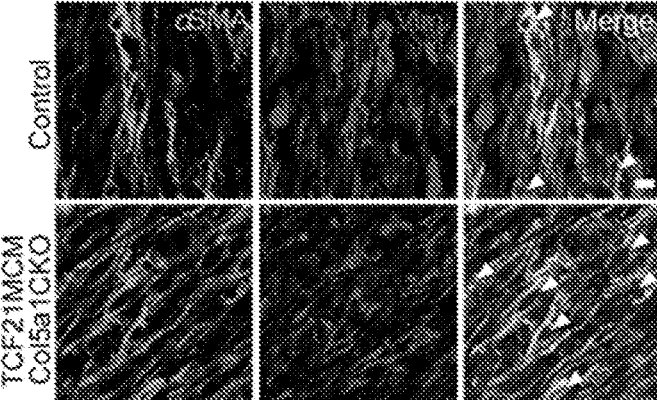
Figure 6L:
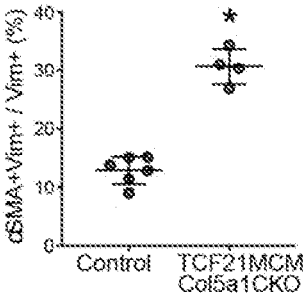
Figure 6M:
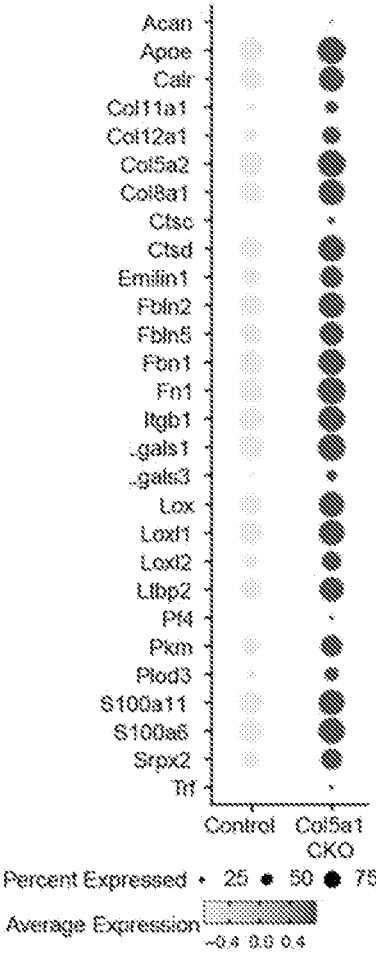

Example 7: Collagen V Deficiency Increases Myofibroblast Formation and Expression of Extracellular Matrix Genes in Scar Tissue We next investigated mechanisms by which Col5a1 deficiency leads to increase in scar size. We first examined whether the deficiency of Col5a1 altered cell populations in the scar or affected their transcriptional signatures. As maximal changes in transcriptional signatures of scars occur within the first few days after cardiac injury (FIG. 1A), we harvested the scar tissue in hearts of Col5a1CKO mice (generated by the Col1a2CreERT driver) and control littermates at 7 days following injury, isolated the non-myocyte fraction and subjected the cells to single cell RNA-seq using the 10X genomics platform. A tSNE (t-distributed stochastic neighbor embedding) plot demonstrated the major cell populations in the injured region at 7 days including a large population of macrophages and fibroblasts but also endothelial cells, smooth muscle, dendritic cells and T and B cells (FIG. 6A). We next determined the fraction of cells contributing to each cluster in the Col5a1CKO and wild type controls (FIG. 6B) and observed a comparable distribution of cells across fibroblast, endothelial, smooth muscle and other cell populations with a slightly higher number of macrophages (FIG. 6B). As Col5a1 was deleted principally in cardiac fibroblasts, we focused on differentially expressed genes in the cardiac fibroblast cell cluster and first confirmed decreased expression of Col5a1 in fibroblasts from Col5a1CKO mice compared to control animals (FIG. 6C). Fibroblasts from Col5a1CKO hearts exhibited significantly greater expression of Acta 2 (αsmooth muscle actin or αSMA) (FIG. 6D), a gene that is not expressed by cardiac fibroblasts in the uninjured heart but is a marker of myofibroblasts, and identifies a population of activated fibroblasts expressing smooth muscle contractile proteins. Myofibroblasts exhibit a synthetic and contractile phenotype and are thought to be the principal cells that secrete ECM proteins to form scar tissue following injury and also contribute to wound contraction. Other smooth muscle specific contractile proteins ((Cnn2. (calponin), Actn1 (Actinin 1), markers of smooth muscle differentiation SM22α (Tagln), proteins regulating smooth muscle contraction such as regulatory myosins (Myl 6, Myl9) or calcium handling during smooth muscle contraction (S100a4) were also significantly upregulated in fibroblasts of Col5a1 CKO animals suggestive of broad cytoskeletal organization and activation of fibroblasts in the hearts of Col5a1CKO animals (FIG. 6E). Lysyl oxidase (Lox), that mediates cross linking of collagen was also upregulated and is consistent with our earlier observations of increased amounts of insoluble collagen in scar tissue of Col5a1CKO hearts We next examined the subsets of fibroblasts residing within the fibroblast cluster in the control and Col5a1CKO animals (FIG. 6F). Sub-cluster analysis of the fibroblast population demonstrated that αSMA was abundantly expressed in Cluster0 identifying that cluster as a population enriched in myofibroblasts (FIG. 6G). We observed that the number of myofibroblasts (defined as fibroblasts expressing αSMA) (Cluster 0) was significantly increased by 33% in the Col5a1CKO animals compared to control animals (FIG. 6H). To confirm these findings, double immunofluorescent staining for αSMA and vimentin (fibroblast marker) was performed on hearts of Col5a1CKO mice. The number of myofibroblasts (defined as the fraction of αSMA+Vimentin+/total number of vimentin+cells) was significantly greater in the scar tissue of Col5a1 CRKO mice (Col1a2CreERT driver, approximately 2 fold increase in myofibroblasts*p<0.05) (FIGS. 6I and 6J) or that of Tcf21MCM:Col5a1CKO mice (TCF21MerCreMer driver, approximately 2.5 fold increase in myofibroblasts, *p<0.05) (FIGS. 6K and 6L). Analysis of differentially expressed ECM genes demonstrated a large number off CM genes to be significantly upregulated in Col5a1CKO fibroblasts including several collagens (Col8a1, Col1a1), fibronectin, osteopontin and fibrillin (FIG. 6M). The data strongly suggests that increased numbers of myofibroblasts along with increased expression of myofibroblast markers and other ECM genes in cardiac scar tissue of Col5a1CKO animals contribute to the increase in fibrosis and scar size observed in these animals. We next determined whether increased myofibroblast numbers in Col5a1CKO scar tissue were secondary to increased proliferation of Co5a1CKO myofibroblasts. To address this question, the expression of cell cycle genes that regulate S/G1 as well as G2/M transitions of the cell cycle in Cluster 0 (myofibroblast population) of the control and Col5a1CKO fibroblasts were examined but the average expression of such genes did not show any difference between the myofibroblasts of control and Col5a1CKO animals. To further support these observations on myofibroblast proliferation made through single cell RNA-seq analysis, we performed immunostaining for another marker of proliferation (Ki67), but did not observe any significant differences between the fraction of fibroblasts expressing Ki67 in control or Col5a1CKO hearts at 7 days following injury. Collectively, these observations suggest that increased myofibroblast differentiation/formation rather than myofibroblast proliferation likely underlies the increased myofibroblast numbers observed in Col5a1CKO scar tissue compared to control littermates.

Example 8: Collagen V Deficiency Alters Biomechanical Properties of Fibroblasts and Matrix in Scar Tissue The molecular underpinnings of increased myofibroblast differentiation and increased ECM gene expression in hearts of Col5a1CKO animals were explored. As collagen V is not known to be directly involved in signal transduction, alterations in the mechanical properties of cells and matrix in the Col5a1CKO animals may be providing cues to the fibroblast to drive myofibroblast differentiation and increase ECM gene expression. Transmission electron microscopy strongly suggested that the scar micro-architecture was grossly abnormal. A series of experiments were performed to first determine the effects of collagen V deficiency on biomechanical properties of fibroblasts and ECM and their effect in modulating cardiomyocyte contractile forces.

Figure 7A:
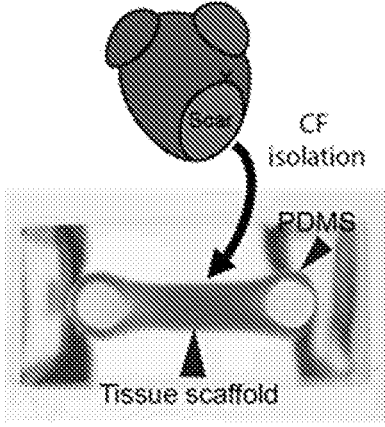
FIGS. 7A-7N show that Col5a1CKO fibroblasts exhibit altered mechano-biological properties.
Figure 7B:
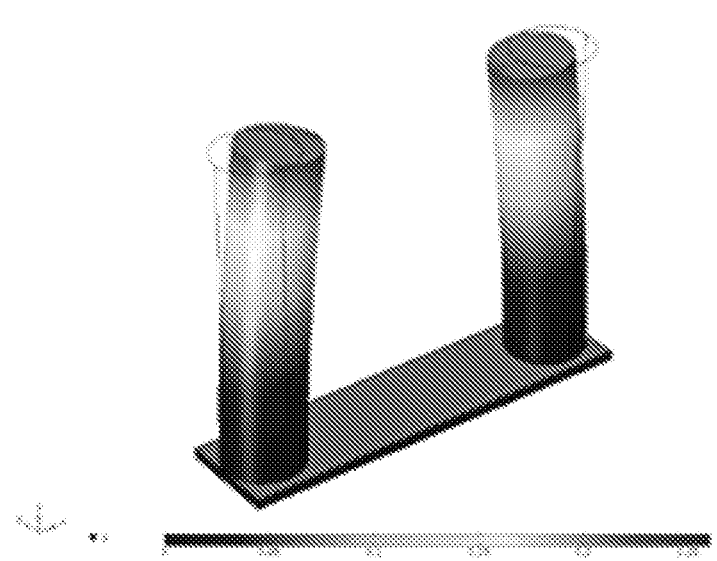
Figure 7C:
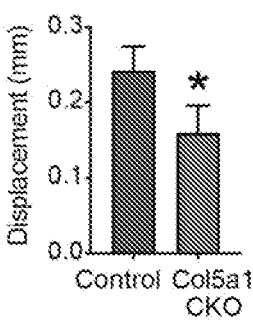
Figure 7D:
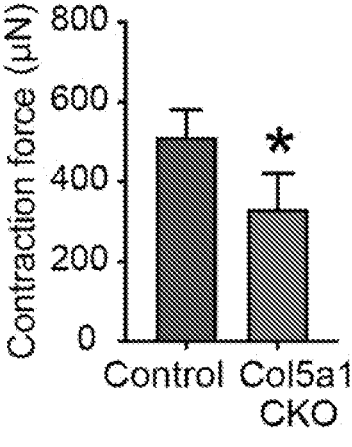
Figure 7E:
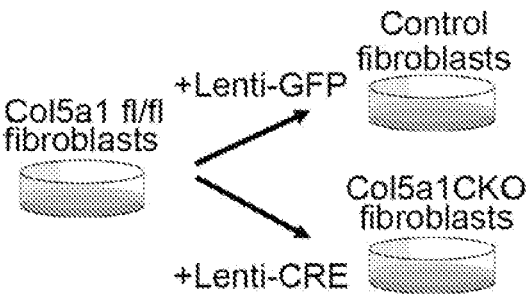
FIGS. 7E-7G shows determination of contractile forces by generating Col5a1CKO fibroblasts ex vivo.
Figure 7F:
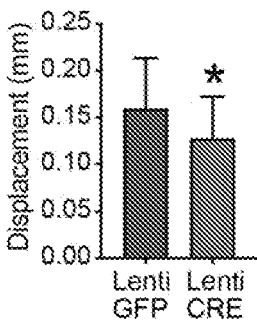
Figure 7G:
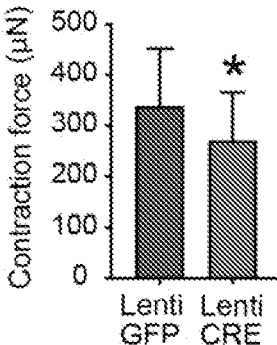

Force-contraction relationships and cell stiffness of Col5a1CKO fibroblasts were examined. Then we investigated whether the mutant cells secreting Collagen V deficient abnormal matrix directly affected the generation of contractile forces from myocytes. Cardiac fibroblasts were isolated by enzymatic digestion of hearts from Col5a1CKO mice and wild type littermates at 7 days post injury and mechanical properties of the fibroblasts were investigated under defined conditions by creating tissue scaffolds and measuring force-tension relationships (FIG. 7A). For this purpose, we fabricated a device with polydimethyl siloxane (PDMS) posts, isolated cardiac fibroblasts from infarcted hearts as above, incorporated the fibroblasts in hydrogels to form tissue scaffolds and subsequently suspended the hydrogel between two PDMS posts (FIG. 7A). Contractile ability of the cardiac fibroblasts was determined by measuring the deflection of the two PDMS posts (FIG. 7B). The tissue was cultured between PDMS posts for 72 hours. Significant reduction in displacement of the PDMS posts and the resulting force generated by the Col5a1CKO fibroblasts compared to the control wild type fibroblasts was observed (approximately 34.2% reduction in displacement and generation of contractile force in the Col5a1CKO fibroblasts compared to the WT fibroblasts, mean±S.D., p<0.05, n=3) (FIGS. 7C and 7D) To confirm these observations and to determine whether the deficiency of Col5a1 in cardiac fibroblasts is sufficient to alter the ability of cardiac fibroblasts to contract under defined conditions, cardiac fibroblasts were isolated from Col5a1 floxed mice and the cardiac fibroblasts were infected in-vitro with a lenti-virus encoding the Cre recombinase gene or GFP as control (FIG. 7E). To minimize artifacts from repeated passaging and culture induced senescence of cardiac fibroblasts, the isolated Col5a1fl/fl cardiac fibroblasts were immortalized by infecting them with a lentivirus encoding the SV40 large T cell antigen, prior to infecting the cells with Cre recombinase or control GFP virus Cells infected by Cre recombinase lentivirus were identified by co-expression of GHP fluorescence and sorted by flow cytometry and we obtained approximately 60±20% decrease in Col5a1 expression (mean±S.D. n=6. *p<0.05). Successfully transduced cells were then incorporated into hydrogels and suspended between PDMS posts in a similar manner. A significant reduction in displacement and generation of contractile force were observed, that demonstrates that the deficiency of Col5a1 is sufficient to alter myofibroblast contraction (FIGS. 7F and 7O).

Figure 7H:
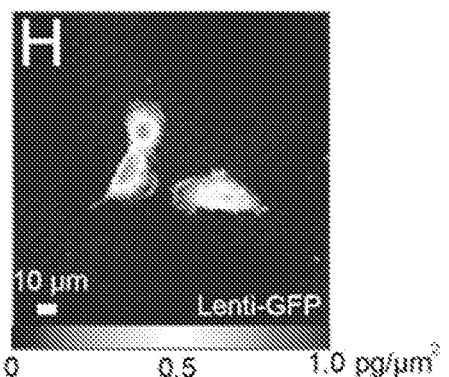
FIGS. 7H-7K shows quantitative phase microscopy (QPM) to determine cell stiffness of Col5a1CKO cardiac fibroblasts and control cardiac fibroblasts.
Figure 7I:
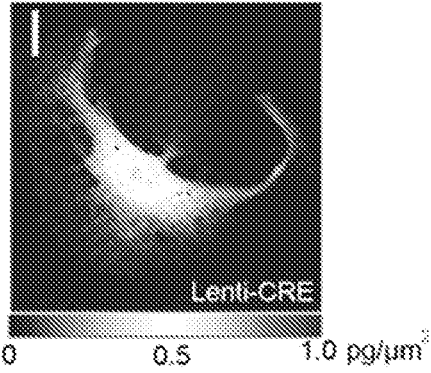
Figure 7J:
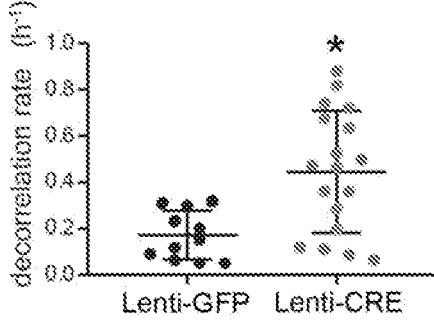
Figure 7K:
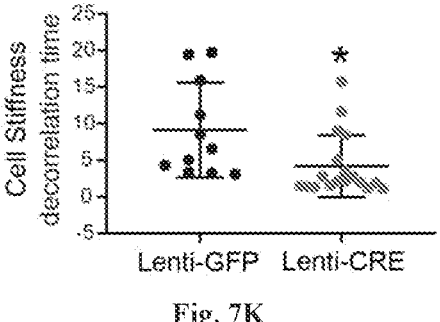

Quantitative phase microscopy (QPM) was used to determine stiffness for individual clusters of control and Col5a1CKO fibroblasts. The calculation of stiffness is based on the principle that stiffer cells redistribute their internal mass more slowly than cells that are more compliant. The rate of redistribution of internal cell mass is a reliable surrogate for determining cell stiffness as shown by comparative measurements performed with atomic force microscopy for a variety of cell types. Col5a1CKO fibroblasts generated by lentiviral Cre transduction of Col5a1 floxed fibroblasts were subjected to QPM and we observed that the rates of redistribution of internal mass (decorrelation rate) were faster (approximately two fold higher) in Col5a1CKO fibroblasts versus control-GFP virus infected fibroblasts (mean±S.D. *p<0.05, n=3 independent experiments with 11 cell clusters examined/control and 18 cell clusters/ Col5a1CKO) (FIGS. 7H-7J) Cell stiffness (inverse of decorrelation rate) was consequently significantly lower in the Col5a1CKO fibroblasts compared to controls (mean±S.D., *p<0.05, n=1/control and 18/Col5a1CKO) (FIG. 7K). It is to be noted here that the stiffness of the cells is affected by the surrounding matrix that the cells secrete, and as such the measurements reported relate to stiffness of cells surrounded by or embedded in the matrix they secrete. These observations thus demonstrate that deficiency of Col5a1 in cardiac fibroblasts is sufficient to alter the stiffness of cardiac fibroblasts.

Figure 7L:
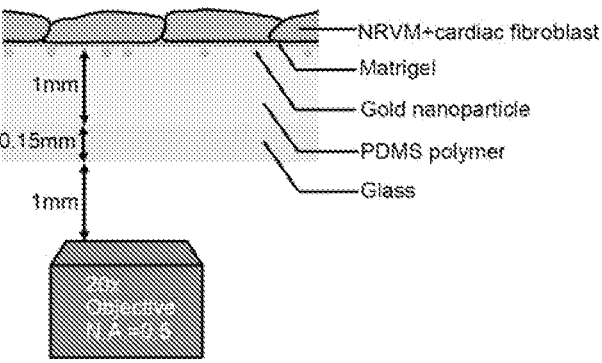
Figure 7M:
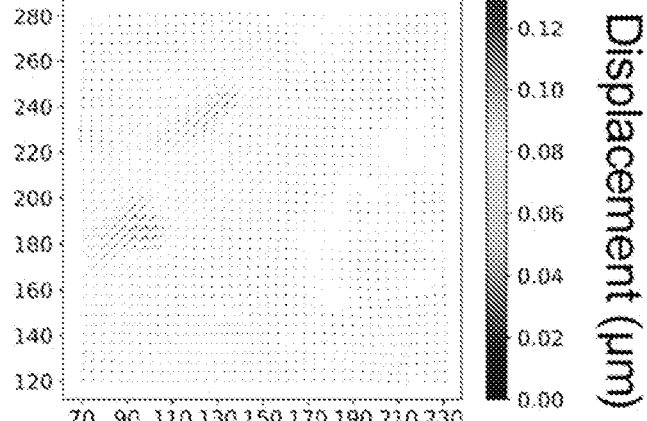
Figure 7M:
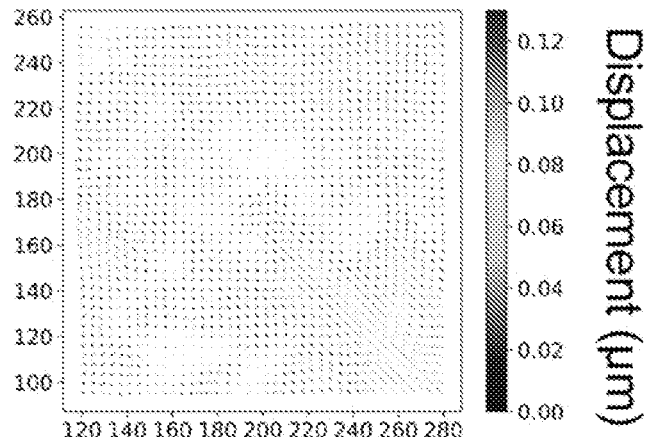
Figure 7N:
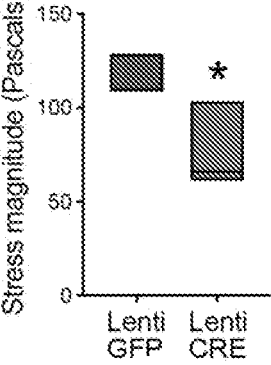

Given the abnormalities in stiffness and contraction forces generated by the Col5a1 mutant cardiac fibroblasts, whether the deficiency of Col5a1 in cardiac fibroblasts alters the generation of contractile force of cardiomyocytes was investigated. The extracellular matrix of the heart is known to affect transduction of contractile forces across the organ. To address this question, neonatal rodent ventricular cardiomyocytes (NRVM) were co-cultured with Col5a1 deficient or control cardiac fibroblasts generated in vitro following lentiviral Cre recombinase or lentiviral GFP transduction of Col5a1 fluxed cardiac fibroblasts. Fraction force microscopy was performed to determine myocyte contractile forces generated in the presence of control of Col5a1 deficient fibroblasts. A co-culture of cardiomyocytes and control or Col5a1 deficient cardiac fibroblasts was seeded onto a Matrigel surface on a PDMS scaffold containing gold labeled nano-particles (FIG. 7L). As the myocytes contract, the movement or displacement of the gold particles are captured and then machine learning approaches utilized to calculate contractile forces (FIG. 7M). Using this approach, we observed that the stress forces generated by myocytes in the presence of Col5a1 deficient fibroblasts is significantly decreased when compared to that in the presence of wild type cardiac fibroblasts (FIG. 7N) (mean±S.D. *p<0.05, n=3). These observations are consistent with the in-vivo findings of decreased cardiac contractile forces in Col5a1CKO hearts compared to control littermates following ischemic cardiac injury. Taken together, these data suggest that deficiency of Col5a1 alters the mechanical properties of the cells in their surrounding matrix and even though myofibroblast numbers are increased in the Col5a1CKO nice hearts, disorganization of scar tissue is associated with weaker myofibroblast contraction forces and decreased stiffness of fibroblasts within scar tissue.

Figure 8A:
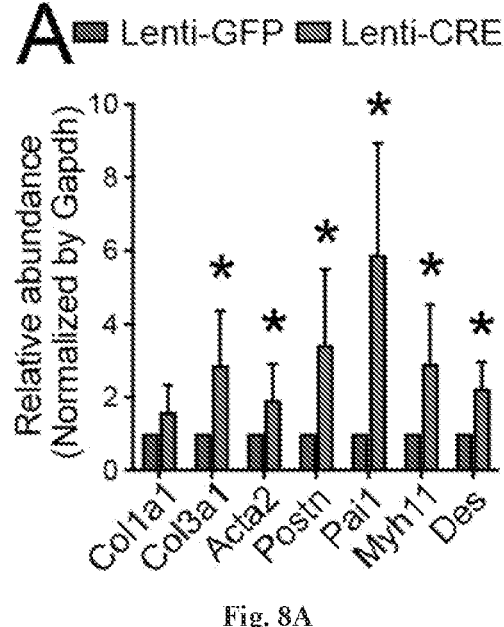
FIGS. 8A-8O show that inhibition of αvβ3 and αvβ5 integrins rescues increased scarring and cardiac dysfunction in Col5a1CKO animals.
Figure 8B:
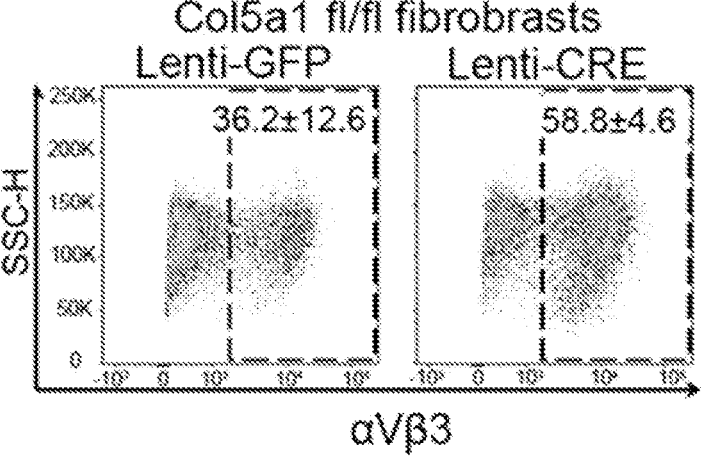
FIGS. 8B-8C show flow cytometry to determine expression of (FIG. 8B) αvβ3 and (FIG. 8C) αvβ3 integrins on Col5a1 CRKO versus control cardiac fibroblasts (mean±S.D., *p<0.05, n=6 independent experiments).
Figure 8C:
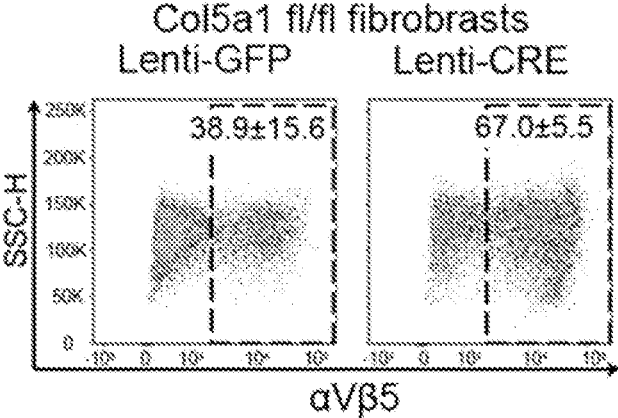

Example 9: Collagen V Deficiency Induces Myofibroblast Formation Via Altered Integrin Expression on Cardiac Fibroblasts Given the abnormal biomechanical properties of Col5a1CKO fibroblasts, mechanosensitive cues may be driving a myofibroblast gene expression program and increased myofibroblast formation. First, whether the deficiency of Col5a1 in cardiac fibroblasts was sufficient to induce myofibroblast differentiation and expression of ECM genes was determined. To address this question, Col5a1 deficient or control cardiac fibroblasts were generated by infecting isolated Col5a1floxed cardiac fibroblasts with lentiviral Cre recombinase or GFP as described earlier (FIG. 7E). Control or Col5a1 deficient cardiac fibroblasts were then co-cultured for 5-7 days (i.e. after adding the virus) followed by determination of expression of canonical myofibroblast and ECM genes by qPCR. Significant upregulation of canonical myofibroblast and ECM genes such as αSMA, Periostin, Col3a1, Myh11 etc were observed (FIG. 8A). These observations demonstrate that the loss of Col5a1 is sufficient to induce activation of a myofibroblast gene expression program. Integrins are mechanosensitive receptors on the cell surface and alterations in mechanical properties of the extracellular environment can lead to rapid changes in integrin profile. Moreover, integrins are known to regulate key cellular events such as cell survival, proliferation and differentiation. Augmentation of a myofibroblast gene expression program in Col5a1CKO fibroblasts could be secondary to altered integrin expression on the Col5a1 deficient fibroblasts. Flow cytometry was performed on Col5a1 deficient cardiac fibroblasts and a significant greater fraction of Col5a1 deficient cardiac fibroblasts expressed the integrins αvβ3 and αvβ5 (58.9±4.6% in Col5a1CKO versus 36.2±12.6% in control cardiac fibroblasts for αvβ3) and (67±5.5% in Col5a1CKO versus 38.9±15.6% in control cardiac fibroblasts for αvβ5) (mean±S.D., *p<0.05, n=6 for both αvβ3 and αvβ5) (FIGS. 8B and 8C). In contrast, β1, β2, α5 and αv integrins were abundantly present and did not show any changes in expression between the control and the Col5a1CKO cardiac fibroblasts. These integrins were chosen as they have shown to affect smooth muscle and fibroblast function, and in particular for αtβ3/αvβ5 there is evidence that these integrins promote myofibroblast differentiation by modulating latent TGFβ signaling.

Figure 8D:
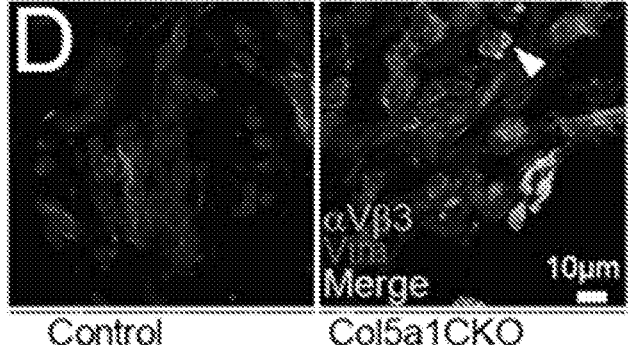
FIGS. 8D-8E show immunostaining for vimentin and (FIG. 8D) αvβ3, (FIG. 8E) αvβ5 in scar tissue of Col5a1CKO and control littermate heart at 7 days following injury demonstrates robust expression of αvβ3 and βvβ5 in cardiac fibroblasts in Col5a1CKO hearts but not in control animals (arrows, representative images).
Figure 8E:
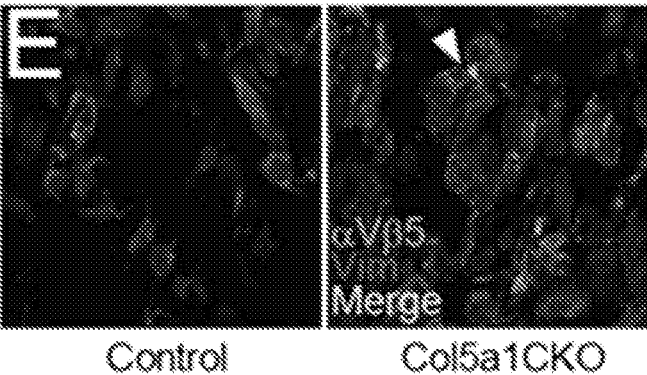
Figure 8F:
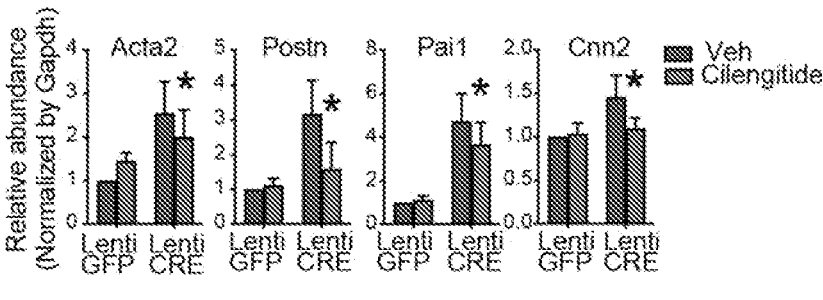
FIG. 8F shows that CSol5a1CKO cardiac fibroblasts were generated ex vivo in the presence or absence of cilengitide and qPCR performed to determine expression of key myofibroblast genes (mean±S.D., *p<0.05, n=6 independent experiments).

Immunostaining was performed on heart sections and robust expression of αvβ3 and αvβ5 integrins was observed in cardiac fibroblasts of Col5a1CKO scar tissue compared to minimal expression in those of control littermates (FIGS. 8D and 8E). Given the upregulation of αvβ3 and αvβ5 integrins in Col5a1CKO cardiac fibroblasts, whether there was a causal relationship between these differentially expressed integrins and myofibroblast differentiation was determined. To address this question, a pharmacologic loss of function approach was adopted by using the drug cilengitide, a specific inhibitor of αvβ3 and αvβ5 integrins. Cilengitide is a cyclic Arg-Gly-Asp peptide that has been used in human clinical trials of various malignancies such as gliomas, and is a specific inhibitor of the αvβ3 and αvβ5 integrins. The Col5a1 floxed cardiac fibroblasts was infected with a lentiviral Cre or control GFP and cilengitide was added to cardiac fibroblasts at the same time. After 7 days, expression of myofibroblast markers was significantly increased in the Col5a1CKO fibroblasts compared to control cardiac fibroblasts but the addition of cilengitide significantly reduced the expression of myofibroblast markers in the Col5a1CKO fibroblasts (FIG. 8F). These in-vitro experiments thus demonstrate that inhibition of αvβ3 and αvβ5 integrins is sufficient to attenuate a myofibroblast gene expression program in Col5a1CKO fibroblasts.

Figure 8G:
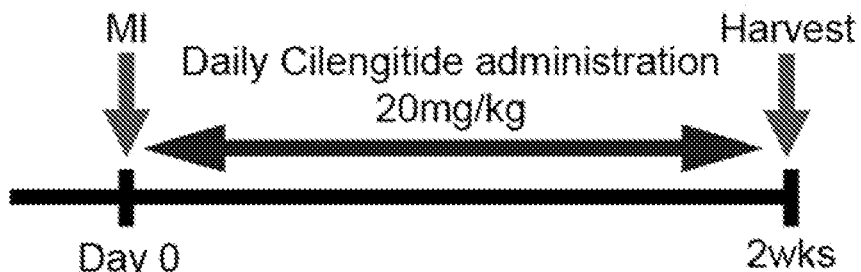
FIG. 8G shows experimental design to treat Col5a1CKO animals or control littermates with daily cilengitide (20 mg/kg) starting from day of injury.
Figure 8H:
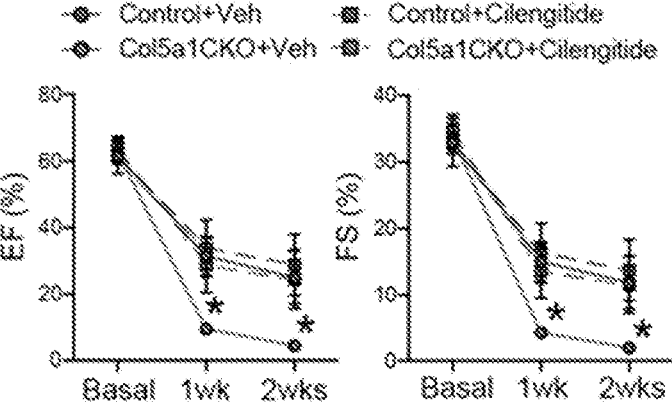
FIGS. 8H-8I show determination of cardiac contractile function (EF,FS) by echocardiography at 1 week and 2 weeks following injury in the presence or absence of cilengitide with (FIG. 8H) EF and ES at 1 and 2 weeks following injury in control littermates and Col5a1CKO animals injected with cilengitide or vehicle (meant±S.D., *p<0.05 comparing cilengitide injected Col5a1CKO animals (red dotted line) and vehicle injected Col5a1CKO animals. p>0.05 in comparing cilengitide injected Co5a1CKO animals and Control animals [Cre(-) Col5a1fl/fl) injected with cilengitide or PBS. p>0.05 comparing control animals injected with vehicle or cilengitide, n=9 CKO animals receiving cilengitide, n=3 CKO animals injected with vehicle, n=4 animals for all other groups).
Figure 8I:
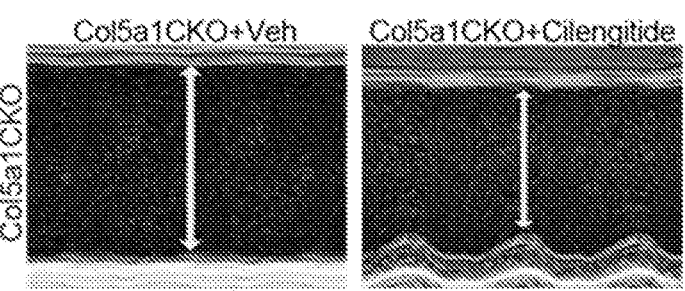
Figure 8J:
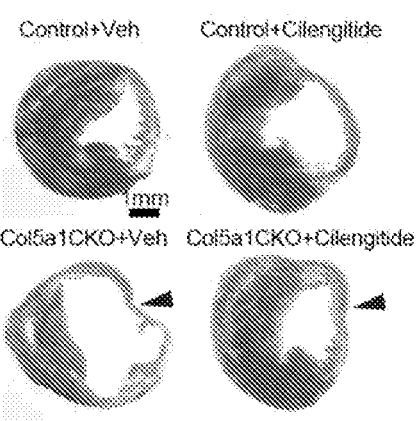
FIG. 8J shows masson trichrome staining of mid ventricle demonstrating area of fibrosis at 2 weeks following injury in the 4 groups demonstrates obvious reduction in area of scar in Col5a1CKO animals injected with cilengitide compared to vehicle injected (arrowhead, n=same animals as above).
Figure 8K:
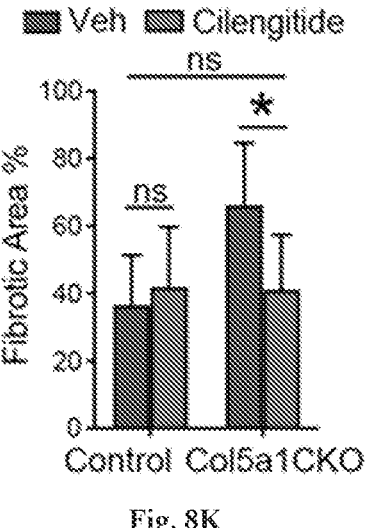
FIG. 8K shows that quantitation of area of fibrosis expressed as a fraction of the left ventricular surface area demonstrates significant reduction of scar size following cilengitide infusion (mean±S.D., *p<0.05, ns: Not significant, n=same number of animals as above).
Figure 8L:
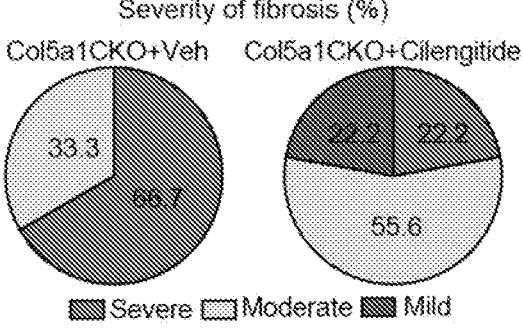
FIG. 8L shows Fraction of Col5a1CKO animals demonstrating mild (<30%), moderate (30~50%) and severe (>50%) fibrosis following PBS or cilengitide infusion.
Figure 8M:
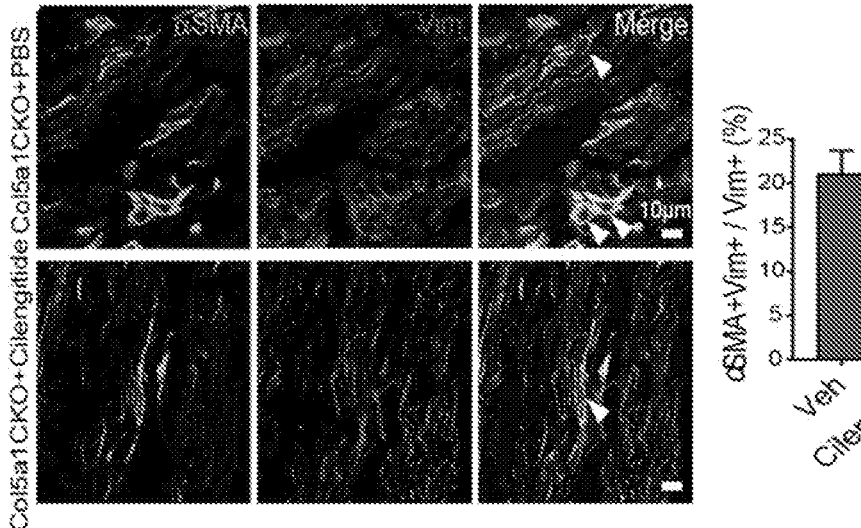
FIG. 8M shows Immunostaining for αSMA and vimentin to determine fraction of myofibroblasts in hearts of Col5a1CKO animals receiving PBS or cilengitide and quantitation of the fraction of myofibroblasts in cilengitide versus vehicle treated Col5a1CKO animals (arrows, representative images, mean±S.D., *<p<0.05, n=same number of animals as above).
Figure 8N:
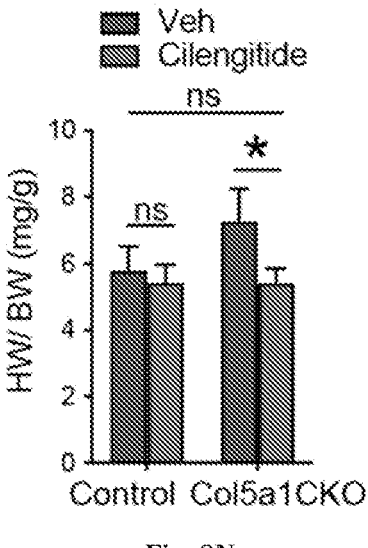
FIG. 8N shows heart weight/body weight of hearts harvested at 2 weeks following injury (mean±S.D., *p-0.05, same number of animals as above).
Figure 8O:
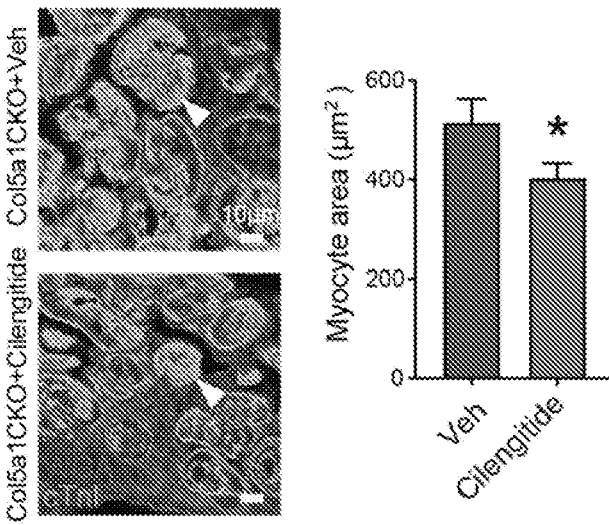

Considering these observations, the effects of injecting cilengitide in vivo to Col5a1CKO animals was investigated to determine effects on post injury cardiac dysfunction, scar size and myofibroblast formation. Col5a1CKO and control littermate animals were subjected to ischemic cardiac injury and were injected with cilengitide or vehicle at 20 mg/kg daily for 14 days starting from the day of injury (FIG. 8G). The Col5a1CKO animals injected with vehicle exhibited a significant decline in post injury cardiac function compared to the control animals as demonstrated above, but the Col5a1CKO animals treated with cilengitide had a complete rescue of function and the post injury heart function was not significantly different from the control littermates (Cre(–) Col5a1f/fl) (FIGS. 8H and 8I) In contrast, cilengitide infusion did not affect post injury cardiac function of control (Cre(–)Col5a1fl/fl) littermate animals (FIG. 8H). Masson trichrome staining was performed on hearts harvested at 2 weeks post injury and observed significant reduction in scar size in Col5a1CKO animals injected with cilengitide compared to vehicle injected Col5a1CKO animals (Scar size expressed as a fraction of left ventricular surface area of 41.2±16.1% in Col5a1CKO+ cilengitide group, 66.3±18.4% in Col5a1 CKO vehicle group and 36.61±14.7% in control+ Vehicle group; meant±S.D. *p<0.05 between Col5a1CKO+ cilengitide versus Col5a1CKO+vehicle groups and p>0.05 between Col5a1CKO+vehicle and control±vehicle group, n=9 CKO+cilengitide, n=3 CKO+vehicle, n=4 for all other groups) (FIGS. 8J and 8K). Cilengitide did not affect the scar size of control animals [Cre(–)Col5a1/fl] following injury (FIGS. 8J and 8K). The Col5a1CKO group of animals injected with cilengitide had a much lower fraction of animals exhibiting severe fibrosis compared to the PBS injected group (22% versus 67%) (FIG. 8L). The numbers of myofibroblasts in the scars of Col5a1CKO animals were examined following 2 weeks of cilengitide injection and the number of myofibroblasts (identified by αSMA+vimentin+ cells/vimentin+cells) was significantly reduced in the cilengitide group compared to vehicle injected group (mean±SD. *p<0.05 n=49 CKO-cilengitide, n=3 CKO-vehicle) (FIG. 8M). The degree of myocyte hypertrophy in the border zone was also substantially reduced in the Col5a1CKO animals that received cilengitide compared to vehicle injected group as assessed by heart weight/body weight ratios and histological analysis (mean±S.D. *p<0.05 n=9 CKO+cilengitide, n=–3 CKO+vehicle) (FIGS. 8N and 8O). Taken together these experiments demonstrate that the differential expression of αvβ3 and αvβ5 integrins in cardiac fibroblasts of Col5a1CKO animals drives myofibroblast differentiation and pharmacologic inhibition of such integrins is sufficient to rescue the phenotype.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

I claim:

1. A method of treating a subject with classic Ehlers Danlos syndrome (EDS), comprising administering cilengitide to the subject.

2. The method of claim 1, wherein the subject has dysregulated wound healing.

3. The method of claim 1, wherein the subject has acute myocardial infarction.

4. The method of claim 1, wherein the subject suffers from exaggerated and aberrant wound healing with increased scarring following injury trauma or surgery.

5. The method of claim 1, wherein the subject has a mutation in Col5a1.

6. The method of claim 5, wherein the mutation is haploinsufficiency.

7. The method of claim 1, wherein the subject exhibits up-regulation of αvβ3 integrin receptor.

8. The method of claim 1, wherein cilengitide is administered 1 to 30 days prior to a surgery or childbirth.

9. The method of claim 8, wherein cilengitide is administered 7 days prior to the surgery or childbirth.

10. The method of claim 8, wherein cilengitide is administered daily.

11. The method of claim 8, wherein cilengitide is administered after the surgery or childbirth until healing of wound has occurred.

12. The method of claim 8, wherein cilengitide is administered 1 to 30 days after the surgery or childbirth.

13. The method of claim 8, wherein cilengitide is administered 1 to 7 days after the surgery or childbirth.

14. The method of claim 8, wherein the cilengitide is administered daily.

15. The method of claim 1, wherein cilengitide is administered after an acute trauma until healing of wound has occurred.

16. The method of claim 1, wherein cilengitide is administered 1 to 30 days after the acute trauma, 1 to 14 days after the acute trauma, or 1 to 7 days after the acute trauma.

17. The method of claim 15, wherein cilengitide is administered daily.

\* \* \* \* \*